(12) United States Patent
Wang

(10) Patent No.: US 7,807,405 B2
(45) Date of Patent: *Oct. 5, 2010

(54) GLYCOPROTEIN SYNTHESIS AND REMODELING BY ENZYMATIC TRANSGLYCOSYLATION

(75) Inventor: Lai-Xi Wang, Ellicott City, MD (US)

(73) Assignee: University of Maryland Baltimore, Office of Commercial Ventures and Intellectual Property, Baltimore, MD (US)

(*) Notice: Subject to any disclaimer, the term of this patent is extended or adjusted under 35 U.S.C. 154(b) by 140 days.

This patent is subject to a terminal disclaimer.

(21) Appl. No.: 11/760,434

(22) Filed: Jun. 8, 2007

(65) Prior Publication Data

US 2008/0138855 A1 Jun. 12, 2008

(51) Int. Cl.
C12P 21/06 (2006.01)
A61K 39/21 (2006.01)
C07K 1/00 (2006.01)
C07K 1/113 (2006.01)
C07K 14/16 (2006.01)

(52) U.S. Cl. ............... 435/68.1; 424/188.1; 530/388.3; 530/395

(58) Field of Classification Search .................. None
See application file for complete search history.

(56) References Cited

U.S. PATENT DOCUMENTS

| 5,122,368 | A | 6/1992 | Greenfield et al. |
| 2004/0137557 | A1* | 7/2004 | DeFrees et al. ............ 435/68.1 |
| 2005/0159341 | A1 | 7/2005 | Wang et al. |
| 2005/0176642 | A1 | 8/2005 | Wang et al. |
| 2005/0244424 | A1 | 11/2005 | Wang |
| 2007/0224211 | A1 | 9/2007 | Wang |

OTHER PUBLICATIONS

Li, B., et al. "Highly Efficient Endoglycosidase-Catalyzed Synthesis of Glycopeptides Using Oligosaccharide Oxazolines as Donor Substrates" *J. Am. Chem. Soc.*, 2005, 127 (27), pp. 9692-9693.*
Rizzuto, C.D., et al. "A Conserved HIV gp120 Glycoprotein Structure Involved in Chemokine Receptor Binding" Science 1998, 280, pp. 1949-1953.*
Ermolat'ev, D., et al. "Indirect Coupling of the 2(1H)-pyrazinone Sacffold with Various (oligo)-saccharides via 'click chemistry': en route towards Glycopeptidomimetics" QSAR & Combinatorial Science, 2004, 23(10), pp. 915-918.*
Varki A. 1993. Biological roles of oligosaccharides—all of the theories are correct. *Glycobiology*, 3(2): 97-130.
Dwek, R. A. 1996. Glycobiology: Toward understanding the function of sugars. *Chem. Rev.*, 96(2): 683-720.
Jefferis R. 2005. Glycosylation of recombinant antibody therapeutics. *Biotechnol. Prog.*, 21(1): 11-6.
Davis B. G. 2004. Biochemistry—Mimicking posttranslational modifications of proteins. *Science*, 303(5657): 480-482.

Macmillan D., Bertozzi C. R. 2004. Modular assembly of glycoproteins: towards the synthesis of GlyCAM-1 by using expressed protein ligation. *Angew. Chem.*, 116: 1379-1383; *Angew. Chem. Int. Ed.* 2004, 43, 1355-1359.
Geng X., Dudkin V. Y., Mandal M., Danishefsky S. J. 2004. In pursuit of carbohydrate-based HIV vaccines, Part 2: The total synthesis of high-mannose-type gp120 fragments—evaluation of strategies directed to maximal convergence. *Angew. Chem.*, 116, 2616-2619; *Angew Chem. Int. Ed.* 2004, 43, 2562-2565.
Macmillan D., Bill R. M., Sage K. A., Fern D., Flitsch S. L. 2001. Selective in vitro glycosylation of recombinant proteins: semi-synthesis of novel homogeneous glycoforms of human erythropoietin. *Chem. Biol.*, 8(2): 133-145.
Watt G. M., Lund J., Levens M., Kolli V. S., Jefferis R., Boons G. J. 2003. Site-specific glycosylation of an aglycosylated human IgG1-Fc antibody protein generates neoglycoproteins with enhanced function. *Chem. Biol.*, 10(9): 807-814.
Mezzato S., Schaffrath M., Unverzagt C. 2005. An orthogonal double-linker resin facilitates the efficient solid-phase synthesis of complex-type N-glycopeptide thioesters suitable for native chemical ligation. *Angew. Chem.*, 117, 1677-1681; *Angew. Chem. Int. Ed.* 2005, 44(11): 1650-1654.
Fumoto M., Hinou H., Matsushita T., Kurogochi M., Ohta T., Yamada K., Takimoto A., Kondo H., Inazu T., Nishimura S. 2005. Molecular transporter between polymer platforms: Highly efficient chemoenzymatic glycopeptide synthesis by the combined use of solid-phase and water-soluble polymer supports. *Angew. Chem.*, 117, 2590-2593; *Angew. Chem. Int. Ed.* 2005, 44(17): 2534-2537.
Yamamoto K. 2001. Chemo-enzymatic synthesis of bioactive glycopeptides using microbial endoglycosidase. *J. Biosci. Bioeng.*, 92(6): 493-501.
Takegawa K., Tabuchi M., Yamaguchi S., Kondo A., Kato I., Iwahara S. 1995. Synthesis of neoglycoproteins using oligosaccharide-transfer activity with endo-beta-N-acetylglucosaminidase. *J. Biol. Chem.*, 270(7): 3094-3099.

(Continued)

Primary Examiner—Christopher R Tate
Assistant Examiner—Aaron J Kosar
(74) Attorney, Agent, or Firm—Marianne Fuierer; Moore & Van Allen, PLLC

(57) ABSTRACT

A chemoenzymatic method for the preparation of a homogeneous glycoprotein or glycopeptide, including (a) providing an acceptor selected from the group consisting of GlcNAc-protein and GlcNAc-peptide; and (b) reacting the acceptor with a donor substrate including an activated oligosaccharide moiety, in the presence of a catalyst comprising endoglycosidase (ENGase), to transfer the oligosaccharide moiety to the acceptor and yield the homogeneous glycoprotein or glycopeptide. The donor substrate includes, in a specific implementation, a synthetic oligosaccharide oxazoline. A related method of glycoprotein or glycopeptide remodeling with a predetermined natural N-glycan or a tailor-made oligosaccharide moiety, and a method of remodeling an antibody including a heterogeneous sugar chain, are also described. The disclosed methodology enables glycoprotein drugs to be modified for prolonged half-life in vivo, reduced immunogenicity, and enhanced in vivo activity, and for targeting and drug delivery.

9 Claims, 16 Drawing Sheets

OTHER PUBLICATIONS

Haneda K., Inazu T., Yamamoto K., Kumagai H., Nakahara Y., Kobata A. 1996. Transglycosylation of intact sialo complex-type oligosaccharides to the N-acetylglucosamine moieties of glycopeptides by Mucor hiemalis endo-beta-N-acetylglucosaminidase. *Carbohydr. Res.*, 292: 61-70.

Wang L. X., Fan J. Q., Lee Y. C. 1996. Chemoenzymatic synthesis of a high-mannose-type N-glycopeptide analog with C-glycosidic linkage. *Tetrahedron Lett.*, 37(12): 1975-1978.

Haneda K., Tagashira M., Yoshino E., Takeuchi M., Inazu T., Toma K., Iijima H., Isogai Y., Hori M., Takamatsu S., Fujibayashi Y., Kobayashi K., Yamamoto K. 2004. Chemo-enzymatic synthesis and structure-activity study of artificially N-glycosylated eel calcitonin derivatives with a complex type oligosaccharide. *Glycoconjugate J.*, 21(6): 377-386.

Singh S., Ni J., Wang L. X. 2003. Chemoenzymatic synthesis of high-mannose type-HIV-1 gp120 glycopeptides. *Bioorg. Med. Chem. Lett.*, 13(3): 327-330.

Li H., Singh S., Zeng Y., Song H., Wang L. X. 2005. *Bioorg. Med. Chem. Lett.* 2005, 15(4): 895-898.

Wang L. X., Song H., Liu S., Lu H., Jiang S., Ni J., Li H. 2005. Chemoenzymatic synthesis of HIV-1 gp41 glycopeptides: Effects of glycosylation on the anti-HIV activity and alpha-helix bundle-forming ability of peptide C34. *ChemBioChem*, 6(10): 1068-1074.

Crout D. H., Vic G. 1998. Glycosidases and glycosyl transferases in glycoside and oligosaccharide synthesis. *Curr. Opin. Chem. Biol.*, 2(1): 98-111.

Brameld K. A., Shrader W. D., Imperiali B., Goddard, 3rd W. A. 1998. Substrate assistance in the mechanism of family 18 chitinases: Theoretical studies of potential intermediates and inhibitors. *J. Mol. Biol.*, 280(5): 913-923.

Terwisscha van Scheltinga A. C., Armand S., Kalk K. H., Isogai A., Henrissat B., Dijkstra B. W. 1995. Stereochemistry of chitin hydrolysis by a plant chitinase lysozyme and X-ray structure of a complex with allosamidin—Evidence for substrate assisted catalysis. *Biochemistry*, 34(48): 15619-15623.

Mark B. L., Vocadlo D. J., Knapp S., Triggs-Raine B. L., Withers S. G., James M. N. 2001. Crystallographic evidence for substrate-assisted catalysis in a bacterial beta-hexosaminidase. *J. Biol. Chem.*, 276(13): 10330-1033.

Fujita M., Shoda S., Haneda K., Inazu T., Takegawa K., Yamamoto K. 2001. A novel disaccharide substrate having 1,2-oxazoline moiety for detection of transglycosylating activity of endoglycosidases. *Biochim. Biophys. Acta*, 1528(1): 9-14.

Ochiai H., Ohmae M., Kobayashi S. 2004. Enzymatic glycosidation of sugar oxazolines having a carboxylate group catalyzed by chitinase. *Carbohydr. Res.*, 339(17): 2769-2788.

Dudkin V. Y., Crich D. 2003. A short synthesis of the trisaccharide building block of the N-linked glycans. *Tetrahedron Lett.*, 44(9): 1787-1789.

Shing T. K. M., Perlin A. S. 1984. Synthesis of benzyl 2-azido-2-deoxy-4-O-β-D-glucopyranosyl-α-D-glucopyranoside and 1,6-anhydro-2-azido-2-deoxy-4-O-β-D-glucopyranosyl-β-D-glucopyranose. *Carbohydr. Res.* 1984, 130, 65-72.

Nakabayashi S., Warren C. D., Jeanloz R. W. 1986. A new procedure for the preparation of oligosaccharide oxazolines. *Carbohydr. Res.*, 150(1): C 7-C10.

Twaddle G. W. J., Yashunsky D. Y., Nikolaev A. V. 2003. The chemical synthesis of β-(1,4)-linked D-mannobiose and D-mannotriose. *Org. Biomol. Chem.*, 1(4): 623-628.

David S., Malleron A., Dini C. 1989. Preparation of oligosaccharides with β-D-mannopyranosyl and 2-azido-2-deoxy-β-D-mannopyranosyl residues by inversion at C-2 after coupling. *Carbohydr. Res.*, 188: 193-200.

Günther W., Kunz H. 1992. Synthesis of β-D-mannosides from β-D-glucosides via an intramolecular SN2 reaction at C-2. *Carbohydr. Res.*, 228(1): 217-241.

Günther W., Kunz H. 1990. Synthesis of a beta-mannosyl-chitobiosyl-asparagine conjugate—a central core region unit of the N-glycoproteins. *Angew. Chem.*, 102, 1068-1069; *Angew. Chem. Int. Ed. Engl.* 1990, 29(9): 1050-1051.

DeNinno M. P., Etienne J. B., Duplantier K. C. 1995. A method for the selective reduction of carbohydrate 4,6-O-benzylidene acetals. *Tetrahedron Lett.*, 36(5): 669-672.

Rush R. S., Derby P. L., Smith D. M., Merry C., Rogers G., Rohde M. F., Katta V. 1995. Microheterogeneity of erythropoietin carbohydrate structure. *Anal. Chem.*, 67(8): 1442-1452.

Li H., Li B., Song H., Breydo L., Baskakov I. V., Wang L. X. 2005. Chemoenzymatic synthesis of HIV-1V3 glycopeptides carrying two N-glycans and effects of glycosylaton on the peptide domain. *J. Org. Chem.*, 70(24): 9990-9996.

Lund, J., Takahashi, N., Popplewell, A., Goodall, M., Pound, J. D., Tyler, R., King, D. J., and Jefferis, R. 2000. Expression and characterization of truncated forms of humanized L243 IgG1—Architectural features can influence synthesis of its oligosaccharide chains and affect superoxide production triggered through human Fc gamma receptor I. *Eur J Biochem.*,. 267(24): 7246-7257.

Shoda S., Kiyosada T., Mori H., Kobayashi S. 2000. Chitinase-catalyzed synthesis of oligosaccharides by using a sugar oxazoline as glycosyl donor. *Heterocycles*, 52(2): 599-602.

Takegawa K., Yamaguchi S., Kondo A., Iwamoto H., Nakoshi M., Kato I., Iwahara S. Transglycosylation activity of endo-beta-N-acetylglucosaminidase from Arthrobacter-protophormiae. 1991. *Biochem. Int.*, 24(5): 849-855.

Yamamoto K., Kadowaki S., Watanabe J., Kumagai H. 1994. *Biochem. Biophys. Res. Commun.*, 203, 244-252.

Lemieux, R.U; Ratcliffe R.M; The Azidonitration of tri-O-acetyl-D-galactal; Can J. Chem, 1979, 57, 1244-1251.

Rudd P. M., Elliott T., Cresswell P., Wilson I. A.,. Dwek R. A. 2001. Glycosylation and the immune system. *Science*, 291(5512): 2370-2376.

Arnold J. N., Wormald R. M., Sim R. B., Rudd P. M., Dwek R. A. 2007. The impact of glycosylation on the biological function and structure of human immunoglobulins. *Annu. Rev. Immunol.*, 25, 21-50.

Arsequell G., Valencia G., 1999. Recent advances in the synthesis of complex N-glycopeptides. *Tetrahedron: Asymmetry*, 10(16): 3045-3094.

Koeller K. M., Wong C. H. 2000. Emerging themes in medicinal glycoscience. *Nat. Biotechnol.*, 18(8): 835-841.

Seitz O. 2000. Glycopeptide synthesis and the effects of glycosylation on protein structure and activity. *ChemBioChem*, 1(4): 214-246.

Herzner H., Reipen T., Schultz M., Kunz H. 2000. Synthesis of glycopeptides containing carbohydrate and peptide recognition motifs. *Chem. Rev.*, 100(12): 4495-4538.

Davis B. G. 2002. Synthesis of glycoproteins. *Chem. Rev.*, 102(2): 579-601.

Grogan M. J., Pratt M. R., Marcaurelle L. A., Bertozzi C. R. 2002. Homogeneous glycopeptides and glycoproteins for biological investigation. *Annu. Rev. Biochem.*, 71: 593-634.

Seeberger P. H. 2003. Automated carbohydrate synthesis to drive chemical glycomics. *Chem. Commun.*, 10: 1115-1121.

Hanson S., Best M., Bryan M. C., Wong C. H. 2004. Chemoenzymatic synthesis of oligosaccharides and glycoproteins. *Trends Biochem. Sci.*, 29(12): 656-663.

Wong C. H. 2005. Protein glycosylation: New challenges and opportunities. *J. Org. Chem.*, 70(11): 4219-4225.

Warren J. D., Miller J. S., Keding S. J., Danishefsky S. J. 2004. Toward fully synthetic glycoproteins by ultimately convergent routes: A solution to a long-standing problem. *J. Am. Chem. Soc.*, 126(21): 6576-6578.

Davis B. G., Lloyd R. C., Jones J. B. 1998. Controlled site-selective glycosylation of proteins by a combined site-directed mutagenesis and chemical modification approach. *J. Org. Chem.*, 63(26): 9614-9615.

Ni J., Singh S., Wang L. X. 2003. Synthesis of maleimide-activated carbohydrates as chemoselective tags for site-specific glycosylation of peptides and proteins. *Bioconjugate Chem.*, 14(1): 232-238.

Matsushita T., Hinou H., Kurogochi M., Shimizu H., Nishimura S. 2005. Rapid microwave-assisted solid-phase glycopeptide synthesis. *Org. Lett.*, 7(5): 877-880.

Kajihara Y., Yamamoto N., Miyazaki T., Sato H. 2005. Synthesis of diverse asparagine linked oligosaccharides and synthesis of sialylglycopeptide on solid phase. *Curr. Med. Chem.*, 12(5): 527-550.

Wang L. X., Singh S., Ni J., in *Synthesis of Carbohydrates through Biotechnology* (Eds.: P. G. Wang, Y. Ichikawa), American Chemical Society, Washington, DC, 2004, pp. 73-92.

Wang L. X., Tang M., Suzuki T., Kitajima K., Inoue Y., Inoue S., Fan J. Q., Lee Y. C. 1997. Combined chemical and enzymatic synthesis of a C-glycopeptide and its inhibitory activity toward glycoamidases. *J. Am. Chem. Soc.*, 119(46): 11137-11146.

Mizuno M., Haneda K., Iguchi R., Muramoto I., Kawakami T., Aimoto S., Yamamoto K., Inazu T. 1999. Synthesis of a glycopeptide containing oligosaccharides: Chemoenzymatic synthesis of eel calcitonin analogues having natural N-linked oligosaccharides. *J. Am. Chem. Soc.*, 121(2): 284-290.

Fujita K., Takegawa K. 2001. Chemoenzymatic synthesis of neoglycoproteins using transglycosylation with endo-β-N-acetylglucosaminidase A. *Biochem. Biophys. Res. Commun.*, 282(3): 678-682.

Li B., Zeng Y., Hauser S., Song H., Wang L. X. 2005. Highly efficient endoglycosidase-catalyzed synthesis of glycopeptides using oligosaccharide oxazolines as donor substrates. *J. Am. Chem. Soc.*, 127(27): 9692-9693.

Tews I., Terwisscha van Scheltinga A. C., Perrakis A., Wilson K. S., Dijkstra B. W. 1997. Substrate-assisted catalysis unifies two families of chitinolytic enzymes. *J. Am. Chem. Soc.*, 119(34): 7954-7959.

Williams S. J., Mark B. L., Vocadlo D. J., James M. N., Withers S. G. 2002. Aspartate 313 in the Streptomyces plicatus hexosaminidase plays a critical role in substrate-assisted catalysis by orienting the 2-acetamido group and stabilizing the transition state. *J. Biol. Chem.*, 277(42): 40055-40065.

Kobayashi S., Kiyosada T., Shoda S. 1996. Synthesis of artificial chitin: Irreversible catalytic behavior of a glycosyl hydrolase through a transition state analogue substrate. *J. Am. Chem. Soc.*, 118(51): 13113-13114.

Kobayashi S., Morii H., Itoh R., Kimura S., Ohmae M. 2001. Enzymatic polymerization to artificial hyaluronan: A novel method to synthesize a glycosaminoglycan using a transition state analogue monomer. *J. Am. Chem. Soc.*, 123(47): 11825-11826.

Kobayashi S., Fujikawa S., Ohmae M. 2003. Enzymatic synthesis of chondroitin and its derivatives catalyzed by hyaluronidase. *J. Am. Chem. Soc.*, 125(47): 14357-14369.

Elliott S., Lorenzini T., Asher S., Aoki K., Brankow D., Buck L., Busse L., Chang D., Fuller J., Grant J., Hernday N., Hokum M., Hu S., Knudten A., Levin N., Komorowski R., Martin F., Navarro R., Osslund T., Rogers G., Rogers N., Trail G., Egrie J. 2003. Enhancement of therapeutic protein in vivo activities through glycoengineering. *Nat. Biotechnol.*, 21(4): 414-421.

Li, B., Song, H., Hauser, S., and Wang, L. X. 2006. A highly efficient chemoenzymatic approach toward glycoprotein synthesis. *Org. Lett.*, 8(14): 3081-3084.

\* cited by examiner

Ac-W-M-E-W-D-R-E-I-N-N-Y-T-S-L-I-H-S-L-I-E-
E-S-Q-N-Q-Q-E-K-N-E-Q-E-L-L-NH$_2$

32

↑ 3 | Endo-A
     75%

Ac-W-M-E-W-D-R-E-I-N-N-Y-T-S-L-I-H-S-L-I-E-
E-S-Q-N-Q-Q-E-K-N-E-Q-E-L-L-NH$_2$

↓ 4 | Endo-A
     68%

Ac-W-M-E-W-D-R-E-I-N-N-Y-T-S-L-I-H-S-L-I-E-
E-S-Q-N-Q-Q-E-K-N-E-Q-E-L-L-NH$_2$

33

GLYCOPROTEIN SYNTHESIS AND REMODELING BY ENZYMATIC TRANSGLYCOSYLATION

GOVERNMENT RIGHTS IN INVENTION

Work related to the invention was conducted in the performance of NIAID/NIH contract no. NIAID/NIH R01 AI067111-01A1 and NIGMS/NIH R01 GM073717-A2. As a result of such contracts, the U.S. Government has certain rights in the invention described herein.

CROSS-REFERENCE TO RELATED APPLICATION

The present application claims priority to PCT Application No. PCT/US07/65052 filed in the U.S. Patent and Trademark Office, PCT Division, on Mar. 27, 2007, which in turn claims priority to U.S. Provisional Patent Application No. 60/786,185 filed on Mar. 27, 2006, the contents of which are hereby incorporated by reference herein.

BACKGROUND OF THE INVENTION

1. Field of the Invention

The invention relates to glycoprotein synthesis, and more particularly, to the synthesis of homogeneous glycoproteins wherein one or more oligosaccharide sugar chains with a predetermined number of sugar moieties are added to a GlcNAc-containing polypeptide/protein and wherein the oligosaccharide sugar chains may further include a functional moiety.

2. Description of the Related Art

Glycoproteins are an important class of biomolecules that play crucial roles in many biological events such as cell adhesion, tumor metastasis, pathogen infection, and immune response [1]. However, a major problem in structural and functional studies of glycoproteins is their structural microheterogeneity. Natural and recombinant glycoproteins are typically produced as a mixture of glycoforms that differ only in the structure of the pendent oligosaccharides.

Most mammalian cell surface proteins and human serum proteins are glycoproteins and therapeutic glycoproteins are an important class of biotechnology products. They include granulocyte macrophage-colony stimulating factor, tissue plasminogen activator, interleukin-2, and erythropoietin (EPO), which alone generates sales of 3-5 billion dollars annually.

A major challenge in preparation of protein-based drugs is post-translational modifications (glycosylation, phosphorylation, acetylation, etc.) that cannot be deduced directly from the sequence. Elucidating the roles of post-translational modifications has a direct impact on development of therapeutic glycoprotein. Glycosylation is one of the most common post-translational modifications of proteins in eukaryotes. Control of proper glycosylation is of major importance in the development of glycoprotein and glycopeptide drugs, because the attached sugar chains can have profound effects on protein folding, stability, action, pharmacokinetics, and serum half-life.

Therapeutic glycoproteins are typically produced in cell culture systems as a mixture of glycoforms that possess the same peptide backbone but differ in both the nature and site of glycosylation. The heterogeneity in glycosylation poses significant difficulty in the development of glycoprotein drugs. For example, expression of EPO in E. coli has been found to result in non-glycosylated EPO that shows only minimal activity, and EPO overproduced in plant cells such as tobacco cells has been found to produce no biological activity in vivo, presumably due to a high clearance rate resulting from a lack of masking sialic acid residues in the N-glycans.

Cell engineering and some biochemical modifications have yielded recombinant glycoproteins with predominant glycoforms but, in most cases, as with natively expressed glycoproteins, the structures that have been obtained remain heterogeneous. Notably, some glycoforms can cause allergy problems and undesired immune responses.

Antibodies, especially monoclonal antibodies (mAbs) are emerging as an important class of therapeutic agents for the treatment of human diseases such as cancer. Currently, antibodies used for treatment are the IgG type and are produced in mammalian cells (CHO cells or mouse NSO cell lines etc.). All types of antibodies including monoclonal antibodies are glycoproteins. More and more evidence have shown that different glycosylation forms can exert significantly different effects on the properties of a given therapeutic antibody, some sugar chains are beneficial, while others are detrimental [1d, 1e]. Unfortunately, recombinant mAbs are usually produced as a mixture of various glycosylation states, in which the more active glycosylation states (e.g., de-fucosylated and/or bisecting GlcNAc-containing N-glycans) that demonstrate enhanced ADCC effector functions are present only in minor amounts [1e].

A typical immunoglobulin G (IgG) antibody is composed of two light and two heavy chains that are associated with each other to form three major domains connected through a flexible hinge region: the two identical antigen-binding (Fab) regions and the constant (Fc) region. The IgG-Fc region is a homodimer in which the two $C_H3$ domains are paired through non-covalent interactions. The two $C_H2$ domains are not paired but each has a conserved N-glycosylation site at Asn-297. After the antibody's recognition and binding to a target cell, ADCC and other effector functions are triggered through the binding of the antibody's Fc region to ligands or receptors.

It is noted that there are heterogeneous glycosylation states of the human IgG when expressed in mammalian cell lines (e.g., CHO cell lines), and isolation of human IgG having a particular glycosylation state from this mixture is extremely difficult. Small amounts of impurities of a highly active species can dramatically interfere with the results and data interpretation.

As such, there is a need for proper and consistent glycosylation in developing glycoprotein therapeutic agents including antibodies to reduce allergy problems or undesired immune responses; confer significant stability and effector activity of an antibody and for compliance with US FDA regulations to obtain market approval.

SUMMARY OF THE INVENTION

The present invention relates to the synthesis of a glycopeptide or glycoprotein wherein a desired sugar chain is added to a GlcNAc-protein by transglycosylation to form any desired glycopeptide or glycoprotein with specific sugar chains of choice. As such, the present invention allows the synthesis and remodeling of therapeutic glycopeptide or glycoprotein drugs, such as EPO, glycoprotein hormones, cytokines, therapeutic antibodies, and any designer glycopeptides or glycoproteins that show prolonged half-life time in vivo, are less immunogenic, show enhanced in vivo activity and can be used for targeting and drug delivery.

In one aspect, the present invention relates to the use of a synthetic oligosaccharide oxazolines, as donor substrates for the synthesis of homogeneous glycopeptides or glycoproteins.

In another aspect of the invention involving such synthesis, an intact oligosaccharide sugar chain is transferred from a pre-assembled sugar oxazoline to a N-acetylglucosamine (GlcNAc)-containing peptide or protein to form a homogeneous glycopeptide or glycoprotein with a tailor-made sugar chain.

In yet another aspect, the present invention provides for a method of generating a remodeled and homogeneous glycopeptide or glycoprotein, the method comprising;
(a) preparing a GlcNAc-containing peptide or protein precursor; and
(b) enzymatically adding an oligosaccharide to the a GlcNAc-containing peptide or protein precursor, wherein the oligosaccharide is a synthetic oligosaccharide oxazoline.

Preferably, a di-, tri-, tetra-, penta-, hexyl-, hepta-, octyl-, nona-, deca-, or undeca-saccharide oxazolines are utilized as donor substrates for a highly efficient chemoenzymatic synthesis of homogeneous N-glycopeptides or glycoproteins.

In a further aspect, the present invention relates to a chemoenzymatic method for the preparation of a homogeneous glycopeptide or glycoprotein, said method comprising:
(a) providing an acceptor glycopeptide or glycoprotein comprising a GlcNAc containing peptide or protein; and
(b) reacting the acceptor glycopeptide or glycoprotein with a donor substrate in the presence of an endoglycosidase (ENGase), wherein the donor substrate comprises a predetermined oligosaccharide component with a defined number and type of sugar residues and specific linkage types) thereby providing the homogeneous glycopeptide or glycoprotein.

In another aspect, the invention relates to a method of glycopeptide or glycoprotein remodeling with an oligosaccharide having a predetermined oligosaccharide component with a defined number and type of sugar residues with specific linkage types, the method comprising:
(a) providing a peptide or protein substrate comprising at least two GlcNAc residues;
(b) treating the peptide or protein substrate with an endoenzyme to hydrolyze the bond between two GlcNAc residues positioned closest to the peptide thereby forming a peptide or protein substrate with a single GlcNAc-moiety;
(c) attaching the oligosaccharide to single GlcNAc moiety in the presence of an endoglycosidase (ENGase) thereby adding a predetermined the oligosaccharide component.

In yet another aspect, the invention relates to a method of synthesizing homogeneous glycopeptide or glycoprotein, the method comprising:
(a) providing a heterogeneous glycopeptide or glycoprotein comprising different high mannose type N-glycans, wherein the heterogeneous glycoproteins may be obtained from natural sources, or may be produced from a wild type or engineered yeast system;
(b) removing the different high mannose type N-glycans by an enzyme selected from the group Endo-H or Endo-A to form a homogeneous GlcNAc-containing peptide or protein;
(c) providing a sugar containing oxazolines with a desired oligosaccharide component comprising a defined number and type of sugar residues in the chain; and
(d) enzymatically transglycosylating the GlcNAc-peptide to attach the sugar containing oxazoline to the homogeneous GlcNAc-containing peptide or protein thereby forming a homogeneous glycopeptide or protein with an extension of desired number of sugar residues.

In another aspect, the present invention relates to a method of synthesis of a modified antibody or fragment thereof, the method comprising;
(a) providing an antibody comprising at least one N-acetylglucosamine (GlcNAc) moiety to form GlcNAc-peptide acceptor; wherein the N-acetylglucosamine (GlcNAc) moiety is positioned on the Fc region of the antibody; and
(b) transglycosylating an oligosaccharide oxazoline having a predetermined oligosaccharide component and the GlcNAc-peptide acceptor under the catalysis of the enzyme Endo-A, Endo-M, or their mutants to form the modified antibody with the predetermined number of saccharides.

It is envisioned that the oligosaccharide oxazoline having a predetermined oligosaccharide component with a defined number and type of sugar residues further comprises an additional moiety including, a therapeutic agent or drug such as for treating cancer, HIV or other viruses, substances that activates receptors on the cell plasma membrane, agents that affects intracellular chemistry, agents that affects cellular physics, genes, gene analogs, RNA, RNA analogs, DNA, DNA analogs, amino acid sequences of surface receptors such as CCR5 or CD4, antigenic structure having affinity for a specific antibody; amino acid sequences of receptor ligands such as gp120, gp41 or gp160, receptor antagonists, receptor blockers, enzymes, enzyme substrates, enzyme inhibitors, enzyme modulators, therapeutic proteins, protein analogs, metabolites, metabolite analogs, oligonucleotides, oligonucleotide analogs, antigens, antigen analogs, antibodies or fragments thereof, antibody analogs, an antibody different from the modified antibody which is reactive to another receptor bacteria, viruses, inorganic ions, metal ions, metal clusters, polymers, fluorescent compounds and any combinations thereof.

As such, the present invention further provides a delivery device for delivering a drug having biological activity to treat a condition, the delivery device comprising: a remodeled having a predetermined sugar chain and a therapeutic agent or drug attached to the terminal sugar residue.

Additionally the present invention envisions modifying monoclonal antibodies related to HIV including, but not limited to 17b, 48d, A32, C11, 2G12, F240, IgG1b12, 19e, X5, TNX-355 and F91, all of which are commercially available.

A still further aspect of the invention relates to a method of remodeling an antibody comprising a heterogeneous sugar chain, including polyclonal and monoclonal, comprising:
(a) removing the heterogeneous sugar chain from the antibody with an endoglycosidase to leave a single GlcNAc attached to an original glycosylation site; and
(b) transferring a core oligosaccharide with at least one tag to said GlcNAc by ENGase-catalyzed transglycosylation to yield a tagged antibody.

The tag moiety may include, but is not limited to, antigens, therapeutic drugs such as for cancer or HIV, toxins, fluorescent probes, biotin, PEG species, lipids, or nucleotides.

Other aspects, features and embodiments of the invention will be more fully apparent from the ensuing disclosure and appended claims.

DETAILED DESCRIPTION OF THE INVENTION, AND PREFERRED EMBODIMENTS THEREOF

The practice of the present invention will employ, unless otherwise indicated, conventional techniques of immunology, molecular biology, microbiology, cell biology and recombinant DNA, which are within the skill of the art. See, e.g., Sambrook, et al. MOLECULAR CLONING: A LABORATORY MANUAL, 2nd edition (1989); CURRENT PROTOCOLS TN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

DEFINITIONS

As used in the specification herein, "a" or "an" may mean one or more. As used herein in the claim(s), when used in conjunction with the word "comprising", the words "a" or "an" may mean one or more than one. As used herein "another" may mean at least a second or more.

As used herein, "biological activity" refers to pharmacodynamic and pharmacokinetic properties including, for example, molecular affinity or resultant biochemical or physiological effect, receptor affinity or resultant biochemical or physiological effect, non-receptor affinity or biochemical or physiological effect, efficacy, bioavailability, absorption, distribution, metabolism, or elimination.

As used herein, "sugar" refers to an oxidized or unoxidized carbohydrate-containing molecule, including, but not limited to, a monosaccharide, disaccharide, trisaccharide, oligosaccharide, or polysaccharide, including, for example, N-acetylglucosamine, mannose, galactose, N-acetylneuraminic acid (sialic acid), glucose, fructose, fucose, sorbose, rhamnose, mannoheptulose, N-acetylgalactosamine, dihydroxyacetone, xylose, xylulose, arabinose, glyceraldehyde, sucrose, lactose, maltose, trehalose, cellobiose or any combination thereof of the L- or D-isomer. Sugar further refers to, such molecules produced naturally, recombinantly, synthetically, and/or semi-synthetically.

As used herein, modulates refers to an increase or decrease in "biological activity", as defined above, when comparing to a glycosylation-engineered antibody to a non-glycosylation-engineered antibody.

As used herein, an antibody is "homologous" when it constitutes at least 90%, more preferably at least 95%, and most preferably at least 99%, by weight, of the desired antibody. A homolgous antibody includes a naturally, recombinantly, or synthetically produced antibody.

Figure 14:
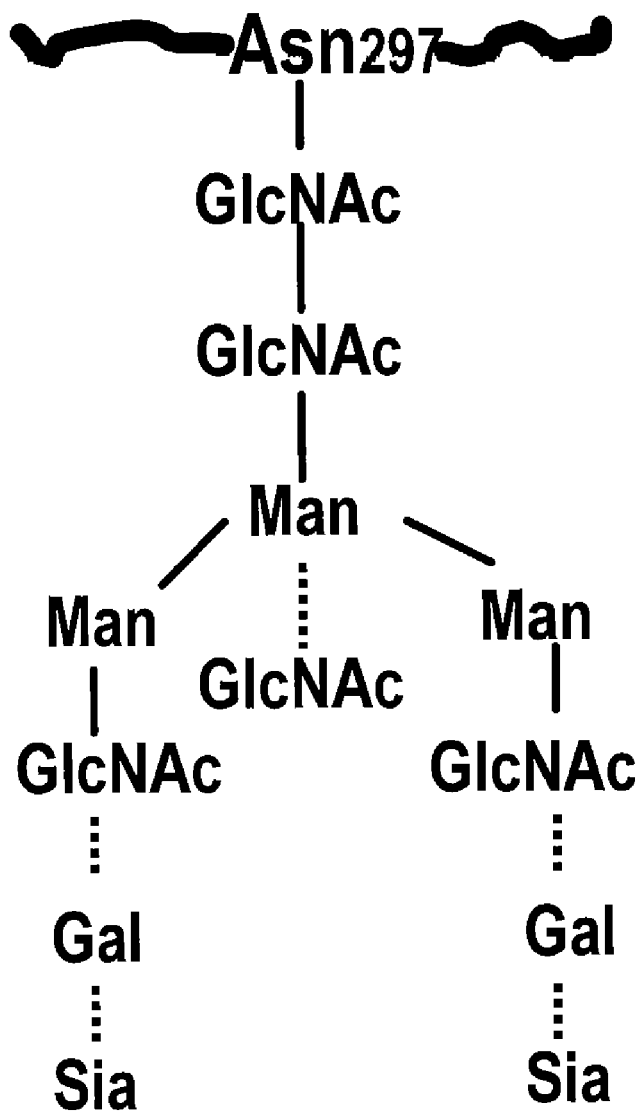

As used herein, "glycosylation state" refers to an antibody having a specific or desired glycosylation pattern. Such glycosylation patterns include, for example, attaching one or more sugars at position N-297 of a mAb, wherein said sugars are produced naturally, recombinantly, synthetically, or semi-synthetically. By way of example, an exemplary mAb having a glycosylation state comprises an IgG1 linked at position N-297 to at least one N-glycan and lacking an alpha-1,6-fucose is provided in FIG. 14.

The terms "immunoglobulin molecule" or "antibodies," as used herein, mean molecules that contain an antigen binding site which specifically binds an antigen or an Fc region that binds to cell receptors. Structurally, the simplest naturally occurring antibody (e.g., IgG) comprises four polypeptide chains, two heavy (H) chains and two light (L) chains interconnected by disulfide bonds. The natural immunoglobulins represent a large family of molecules that include several types of molecules, such as IgD, IgG, IgA, IgM and IgE. The term also encompasses hybrid antibodies, or altered antibodies, and fragments thereof, including but not limited to Fab fragment(s) and Fc fragment(s).

Antibodies can be fragmented using conventional techniques as described herein and the fragments screened for utility in the same manner as described for whole antibodies. A Fab fragment of an immunoglobulin molecule is a multimeric protein consisting of the portion of an immunoglobulin molecule containing the immunologically active portions of an immunoglobulin heavy chain and an immunoglobulin light chain covalently coupled together and capable of specifically combining with an antigen. Fab and Fc fragments can be prepared by proteolytic digestion of substantially intact immunoglobulin molecules with papain using methods that are well known in the art. However, a Fab or Fc fragment may also be prepared by expressing in a suitable host cell the desired portions of immunoglobulin heavy chain and immunoglobulin light chain using methods known in the art.

Antigens useful for attachment as a tag to a modified glycoprotein of the present invention and more preferably an antibody or fragment thereof may be a foreign antigen, an endogenous antigen, fragments thereof, or variants having the same functional activity.

As used herein, "foreign antigen" refers to a protein or fragment thereof, which is foreign to the recipient animal cell or tissue including, but not limited to, a viral protein, a parasite protein, an immunoregulatory agent, or a therapeutic agent.

The term "endogenous antigen" is used herein to refer to a protein or part thereof that is naturally present in the recipient animal cell or tissue, such as a cellular protein, an immunoregulatory agent, or a therapeutic agent.

The foreign antigen may be a protein, an antigenic fragment or antigenic fragments thereof that originate from viral and parasitic pathogens.

Alternatively, the foreign antigen may be encoded by a synthetic gene and may be constructed using conventional recombinant DNA methods; the synthetic gene may express antigens or parts thereof that originate from viral and parasitic pathogens. These pathogens can be infectious in humans, domestic animals or wild animal hosts.

The foreign antigen can be any molecule that is expressed by any viral or parasitic pathogen prior to or during entry into, colonization of, or replication in their animal host.

The viral pathogens, from which the viral antigens are derived include, but are not limited to, Orthomyxoviruses, such as influenza virus (Taxonomy ID: 59771); Retroviruses, such as RSV, HTLV-1 (Taxonomy ID: 39015) and HTLV-II (Taxonomy ID: 11909); Herpes viruses, such as EBV (Taxonomy ID: 10295), CMV (Taxonomy ID: 10358) or herpes simplex virus (ATCC #: VR-1487); Lentiviruses, such as HIV-1 (Taxonomy ID: 12721) and HIV-2 Taxonomy ID: 11709); Rhabdoviruses, such as rabies; Picornoviruses, such as Poliovirus (Taxonomy ID: 12080); Poxviruses, such as vaccinia Taxonomy ID: 10245); Rotavirus Taxonomy ID: 10912); and Parvoviruses, such as adeno-associated virus 1 (Taxonomy ID: 85106).

Examples of viral antigens include, but are not limited to, the human immunodeficiency virus antigens Nef (National Institute of Allergy and Infectious Disease HIV Repository Cat. #183; GenBank accession # AF238278), Gag, Env (National Institute of Allergy and Infectious Disease HIV Repository Cat. #2433; GenBank accession # U39362), Tat (National Institute of Allergy and Infectious Disease HIV Repository Cat. #827; GenBank accession # M13137), Rev (National Institute of Allergy and Infectious Disease HIV Repository Cat. #2088; GenBank accession # L14572), Pol (National Institute of Allergy and Infectious Disease HIV Repository Cat. #238; GenBank accession # AJ237568) and T cell and B cell epitopes of gp120 (Hanke and McMichael, AIDS Immunol Lett., 66:177 (1999); Hanke, et al., Vaccine, 17:589 (1999); Palker, et al., J. Immunol., 142:3612-3619 (1989)); the hepatitis B surface antigen (GenBank accession # AF043578); rotavirus antigens, such as VP4 (GenBank accession # AJ293721) and VP7 (GenBank accession # AY003871); influenza virus antigens, such as hemagglutinin (GenBank accession # AJ404627); nucleoprotein (GenBank accession # AJ289872); and herpes simplex virus antigens, such as thymidine kinase (GenBank accession # AB047378).

The bacterial pathogens, from which the bacterial antigens are derived, include but are not limited to, *Mycobacterium* spp., *Helicobacter pylori, Salmonella* spp., *Shigella* spp., *E. coli, Rickettsia* spp., *Listeria* spp., *Legionella pneumoniae, Pseudomonas* spp., *Vibrio* spp., and *Borellia burgdorferi*.

Examples of protective antigens of bacterial pathogens include the somatic antigens of enterotoxigenic *E. coli*, such as the CFA/I fimbrial antigen and the nontoxic B-subunit of the heat-labile toxin; pertactin of *Bordetella pertussis*, adenylate cyclase-hemolysin of *B. pertussis*, fragment C of tetanus toxin of *Clostridium tetani*, OspA of *Borellia burgdorferi*, protective paracrystalline-surface-layer proteins of *Rickettsia prowazekii* and *Rickettsia typhi*, the listeriolysin (also known as "Llo" and "Hly") and/or the superoxide dismutase (also know as "SOD" and "p60") of *Listeria monocytogenes*; the urease of *Helicobacter pylori*, and the receptor-binding domain of lethal toxin and/or the protective antigen of *Bacillus anthrax*.

Example of antigens from biological weapons or pathogens include, but are not limited to, smallpox, anthrax, tularemia, plague, listeria, brucellosis, hepatitis, vaccinia, mycobacteria, coxsackievirus, tuberculosis, malaria, erhlichosis and bacterial meningitis.

The parasitic pathogens, from which the parasitic antigens are derived, include but are not limited to, *Plasmodium* spp., such as *Plasmodium falciparum* (ATCC#: 30145); *Trypanosome* spp., such as *Trypanosoma cruzi* (ATCC#: 50797); *Giardia* spp., such as *Giardia intestinalis* (ATCC#: 30888D); *Boophilus* spp.; *Babesia* spp., such as *Babesia microti* (ATCC#: 30221); *Entamoeba* spp., such as *Entamoeba histolytica* (ATCC#: 30015); *Eimeria* spp., such as *Eimeria maxima* (ATCC#40357); *Leishmania* spp., (Taxonomy ID: 38568); *Schistosome* spp., such as *Schistosoma mansoni* (GenBank accession # AZ301495); *Brugia* spp., such as *Brugia malayi* (GenBank accession # BE352806); *Fascida* spp., such as *Fasciola hepatica* (GenBank accession # AF286903); *Dirofilaria* spp., such as *Dirofilaria immitis* (GenBank accession # AF008300); *Wuchereria* spp., such as *Wuchereria bancrofti* (GenBank accession # AF250996); and *Onchocerca* spp; such as *Onchocerca volvulus* (GenBank accession # BE588251).

Examples of parasite antigens include, but are not limited to, the pre-erythrocytic stage antigens of *Plasmodium* spp. such as the circumsporozoite antigen of *P. falciparum* (GenBank accession # M22982) *P vivax* (GenBank accession # M20670); the liver stage antigens of *Plasmodium* spp, such as the liver stage antigen 1 (as referred to as LSA-1; GenBank accession # AF086802); the merozoite stage antigens of *Plasmodium* spp; such as the merozoite surface antigen-1 (also referred to as MSA-1 or MSP-1; GenBank accession # AF199410); the surface antigens of *Entamoeba histolytica*, such as the galactose specific lectin (GenBank accession # M59850) or the serine rich *Entamoeba histolytica* protein (also referred to as SREHP; Zhang and Stanley, Vaccine, 18:868 (1999)); the surface proteins of *Leishmania* spp, such as 63 kDa glycoprotein (gp63) of *Leishmania major* (GenBank accession # Y00647 or the 46 kDa glycoprotein (gp46) of *Leishmania major*; paramyosin of *Brugia malayi* (GenBank accession # U77590; the triose-phosphate isomerase of *Schistosoma mansoni* (GenBank accession # W06781; the secreted globin-like protein of *Trichostrongylus colubriformis* (GenBank accession # M63263; the glutathione-S-transferases of *Fasciola hepatica* (GenBank accession # M77682; *Schistosoma bovis* (GenBank accession # M77682); *S. japonicum* (GenBank accession # U58012; and KLH of *Schistosoma bovis* and *S. japonicum* (Bashir, et al., supra).

Examples of tumor specific antigens include prostate specific antigen (PSA), TAG-72 and CEA; human tyrosinase (GenBank accession # M27160); tyrosinase-related protein (also referred to as TRP; GenBank accession # AJ132933); and tumor-specific peptide antigens.

Examples of transplant antigens include the CD3 molecule on T cells and histocompatibility antigens such as HLA A, HLA B, HLA C, HLA DR and HLA.

Examples of autoimmune antigens include IAS β chain, which is useful in therapeutic vaccines against autoimmune encephalomyelitis (GenBank accession # D88762); glatamic acid decarboxylase, which is useful in therapeutic vaccines against insulin-dependent type 1 diabetes (GenBank accession # NM013445); thyrotropin receptor (TSHr), which is useful in therapeutic vaccines against Grave's disease (GenBank accession # NM000369) and tyrosinase-related protein 1, which is useful in therapeutic vaccines against vitiligo (GenBank accession # NM000550).

HIV drugs that may be used in the construction of the tagged antibodies or fragments thereof include, but are not limited to antiviral agents such as nucleoside RT inhibitors, CCR5 inhibitors/antagonists, viral entry inhibitors and their functional analogs. Specifically, an antiviral agent may nucleoside RT inhibitors, such as Zidovudine (ZDV, AZT), Lamivudine (3TC), Stavudine (d4T), Didanosine (ddI), Zalcitabine (ddC), Abacavir (ABC), Emirivine (FTC), Tenofovir (TDF), Delaviradine (DLV), Efavirenz (EFV), Nevirapine (NVP), Saquinavir (SQV), Ritonavir (RTV), Indinavir (IDV), Nelfinavir (NFV), Amprenavir (APV), Lopinavir (LPV), Atazanavir, Combivir (ZDV/3TC), Kaletra (RTV/LPV), Trizivir (ZDV/3TC/ABC);

CCR5 inhibitors/antagonists, such as SCH-C, SCH-D, PRO 140, TAK 779, TAK-220, RANTES analogs, AK602, UK-427, 857, monoclonal antibodies; and viral entry inhibitors, such as Fuzeon (T-20) (enfuvirtide), NB-2, NB-64, T-649, T-1249, SCH-C, SCH-D, PRO 140, TAK 779, TAK-220, RANTES analogs, AK602, UK-427, 857; and functional analogs or equivalents thereof.

It is envisioned that many different polypeptide and/or glycoproteins can be modified according to the methods of the present invention or used as a therapeutic agent for conjugation to a terminal sugar including but not limited to, adrenocorticotropic hormone (ACTH); adrenocorticotropic hormone derivatives (e.g., ebiratide); angiotensin; angiotensin II; asparaginase; atrial natriuretic peptides; atrial sodium diuretic peptides; bacitracin; beta-endorphins; blood coagulation factors VII, VIII and IX; blood thymic factor (FTS); blood thymic factor derivatives (see U.S. Pat. No. 4,229,438); bombesin; bone morphogenic factor (BMP); bone morphogenic protein; bradykinin; caerulein; calcitonin gene related polypeptide (CGRP); calcitonins; cell growth factors (e.g., EGF; TGF-alpha; TGF-beta; PDGF; acidic FGF; basic FGF); cerulein; chemokines; cholecystokinin; cholecystokinin-8 (CCK-8); cholecystokinin-pancreozymin (CCK-PZ); colistin; colony-stimulating factors (e.g. CSF; GCSF; GMCSF; MCSF); corticotropin-releasing factor (CRF); cytokines; desmopressin; dinorphin; dipeptide; dismutase; dynorphin; eledoisin; endorphins; endothelin; endothelin-antagonistic peptides (see European Patent Publication Nos. 436189; 457195 and 496452 and Japanese Patent Unexamined Publication Nos. 94692/1991 and 130299/1991); endotherins; enkephalins; enkephalin derivatives (see U.S. Pat. No. 4,277,394 and European Patent Publication No. 31567); epidermal growth factor (EGF); erythropoietin (EPO); follicle-stimulating hormone (FSH); gallanin; gastric inhibitory polypeptide; gastrin-releasing polypeptide (GRP); gastrins; glucagon; glutathione peroxidase; glutathio-peroxidase; gonadotropins (e.g., human chorionic gonadotrophin (HCG) and .alpha. and .beta. subunits thereof); gramicidin; gramicidines; growth hormone-releasing factor (GRF); growth hormones; human artrial natriuretic polypeptide (h-ANP); human placental lactogen; insulin; insulin-like growth factors (IGF-I; IGF-II); interferon; interferons (e.g., alpha-, beta-, and gamma-interferons); interleukins (e.g. IL-1; IL-2; IL-3; IL-4; IL-5; IL-6; IL-7; IL-8; IL-9; IL-10; IL-11 and IL-12); kallikrein; kyotorphin; luliberin; luteinizing hormone (LH); luteinizing hormone-releasing hormone (LH-RH); lysozyme chloride; melanocyte-stimulating hormone (MSH); melanophore stimulating hormone; mellitin; motilin; muramyl; muramyldipeptide, nerve growth factor (NGF); nerve nutrition factors (e.g. NT-3; NT-4; CNTF; GDNF; BDNF); neuropeptide Y; neurotensin; oxytocin; pancreastatin; pancreatic polypeptide; pancreozymin; parathyroid hormone (PTH); pentagastrin; polypeptide YY; pituitary adenyl cyclase-activating polypeptides (PACAPs); platelet-derived growth factor; polymixin B; prolactin; protein synthesis stimulating polypeptide; PTH-related protein; relaxin; renin; secretin; serum thymic factor; somatomedins; somatostatins derivatives (Sandostatin; see U.S. Pat. Nos. 4,087,390; 4,093,574; 4,100,117 and 4,253,998); substance P; superoxide dismutase; taftsin; tetragastrin; thrombopoietin (TPO); thymic humoral factor (THF); thymopoietin; thymosin; thymostimulin; thyroid hormone releasing hormone; thyroid-stimulating hormone (TSH); thyrotropin releasing hormone (TRH); trypsin; tuftsin; tumor growth factor (TGF-alpha); tumor necrosis factor (TNF); tyrocidin; urogastrone; urokinase; vasoactive intestinal polypeptide (VIP); and vasopressin.

Glycoproteins are an important class of biomolecules that play crucial roles in many biological events such as cell adhesion, tumor metastasis, pathogen infection, and immune response. As indicated previously herein, a major problem in structural and functional studies of glycoproteins is their structural microheterogeneity. Natural and recombinant glycoproteins are typically produced as a mixture of glycoforms that differ only in the structure of the pendent oligosaccharides.

The present invention addresses the challenge of assembling homogeneous glycopeptides (partial structures of glycoproteins) and glycoproteins themselves by chemical/chemoenzymatic synthesis. In one embodiment, the invention utilizes endo-β-N-acetylglucosaminidase (ENGase)-catalyzed oligosaccharide transfer for glycopeptides or glycoprotein synthesis to enable the attachment of a large oligosaccharide to a pre-assembled, unprotected GlcNAc-peptide/protein in a single step in a regio- and stereospecific manner [6, 7].

Endo-A from *Arthrobacter protophormiae* [8] and the Endo-M from *Mucor hiemalis* [9] are two ENGases that possess significant transglycosylation activity. ENGases are a class of endoglycosidases that hydrolyze N-glycans by cleaving the β-1,4-glycosidic bond in the N,N'-diacetylchitobiose core, but like many glycosidase-catalyzed syntheses, ENGase-catalyzed transglycosylation suffers from the inherent low transglycosylation yield and product hydrolysis, and ENGase-catalyzed synthesis has been heretofore limited to the use of only natural N-glycans as the donor substrates, which themselves are difficult to obtain.

The present invention addresses such deficiencies of the prior art and provides a new and highly efficient approach toward glycoprotein synthesis and remodeling. The invention is based on the discovery that oligosaccharide sugar chains can be efficiently transferred to a N-acetylglucosamine (GlcNAc)-containing protein by endo-beta-N-acetylglucosaminidases (ENGases) from synthetic sugar oxazolines to form a homogeneous glycoprotein. The invention also reflects the discovery that modified sugar chains with tags can be correspondingly transferred, thereby enabling the preparation of homogeneous glycoproteins in which additional functional components such as toxins and antigens can be attached for various applications.

This present invention enables both total glycoprotein synthesis and recombinant glycoprotein remodeling.

For total glycoprotein synthesis, GlcNAc-containing proteins can be prepared by established solid-phase peptide synthesis protocols [4] in combination with native chemical ligation, expressed native protein ligation, and chemo-enzymatic synthesis.

For glycoprotein remodeling, a high-yield expression system such as an engineered yeast system (e.g., the single mutant Och1 or the double mutant Och1/Mnn-1 of *Saccharomyces cerevisiae* or *Pichia pastoris*) can be used to generate a heterogeneous glycoprotein (antibody) carrying mainly a Man8GlcNAc2 sugar chain, or a sugar chain containing a mixture of Man8-Man14 sugars.

The heterogeneous N-glycans can be removed by an endoglycosidase (ENGase), such as Endo-H and Endo-A, to give a homogeneous GlcNAc-containing protein. A desired sugar chain then can be added to the GlcNAc-protein by transglycosylation to form any desired glycoprotein with specific sugar chains of choice.

The invention allows the synthesis and remodeling of therapeutic glycoprotein drugs, such as EPO, glycoprotein hormones, cytokines, therapeutic antibodies, etc. For example, glycoprotein therapeutics can be produced with desired properties, such as prolonged half-life time in vivo, reduced immunogenicity, enhanced in vivo activity, etc., and such therapeutics can be specifically enhanced for targeting and drug delivery usage.

The invention enables a chemoenzymatic process to be carried out, to effect glycoprotein remodeling, involving change of the sugar chains in a natural or recombinant glycoprotein to convert heterogeneous glycoproteins to homogeneous glycoprotein with a sugar chain of choice. This capability facilitates the production of new and improved therapeutics for a wide variety of treatment indications.

The invention in various aspects reflects the discovery that selectively modified oligosaccharide oxazolines are tolerated by the endo-enzyme for transglycosylation, thus allowing the synthesis of modified, non-naturally-occurring glycoproteins in high yield.

Referring now more specifically to the invention, and various aspects and embodiments thereof, the present invention provides a general chemoenzymatic method for the preparation of homogeneous glycoproteins, including both natural and tailor-made glycoproteins. The present invention is based on the fact that that synthetic sugar oxazolines can serve as efficient donor substrates of some endoglycosidases (ENGases) for transferring to a GlcNAc-peptide and GlcNAc-protein acceptor to form a new glycopeptide and glycoprotein in a stereo- and regio-specific manner, and in a high-yield.

Generally, the method includes two key steps: a) the preparation of the acceptor, GlcNAc-protein and b) endoglycosidase (ENGase)-catalyzed transfer of an oligosaccharide moiety from a pre-assembled donor substrate, including a synthetic oligosaccharide oxazoline or other potential activated donors including a modified oxazoline to the acceptor GlcNAc-protein to form the desired glycoprotein.

Thus, the invention provides a general method for glycoprotein remodeling comprising the treatment of the natural or recombinant glycoproteins with an endo-enzyme (Endo-A, Endo-H, Endo-M, Endo-F, etc., depending on the nature of the N-glycans), which will hydrolyze the bond between the two GlcNAc residues in the N-acetylchitobiose core of the N-glycans to afford the GlcNAc-protein, with the inner GlcNAc residue being still attached to the original glycosylation sites. Then a prepared N-glycan with the desired sugar component (defined monosaccharide residues and linkage types) will be attached to the original glycosylation site(s) by the high-yield enzymatic oligosaccharide transfer from synthetic sugar oxazolines or other activated donor substrates (glycosyl fluoride and aryl glycoside may be used) by an ENGase or its more active mutants.

In this method, the GlcNAc-protein or GlcNAc-peptide can be prepared by a process such as chemical total protein synthesis, native chemical ligation, expressed protein ligation, etc. A multiplicity of N-glycans can be attached to the GlcNAc-protein or GlcNAc-peptide in such method. The GlcNAc-protein or GlcNAc-peptide can be prepared by a process in which a GlcNAc residue is inserted at a native glycosylation site in the corresponding protein or peptide, or in which the GlcNAc residue is inserted at an otherwise selected site in the corresponding protein or peptide.

A further aspect of the invention relates to a method of remodeling an antibody including a heterogeneous sugar chain, including:
(a) removing the heterogeneous sugar chain by from the antibody with an endoglycosidase to leave a single GlcNAc attached to an original glycosylation site; and
(b) transferring a core oligosaccharide with at least one tag to said GlcNAc by ENGase-catalyzed transglycosylation to yield a tagged antibody.

Such method may further include incorporating a functional component into the tagged antibody by selective ligation reaction to yield a functionalized antibody. The antibody may for example be functionalized for drug delivery, targeting a specific antigen, etc. The antibody may be functionalized with a functional component selected from among antigens, toxins, radioactive species, photoactive species, and polyethylene glycols. In a specific embodiment, the functionalized antibody is functionalized with alpha-Gal. The antibody itself may be of any suitable type, and may for example be an immunoglobulin, an antibody fragment, or other antibody species.

The endoglycosidase employed in such method may likewise be of any suitable type, e.g., Endo-F, and the aforementioned selective ligation reaction may include a click chemistry reaction or a Staudinger reaction.

Figure 1:
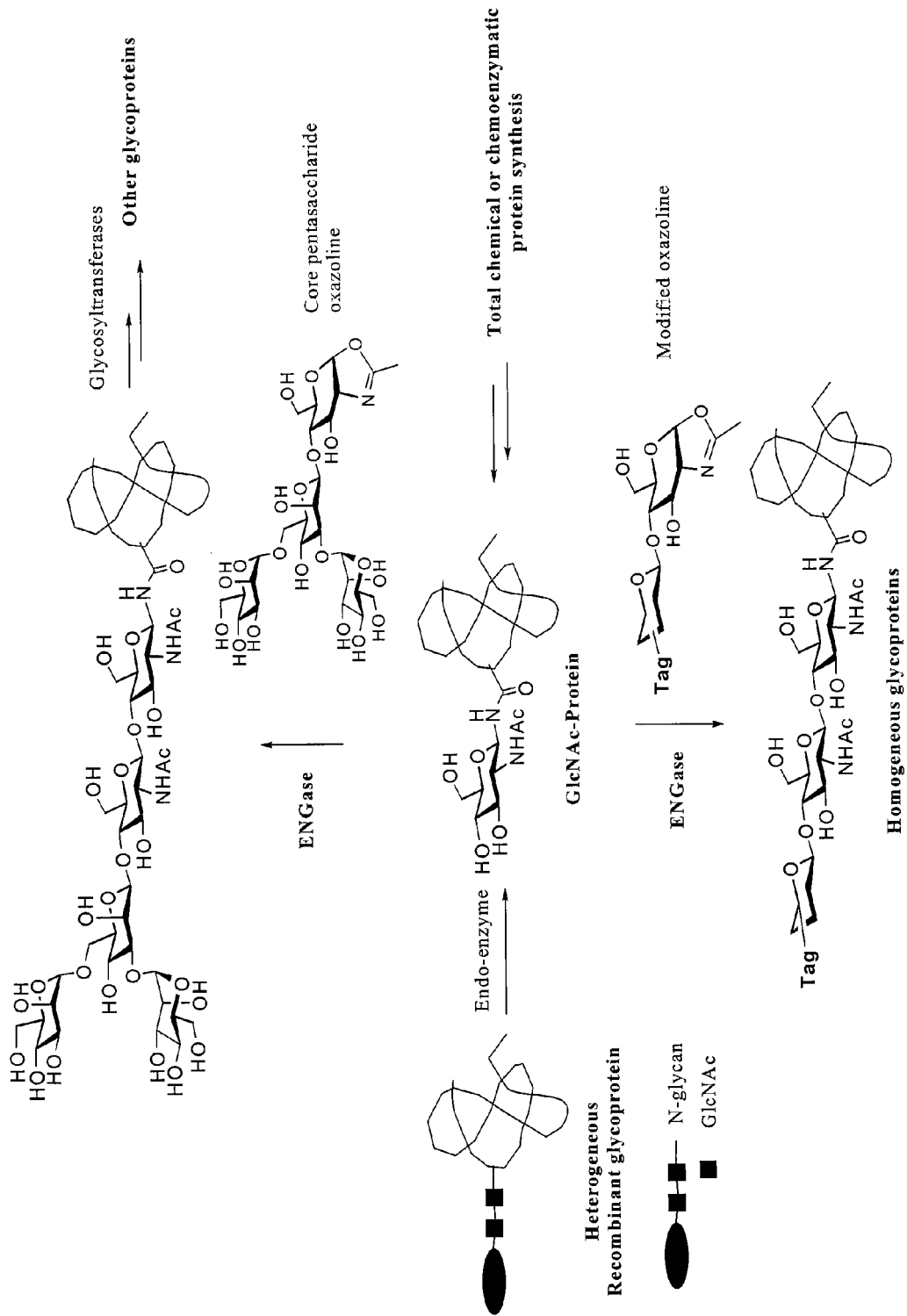
FIG. 1 shows a glycoprotein synthesis scheme and remodeling involving enzymatic transglycosylation.

FIG. 1 shows a glycoprotein synthesis scheme and remodeling involving enzymatic transglycosylation.

In this scheme, a heterogeneous recombinant glycoprotein is converted by endo-enzymatic action to a corresponding GlcNAc-protein. The GlcNAc-protein then can be converted by ENGase with a modified oxazoline to produce homogeneous glycoproteins. The modified oxazoline may be tagged with a suitable tagging moiety (Tag-) to produce a corresponding tagged homogeneous glycoprotein.

As another synthetic path shown in the scheme of FIG. 1, the GlcNAc-protein can be converted by ENGase in the presence of a core pentasaccharide oxazoline to produce a corresponding glycoprotein that then can be converted by glycosyltransferases to form other glycoproteins.

As another synthetic path shown in the scheme of FIG. 1, the GlcNAc-protein can be converted by ENGase in the presence of other natural or modified oligosaccharide oxazolines directly to produce a corresponding glycoprotein with a defined oligosaccharide moiety.

Figure 2:
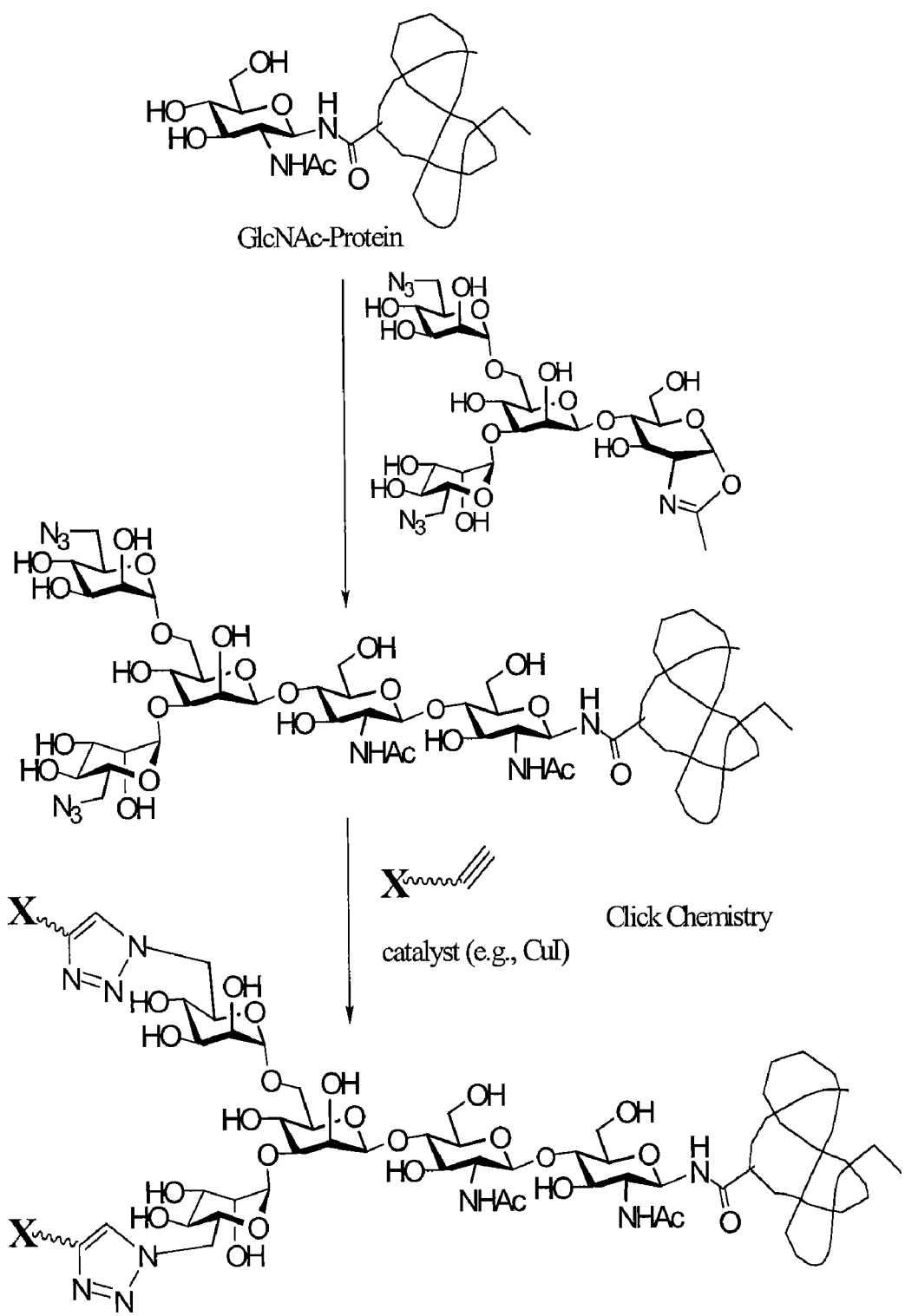
FIG. 2 is a preparative scheme for functionalized glycoproteins, according to one embodiment of the invention.

FIG. 2 is a preparative scheme for functionalized glycoproteins, according to one embodiment of the invention. In this scheme, a GlcNAc-protein is enzymatically converted in reaction with a core pentasaccharide oxazoline to form an intermediate glycoprotein. The intermediate glycoprotein then is catalytically reacted in a "click chemistry" cycloaddition reaction of the azide functionality of the glycoprotein with an alkyne bearing the functional moiety X of interest (Xvvvvvvv≡). X can be any functional moiety, including, without limitation, moieties such as antigens (e.g., alpha-Gal oligosaccharide), therapeutic drugs, toxins, fluorescent probes, biotin, PEG species, lipids, nucleotides, etc. The azido and alkyne functional groups can be switched in the respective ligation components, and the glycoprotein can be functionalized with an alkynyl functionality and reacted with an azide-functionalized compound including the moiety of interest. It will also be appreciated that other ligation pairs can be devised for the click chemistry reaction.

Figure 3:
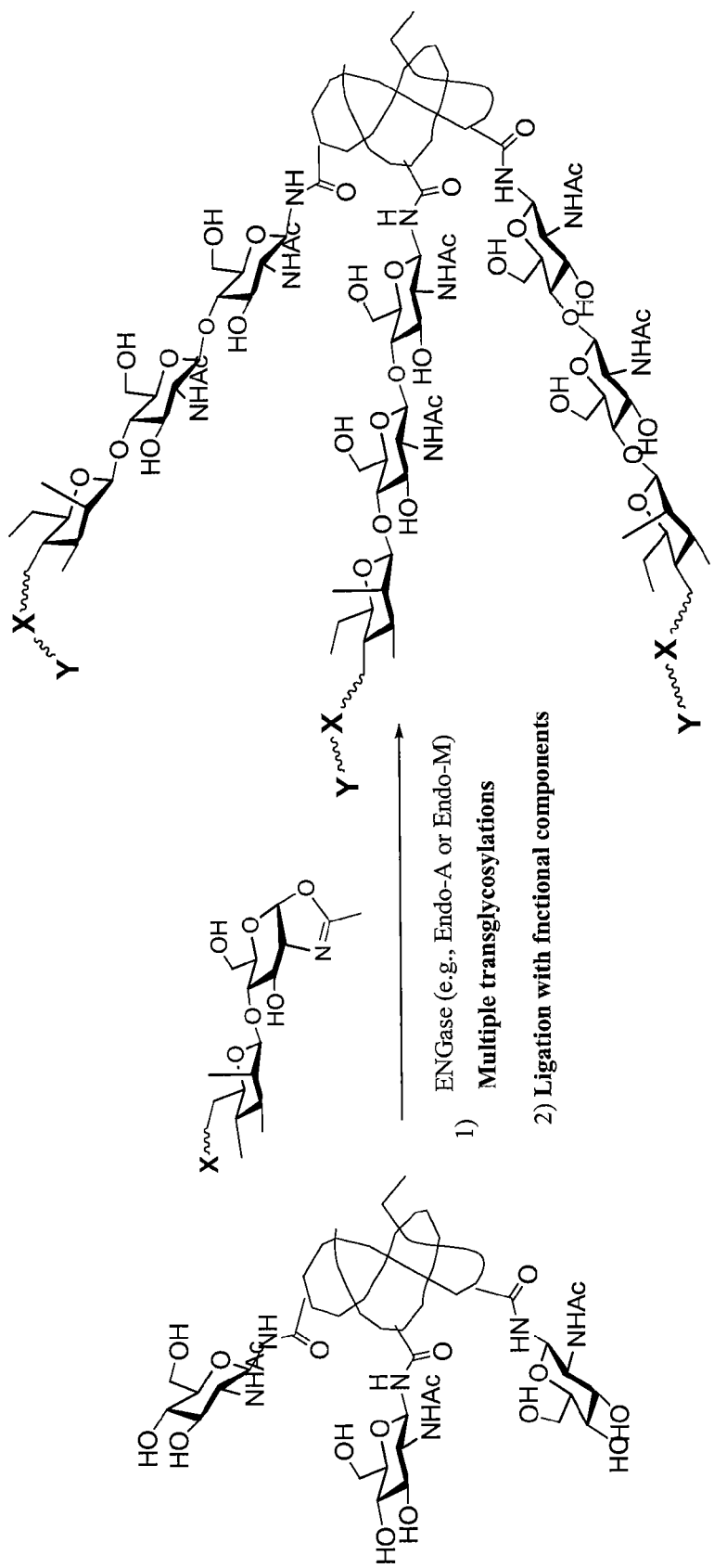
FIG. 3 shows a scheme for remodeling of glycoproteins containing multiple N-glycans.

FIG. 3 shows a scheme for remodeling of glycoproteins containing multiple N-glycans, in which the glycoprotein, e.g., EPO, is remodeled by multiple transglycosylations involving ENGase such as Endo-A or Endo-M, and submitted to ligation with functional components, to enhance in vivo activity by prolonging serum half-life of the glycoprotein product. The functional components can be of any suitable types, including for example, PEGs, multiple anionic species such as carboxylic or multiple sialic acid residues, etc.

Figure 4:
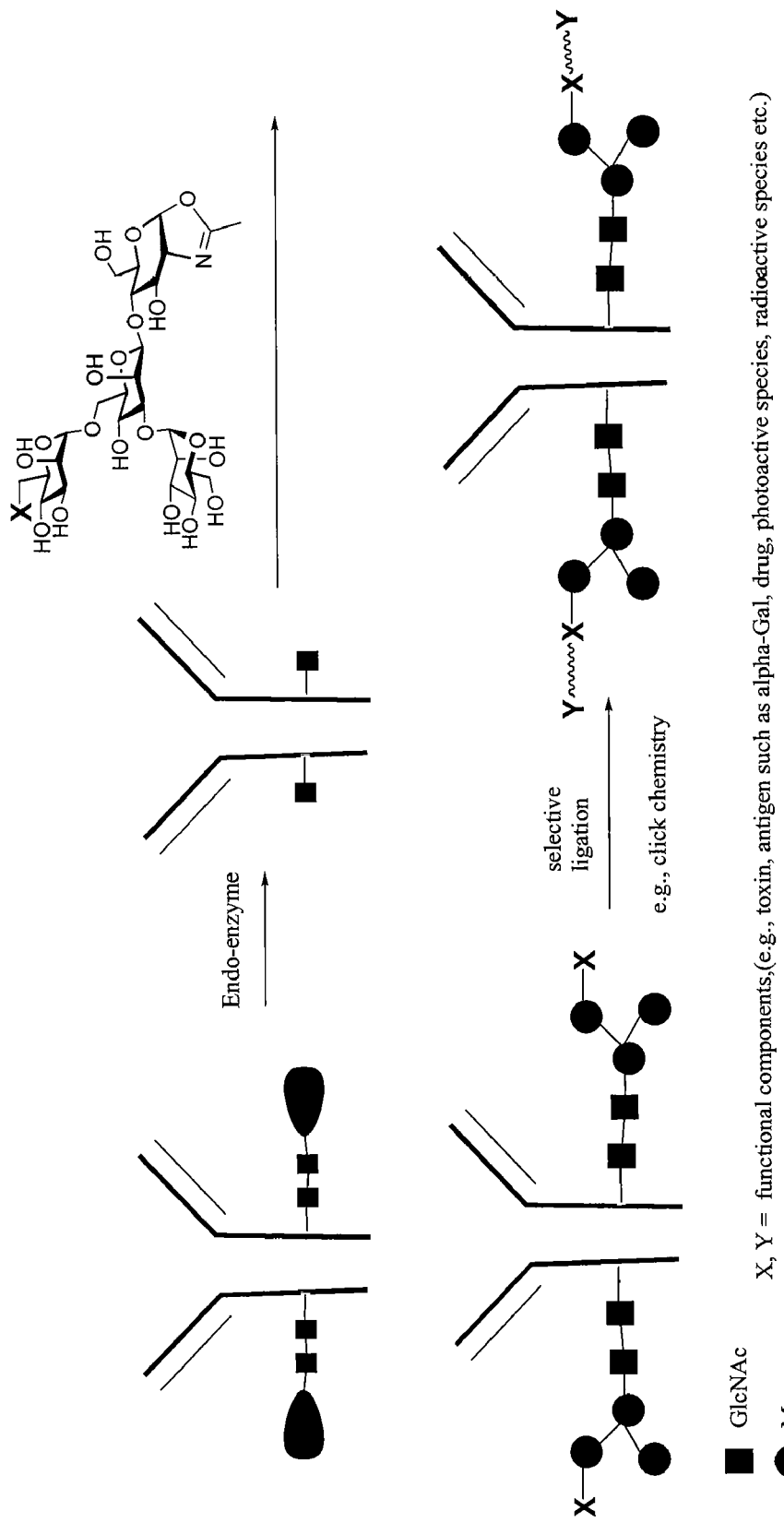
FIG. 4 shows a scheme for antibody glycosylation remodeling to prepare functionalized antibodies.

FIG. 4 shows a scheme for antibody glycosylation remodeling to prepare functionalized antibodies, in which the antibody is converted by an endo-enzyme to an intermediate that is subjected to transglycosylation followed by selective ligation, e.g., involving click chemistry reaction. In this reaction scheme, ■ is GlcNAc, ● is mannose, and X and Y are functional components, such as antigens (e.g., alpha-Gal), toxins, drugs, photoactive species, radioactive species, etc.

In the glycoprotein or glycopeptide remodeling method, the glycoprotein or glycopeptide may contain only one, or more than one, N-glycan, e.g., 2-30 N-glycans. The N-glycans can be of any suitable type. In one embodiment, the attached N-glycans can be high-mannose type, complex type, hybrid type, or combinations including two or more of such types. The attached N-glycans can be either natural or non-naturally-occurring N-glycans, or a combination of such types. When the attached N-glycans include non-naturally-occurring N-glycans, they can have any suitable tags or functional components attached.

The remodeled glycoproteins or glycopeptides can be subjected to any further structural modifications that are necessary or desired, including, without limitation, glycosyl transfer, and selective ligation (e.g., click chemistry, Staudinger reaction, etc.) to introduce functional groups or tags. The functional groups can be of any suitable type, including, without limitation, toxins, special antigens (such as alpha-Gal), radioactive species, photoactive species, PEGs, etc.

The invention thus provides a general method for total glycoprotein or glycopeptide synthesis, in which the GlcNAc is prepared by total protein/peptide synthesis, native chemical ligation, and/or expressed protein ligation. The pre-assembled GlcNAc-protein or GlcNAc-peptide then serves as the acceptor for the enzymatic transglycosylation for the attachment of desired N-glycans. As before, any number of N-glycans can be present in the synthetic glycoprotein or glycopeptide.

The GlcNAc residue can be at native glycosylation sites or any other desired sites. Such sites can be intentionally inserted at specific positions during the synthesis of a precursor.

The invention in another aspect provides an efficient method for antibody (IgG, Fab, etc.) glycosylation remodeling as shown in FIG. 4. Antibodies have two heavy chains, and each heavy chain carries an N-glycan on the $CH_2$ domain of the Fc region. The N-glycans are generally restricted to biantennary oligosaccharides with various (heterogeneous) terminal modifications.

The antibody glycosylation remodeling includes removing the heterogeneous sugar chain by a endoglycosidase (e.g., Endo-F or Endo-M) treatment to remove the N-glycan but leave only a single GlcNAc attached to the original glycosylation site. A core oligosaccharide with a tag or tags then is transferred to the GlcNAc by ENGase-catalyzed transglycosylation to form the correspondingly tagged antibody. Functional components can then be introduced by a selective ligation (such as click chemistry and Staudinger reaction) to produce a customized antibody for various applications.

The functional components attached in the antibody can be of any suitable type, including, without limitation, toxins, special antigens (such as alpha-Gal), radioactive species, photoactive species, PEGs, etc., which can be used for drug delivery, specific targeting, etc.

The features and advantages of the present invention are more fully shown by the following non-limiting examples.

EXAMPLES

Figure 5:
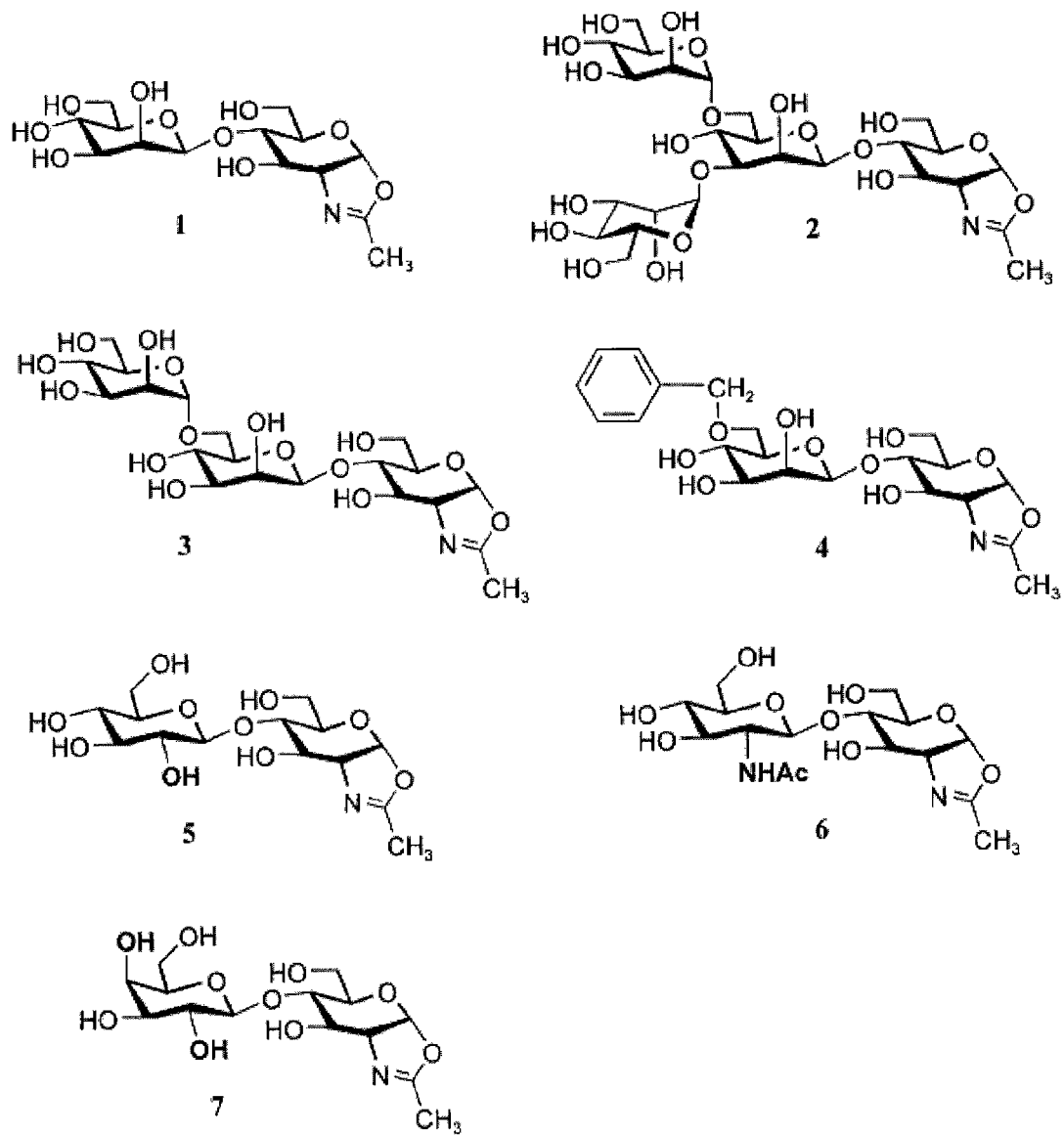
FIG. 5 shows a structures of oligosaccharide oxazoline derivatives.

To further explore the potential of this promising chemoenzymatic method, the synthesis and evaluation of an array of oligosaccharide oxazolines was conducted. As shown in FIG. 5, multiple oligosaccharide oxazolines were prepared by the synthesis scheme shown in FIG. 6 The different oxazolines were used as donor substrates for glycopeptide synthesis were prepared to probe the substrate requirement for the Endo-A catalyzed transglycosylation and to further explore the potential of the chemoenzymatic method for constructing both natural and modified N-glycopeptides.

Figure 6:
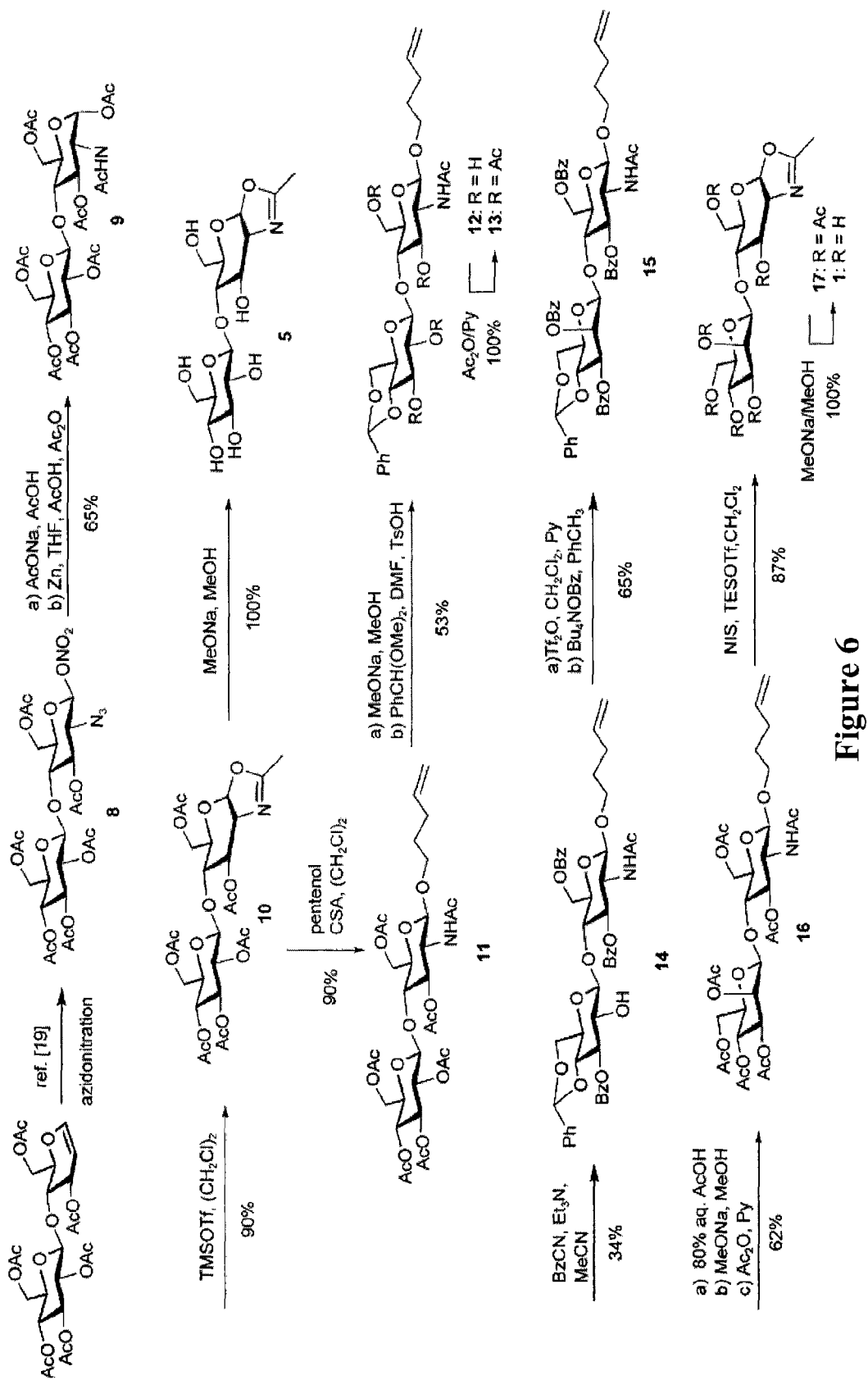
FIG. 6 shows the scheme for synthesis of disaccharide oxazolines.

Synthesis of some oligosaccharide oxazolines as shown in FIG. 6: The Manβ1→4GlcNAc moiety is a core disaccharide of N-glycans. This core disaccharide moiety was previously synthesized through stereocontrolled glycosylation of monosaccharides [11, 14, 18] Here we describe an alternative synthesis of the Manβ1→4GlcNAc core disaccharide and related derivatives using the readily available disaccharide 2,3,4,6-tetra-O-acetyl-β-D-glucopyranosyl-(1→4)-3,6-di-O-acetyl-D-glucal19] as the starting material, which can be easily prepared from cellobiose on a large scale. The synthesis started with an azidonitration [20] of the cellobiose glycal to obtain the known 2-azido-2-deoxy-cellobiose derivative 8. [19] Acetolysis of the isolated β-nitrate 8 with sodium acetate in acetic acid, followed by reduction of the azide to acetamido group with zinc dust in the presence of acetic anhydride, gave the 2-acetamido-2-deoxy-cellobiose derivative 9 in 65% yield. Treatment of compound 9 with TMSOTf [21] resulted in the formation of per-O-acetylated oxazoline derivative 10 (90%), which was de-O-acetylated with catalytic amount of MeONa in MeOH to give the oxazoline 5. To synthesize the Manβ1→4GlcNAc core disaccharide and its derivatives, the configuration at C-2' needs to be converted from the gluco-type to the manno-type. This was achieved by a series of selective transformations. First, a 4-pententyl group was introduced at the anomeric position of the disaccharide moiety, which could be directly transformed to an oxazoline moiety in the later stage by a one-step oxazoline formation reaction. [18] Thus treatment of 10 with 4-penten-1-ol under the catalysis of 10-camphorsulfonic acid (CSA) gave pentenyl 2-acetamido-β-glycoside 11 (90%). De-O-acetylation of 11, followed by subsequent benzylidenation, gave compound 12 (53%). Selective benzoylation [22] of 12 with BzCN in MeCN at low temperature gave compound 14 in 34% isolated yield, which has a free hydroxyl group at the 2'-position. The inversion of the C-2' configuration was achieved by following the previously described $S_N2$ inversion of the C-2 configuration for β-mannoside synthesis. [22, 23] Thus, triflation of compound 14 with triflic anhydride/pyridine, followed by $S_N2$ substitution with benzoate, gave the protected Manβ1→4GlcNAc disaccharide derivative 15 in 65% yield in two steps. Compound 15 was converted to the O-acetylated derivative 16, which was then modified to yield oxazoline derivative 17 by treatment with NIS/TESOTf. [18] Finally, de-O-acetylation of 17 gave disaccharide oxazoline 1

Synthesis of Disaccharide Oxazolines.

Figure 7:
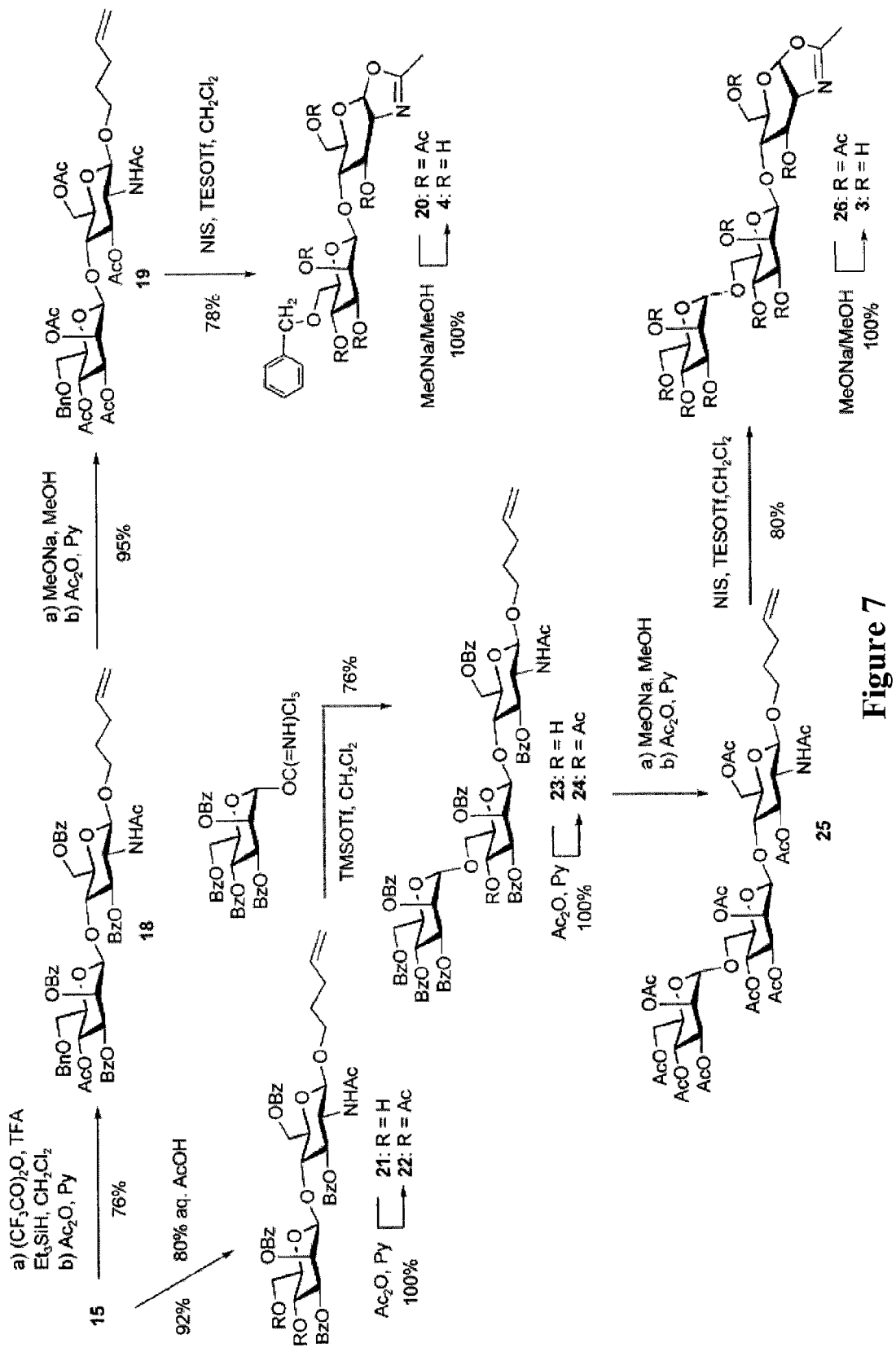
FIG. 7 shows the scheme for synthesis of modified oxazolines derivatives

The 6'-modified disaccharide oxazoline 4 was prepared from compound 15 in several steps as shown in FIG. 7. Selective reductive ring-opening of the benzylidene group in 15 by treatment with $Et_3SiH$/TFA/trifluoroacetic anhydride/ $CH_2Cl_2$[24] gave compound 18, with a benzyl group attached to the 6'-O-position. The benzoyl groups were then replaced by acetyl groups to give compound 19. Treatment of 19 with NIS/TESOTf resulted in the formation of oxazoline derivative 20 (78%), which was de-O-acetylated to give 6'-O-benzyl disaccharide oxazoline 4.

Synthesis of Modified Oxazoline Derivatives.

To prepare trisaccharide oxazoline 3, the 4',6'-O-benzylidene group in 15 was selectively removed by treatment with 80% aqueous AcOH at 50° C. The resulting compound 21 was then selectively glycosylated at the 6'-OH position with 2,3,4,6-tetra-O-benzoyl-β-D-mannopyranosyl trichloroacetimidate under the catalysis of TMSOTf to give trisaccharide derivative 23 (76%). De-O-benzoylation of 23 with subsequent O-acetylation afforded the O-acetylated pentenyl glycoside 25. Finally, compound 25 was converted to the oxazoline derivative by treatment with NIS/TESOTf to give 26, which was de-O-acetylated to provide trisaccharide oxazoline 3. On the other hand, the known chitobiose oxazoline 6 [15] and the LacNAc-oxazoline 7 [16] were prepared from O-acetylated N,N'-diacetylchitobiose and N-acetyllactosamine, respectively, following the reported procedure. [15, 16]

Endo-A Catalyzed Transglycosylation of the Synthetic Oxazolines with GlcNAc-Peptides:

To test the transglycosylation potential of the synthetic oligosaccharide oxazolines, a small GlcNAc-tripeptide acceptor, Asn(GlcNAc)-Ile-Thr was synthesized, which represents the minimum consensus sequence for the N24 and N38 N-glycosylation sites in erythropoietin, an important therapeutic glycoprotein for the treatment of anemia. [25] Notably, the disaccharide oxazoline 1 and tetrasaccharide oxazoline 2 are good donor substrates for Endo-A. [11] As expected, the Endo-A catalyzed reaction of oxazolines 1 and 2 with the GlcNAc-peptide 27 (donor/acceptor 3:1) proceeded smoothly in a phosphate buffer (pH 6.5) to give the corresponding N-glycopeptides 28 and 29 in 63 and 86% yields, respectively. Trisaccharide oxazoline 3 was also an efficient donor substrate for the Endo-A catalyzed transglycosylation. Thus incubation of 3 and acceptor 27 (ratio 3:1) in the presence of Endo-A gave glycopeptide 30 carrying the N-linked tetrasaccharide moiety in 72% isolated yield. Interestingly, 6'-O-benzyl disaccharide oxazoline 4, which has an aromatic substituent attached at the 6'-position, could still be recognized by Endo-A as a donor substrate. The Endo-A catalyzed reaction of 4 with acceptor 27 (3:1) afforded the modified glycopeptide 31 in 55% isolated yield.

Figure 8:
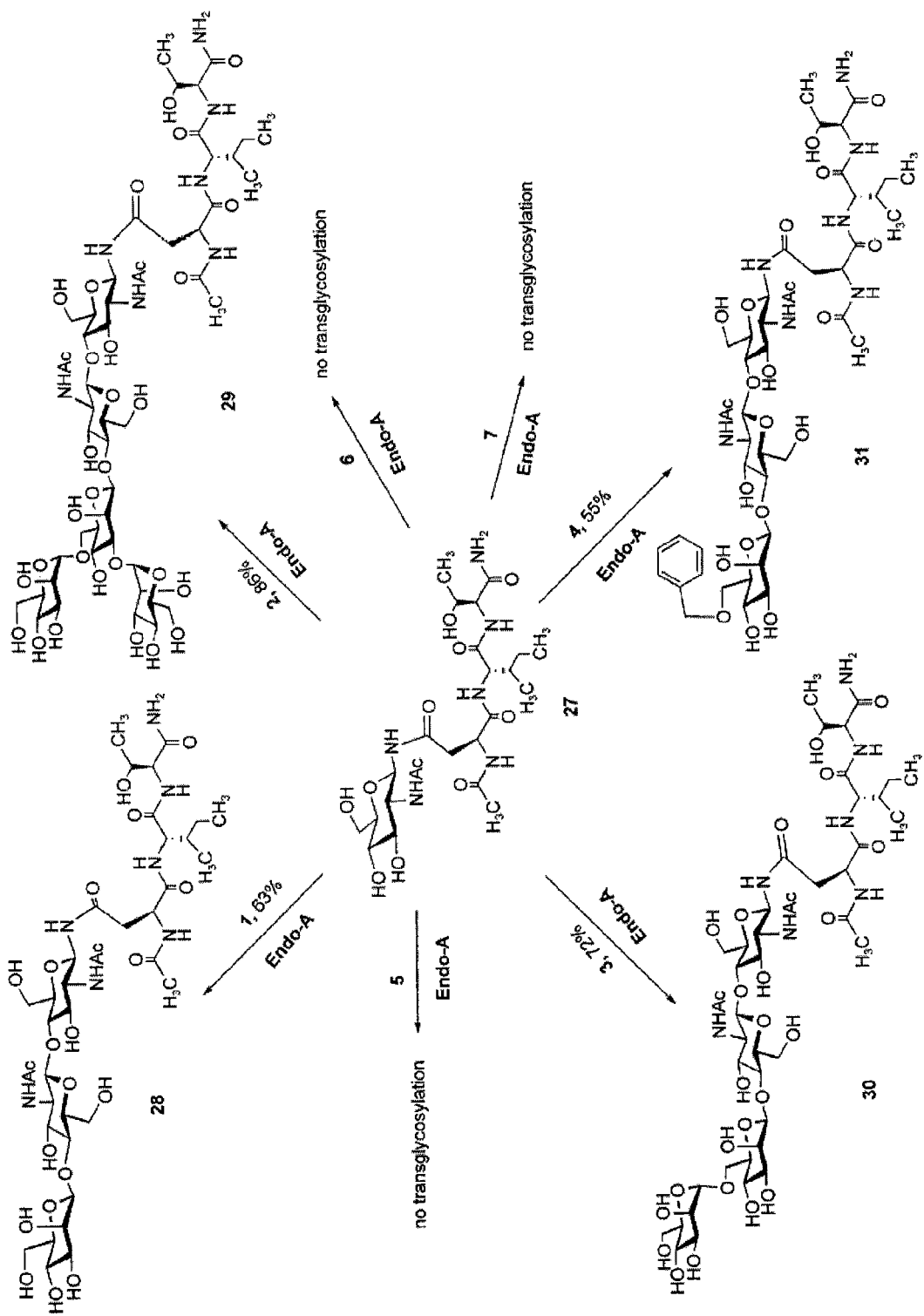
FIG. 8 shows the different synthesis regime for ENGase-catalyzed transglycosylation with different oxazolines.

Although the disaccharide oxazolines 1 and 4 were recognized by Endo-A as donor substrates for the transglycosylation, their reactions were found to proceed more slowly than those reactions of tetrasaccharide oxazoline 2 and trisaccharide oxazoline 3. A quick comparison of the transglycosylation under the same conditions revealed that the relative transglycosylation rates with acceptor 27, s shown in FIG. 8, were in the following order: tetrasaccharide oxazoline 2>trisaccharide oxazoline 3>disaccharide oxazoline 1>Bn-substituted disaccharide oxazoline 4. Although a quantitative comparison of the sugar oxazoline substrates will await detailed enzyme kinetic studies to obtain the kinetic data $K_m$ and $V_{max}$, these results suggest that the attachment of additional β-mannosyl moieties at the 3- and 6-position of the β-mannose core, as present in the natural N-glycans, enhance the enzymatic recognition of the donor substrates. The results also suggested that Endo-A could tolerate modification at the 6'-position of the disaccharide oxazoline, thus allowing the synthesis of modified glycopeptides. In all cases, the newly formed glycosidic bond in the resulting glycopeptides 28, 29, 30, and 31 was determined by 2D NMR analysis (data not shown) to be a β-1,4-glycosidic linkage, confirming the previous conclusion that the Endo-A catalyzed transglycosylation using oligosaccharide oxazoline as the donor substrates proceeded in a regio- and stereospecific manner. [11] It was observed that Endo-A could slowly hydrolyze the oxazolines 1-4 but, in the presence of a GlcNAc-peptide acceptor, the transglycosylation was found to be faster than the hydrolysis. The results suggest that the GlcNAc moiety is a better acceptor than water molecule in the Endo-A catalyzed reaction.

Next, the structurally related disaccharide oxazolines 5-7 were tested. Cellobiose-oxazoline 5, which differs from Manβ-1,4GlcNAc-oxazoline 1 only by the configuration of the C'-2 hydroxyl group, was inactive in the enzymatic transglycosylation. Similarly, chitobiose-oxazoline 6 and LacNAc-oxazoline 7, which were substrates of Bacillus chitinase, [15, 16] could not be recognized by Endo-A. These results indicate that the structure of the core β-mannose moiety is required for Endo-A recognition. Replacement of the β-Man moiety in the disaccharide oxazoline substrate 1 with β-Glc, β-GlcNAc, and β-Gal moiety, respectively, resulted in total loss of its substrate activity. The experiments revealed that the Manβ1→4GlcNAc oxazoline moiety is the minimum structure that is recognized by the enzyme Endo-A for transglycosylation. Despite this, the enzyme could tolerate selective modification on the mannose moiety, for example, attachment of additional sugar moieties at the 3',6'-positions and even an aromatic group at the 6"-position.

Figure 9:
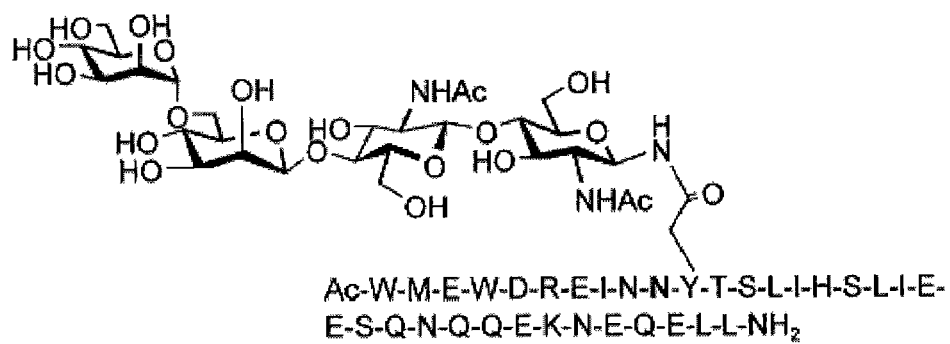
FIG. 9 shows the synthesis of glycoforms of gp41 C-peptide C34.
Figure 9:
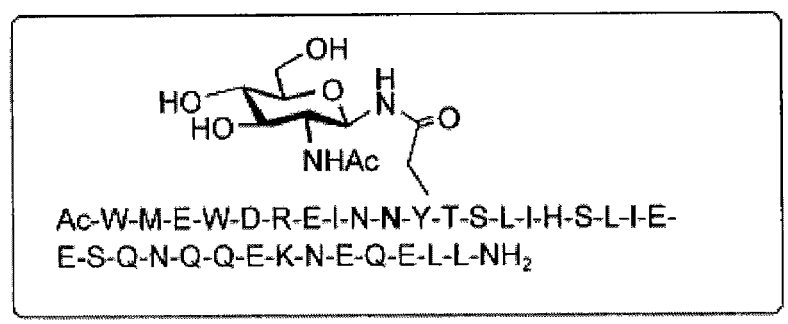
Figure 9:
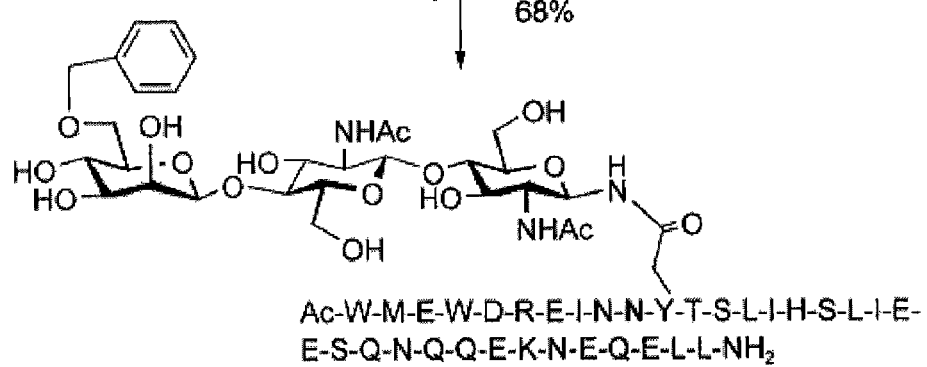

In the present study, it was found that the enzymatic transglycosylation of trisaccharide-oxazoline 3 and modified disaccharide oxazoline 4 to the large acceptor GlcNAc-C34 also proceeded successfully, as shown in FIG. 9. This led to the synthesis of the large glycopeptide 32 that contains the core N-linked tetrasaccharide (75% yield) and glycopeptide 33 which carries a modified trisaccharide (68%) when an excess oxazoline donor (donor/acceptor 5:1) was used. The relatively high-yield transglycosylation suggests that the Endo-A catalyzed transglycosylation of the sugar oxazolines was equally efficient for small and large acceptors. Finally, we also tested whether Endo-A could hydrolyze the resulting "ground-state" glycopeptides 28-33 carrying the N-linked core tri-, tetra-, and pentasaccharide, respectively. It was found that in the presence of large amount of Endo-A, only glycopeptide 29 that carries the core pentasaccharide was slowly hydrolyzed by Endo-A to release the tetrasaccharide Manα1→6(Manα1→3)Manβ1→4GlcNAc (Man$_3$GlcNAc) and the GlcNAc-peptide moiety. The other glycopeptides carrying the core tri- and tetrasaccharides 28, 30, 32, as well as those carrying the modified trisaccharide 31 and 33, were resistant to the enzymatic hydrolysis. Considering that the corresponding di-, tri-, and tetrasaccharide oxazolines 1-4 are active for the enzymatic transglycosylation, the results suggest that the sugar oxazolines as donor substrates are kinetically more favorable for the transglycosylation than the hydrolysis of the resulting ground-state glycopeptides, allowing product accumulation.

An array of oligosaccharide oxazolines was synthesized and evaluated as donor substrates for the Endo-A catalyzed glycopeptide synthesis. It was revealed that the minimum substrate structure required for the Endo-A catalyzed transglycosylation is a Manβ1→4GlcNAc oxazoline moiety. Despite this, the enzyme can tolerate modifications at the 3'- and/or 6'-positions of the disaccharide oxazoline, allowing the transfer of both larger and selectively modified oligosaccharide moieties to the peptide acceptor. On the other hand, the enzyme has a great flexibility for the acceptor portion and could efficiently take both small and large GlcNAc-peptide as the acceptor substrate. Since this high-yield enzymatic ligation allows independent manipulations of the donor (sugar oxazoline) and the acceptor (GlcNAc-peptide/protein) portions by well-established oligosaccharide and peptide chemistry, it provides a highly convergent approach for constructing both natural and modified glycopeptides.

The glycopeptides described in FIGS. 5 to 9 were synthesized according to the following general procedures: TLC was performed on aluminum plates coated with silica gel 60 with detection by charring with 10% (v/v) sulfuric acid in methanol or by UV detection. Flash column chromatography was performed on silica gel 60 (EM Science, 230-400 mesh). $^1$H and $^{13}$C NMR, and 2D NMR spectra were recorded on Inova 500 NMR in $CDCl_3$, $D_2O$, or $CD_3OD$, as specified. Chemical shifts are expressed in ppm downfield using external $Me_4Si$ (0 ppm) as the reference. The ESI-MS spectra were measured on a micromass ZQ-400 single quadruple mass spectrometer. Analytic HPLC was carried out with a Waters 626 HPLC instrument on a Waters NovaPak C18 column (3.9×150 mm) at 40° C. The column was eluted with a linear gradient of 0-90% MeCN containing 0.1% TFA at a flow rate of 1 mL min$^{-1}$ over 25 min. Peptide and glycopeptides were detected at two wavelengths (214 and 280 nm). Preparative HPLC was performed with Waters 600 HPLC instrument on a Waters C18 Column (symmetry 300, 19×300 mm). The column was eluted with a suitable gradient of MeCN containing 0.1% TFA at 12 mL min$^{-1}$.

O-(2,3,4,6-Tetra-O-acetyl-β-D-glucopyranosyl)-(1→4)-2-acetamido-1,3,6-tri-O-acetyl-2-deoxy-α-D-glucopyranose (9): A suspension of 8 (15 g, 22.5 mmol) [19] and anhydrous NaOAc (20 g) in AcOH (250 mL) was heated to 100° C. for 1 h. The reaction was diluted with EtOAc and washed with $NaHCO_3$ and brine, dried by $Na_2SO_4$, and filtered. The filtrate was concentrated in vacuo to give a white solid. The solid was dissolved in THF (100 mL) and AcOH (50 mL). To the solution were sequentially added $Ac_2O$ (10 mL) and zinc dust (30 g) in portions. The mixture was stirred at RT for 1 h and filtered through a Celite pad. The filtrate was concentrated in vacuo and the residue was subject to flash column chromatography (hexanes/EtOAc 1:2) to give 9 (9.94 g, 65%). $^1$H NMR (500 MHz, $CDCl_3$): δ=6.09 (d, J=3.5 Hz, 1H, H-1), 5.72 (d, J=8.5 Hz, 1H, NH), 5.21 (dd, J=8.8, 10.5 Hz, 1H, H-3), 5.15 (t, J=9.0 Hz, 1H, H-3'), 5.08 (t, J=9.0 Hz, 1H, H-4'), 4.93 (t, J=9.0 Hz, 1H, H-2'), 4.55 (d, J=8.4 Hz, 1H, H-1'), 4.44-4.35 (m, 3H), 4.12-4.04 (m, 2H), 3.88-3.82 (m, 2H), 3.70-3.66 (m, 1H), 2.19, 2.12, 2.09, 2.06, 2.04, 2.01, 1.99, 1.95 (s each, 3H each, 8$CH_3CO$); ESI-MS: m/z: calcd for $C_{28}H_{39}NO_{18}$: 677.22; found: 678.34 [M+H]$^+$.

O-(2,3,4,6-Tetra-O-acetyl-β-D-glucopyranosyl)-(1→4)-2-acetamido-3,6-di-O-acetyl-1,2-dideoxy-α-D-glucopyrano)-[2,1-d]-2-oxazoline (10): TMSOTf (3.2 mL, 1.1 equiv) was added under argon atmosphere to a solution of 9 (10.8 g, 16 mmol) in dry $ClCH_2CH_2Cl$. The mixture was stirred at 50° C. overnight. After cooling to RT, the mixture was neutralized by $Et_3N$ and concentrated. The residue was subjected to a flash column chromatography (hexanes/EtOAc 1:2) to afford 10 (8.85 g, 90%). $^1$H NMR (500 MHz, $CDCl_3$): δ=5.90 (d, J=7.3 Hz, 1H, H-1), 5.64 (d, J=1.8 Hz, 1H, H-3), 5.16 (t, J=9.2 Hz, 1H, H-3'), 5.11 (t, J=9.8 Hz, 1H, H-4'), 5.00 (t, J=8.4 Hz, 1H, H-2'), 4.70 (d, J=8.4 Hz, 1H, H-1'), 4.37-4.09 (m, 5H), 3.79-3.76 (m, 1H, H-5), 3.63-3.62 (m, 1H), 3.48-3.45 (m, 1H, H-5'), 2.10, 2.09, 2.08, 2.08, 2.03, 2.00, 1.98 (s each, 3H each, 7$CH_3$); $^{13}$C NMR ($CDCl_3$, 125 MHz): δ=169.8, 169.7, 169.4, 168.5, 165.9, 101.2, 98.1, 77.2, 72.1, 71.1, 70.4, 69.2, 67.1, 66.6, 63.9, 62.6, 60.9, 13.0; ESI-MS: m/z: calcd for $C_{26}H_{35}NO_{16}$: 617.2; found: 618.43 [M+H]$^+$.

O-(β-D-Glucopyranosyl)-(1→4)-1,2-dideoxy-α-D-glucopyrano)-[2,1-d]-2-oxazoline (5): A solution of 10 (12 mg, 19 μmol) in MeOH containing NaOMe (2 μmol) was stirred at RT for 2 h. Then the mixture was concentrated in vacuo. The residue was dissolved in water and lyophilized to give oxazoline 5 (6 mg, quantitative) as a white solid. $^1$H NMR ($CD_3OD$, 500 MHz): δ=6.03 (d, J=7.0 Hz, 1H, H-1), 4.66 (d, J=7.5 Hz, 1H, H-1'), 4.32 (s, 1H, H-2), 4.13 (dd, J=7.5, 8.4 Hz, 1H, H-2'), 3.91-3.88 (m, 4H), 3.72-3.50 (m, 12H), 3.55-3.32 (m, 3H), 1.85 (s, 3H, $CH_3$); $^{13}$C NMR ($CD_3OD$, 125 MHz): δ=168.6, 101.2, 99.9, 77.4, 76.4, 72.8, 70.9, 70.4, 69.3, 66.8, 65.2, 61.7, 61.1, 13.0; ESI-MS: m/z: calcd for $C_{14}H_{23}NO_{10}$: 365.13; found: 366.87 [M+H]$^+$.

4-Pentenyl O-(2,3,4,6-tetra-O-acetyl-β-D-glucopyranosyl)-(1→4)-3,6-di-O-acetyl-2-acetamido-2-deoxy-β-D-glucopyranoside (11): 4-Penten-1-ol (10 mL, 53 mmol) and CSA (300 mg) was added to a solution of 10 (8.85 g, 14.3 mmol) in anhydrous $ClCH_2CH_2Cl$ (80 mL). The mixture was stirred under an argon atmosphere at 90° C. for 2 h. After cooling to RT, the mixture was neutralized by $Et_3N$ and concentrated. The residue was subjected to flash column chromatography (hexanes/EtOAc 1:3) to afford 11 (9.1 g, 90%) as an amorphous solid. $^1$H NMR (500 MHz, $CDCl_3$): δ=5.83-5.75 (m, 2H, —CH=, NH), 5.18 (t, J=9.0 Hz, 1H), 5.12-4.95 (m, 5H), 4.57-4.54 (m, 2H), 4.45 (d, J=8.0 Hz, 1H, H-1'), 4.39 (dd, J=12.0, 4.5 Hz, 1H), 4.16-4.02 (m, 4H), 3.87-3.69 (m, 6H), 3.64-3.61 (m, 1H), 3.50-3.45 (m, 3H), 2.14, 2.11, 2.08, 2.06, 2.04, 2.01, 1.98 (s each, 3H each, 7$CH_3CO$), 1.75-1.64 (m, 2H, —$OCH_2CH_2CH_2$—); $^{13}$C NMR ($CDCl_3$, 125 MHz): δ=169.9, 169.6, 169.5, 169.3, 169.2, 168.5, 168.4, 137.0, 114.0, 100.1, 99.8, 75.3, 71.9, 71.7, 71.4, 71.0, 70.7, 67.9, 66.9, 61.3, 60.7, 52.5, 29.01, 19.9, 19.8, 19.7, 19.6; ESI-MS: m/z: calcd for $C_{31}H_{45}NO_{17}$: 703.27; found: 704.07 [M+H]$^+$.

4-Pentenyl O-(4,6-O-benzylidene-β-D-glucopyranosyl)-(1→4)-2-acetamido-2-deoxy-β-D-glucopyranoside (12) and 4-pentenyl O-(2,3-di-O-acetyl-4,6-O-benzylidene-β-D-glucopyranosyl)-(1→4)-3,6-di-O-acetyl-2-acetamido-2-deoxy-β-D-glucopyranoside (13): A solution of the compound 11 (9 g, 13 mmol) in MeOH (100 mL) containing NaOMe (1.3 mmol) was stirred at RT for 2 h. Then the mixture was neutralized by Dowex W50-X8 (H$^+$ form), filtered, and the filtrate was concentrated. The residue was dissolved in DMF (50 mL) and dimethyl acetal benzaldehyde (6.3 mL, 3.4 equiv) and p-toluenesulfonic acid (1.0 g). The mixture was stirred at 50° C. for 10 h. After cooling to RT, the mixture was neutralized by $Et_3N$ and concentrated. The residue was subjected to flash column chromatography (EtOAc/MeOH 10:1) to give 12 (3.65 g, 53%). ESI-MS: m/z: calcd for $C_{26}H_{37}NO_{11}$: 539.24; found: 540.35 [M+H]$^+$.

The compound was further characterized by transformation to its acetylated derivative 13. To a solution of 12 (50 mg) in pyridine (2 mL) was added $Ac_2O$ (0.2 mL). The mixture was stirred at RT for 5 h. The mixture was then poured into cold $NaHCO_3$ solution and stirred for 2 h at RT. The mixture was extracted with $CH_2Cl_2$ and the organic layer washed with $NaHCO_3$, HCl (1 n) and brine, dried by $Na_2SO_4$, and filtered. The filtrate was concentrated in vacuo and the residue was subjected to flash column chromatography (hexanes/EtOAc 2:1) to give 13 (72 mg, quantitative) as a white foam. $^1$H NMR (500 MHz, $CDCl_3$): δ=7.51-7.32 (m, 5H, $C_6H_5$), 5.84-5.78 (m, 2H, —CH=, NH), 5.53 (s, 1H, PhCH=), 5.32 (t, J=9.5 Hz, 1H), 5.12 (t, J=9.2 Hz, 1H), 5.06-4.95 (m, 3H), 4.66 (d, J=7.5 Hz, 1H, H-1), 4.55-4.39 (m, 3H), 4.16-4.04 (m, 2H), 3.88-3.71 (m, 5H), 3.64-3.63 (m, 2H), 3.55-3.46 (m, 3H), 2.16, 2.10, 2.08, 2.06, 2.00 (s each, 3H each, 5$CH_3CO$), 1.75-1.66 (m, 2H, —$OCH_2CH_2CH_2$—); ESI-MS: m/z: calcd for $C_{34}H_{45}NO_{15}$: 707.28; found: 708.58 [M+H]$^+$.

4-Pentenyl O-(3-O-benzoyl-4,6-O-benzylidene-β-D-glucopyranosyl)-(1→4)-3,6-di-O-benzoyl-2-acetamido-2- deoxy-β-D-glucopyranoside (1→4): BzCN (2.6 mL, 3.3 equiv) in MeCN (25 mL) was added at −30° C. in portions over 3 h to a solution of 12 (3.3 g, 61 mmol) in MeCN (50 mL) containing Et$_3$N (3 mL). The reaction was monitored by TLC (hexanes/EtOAc 2:1). After stirring at −30° C. for 5 h, the reaction was quenched by adding MeOH. The mixture was diluted with EtOAc, washed with 0.1 M HCl, NaHCO$_3$ and brine, dried over Na$_2$SO$_4$, and filtered. The filtrate was concentrated in vacuo and the residue was subject to flash silica gel column chromatography (hexanes/EtOAc 2:1) to give 14 (1.77 g, 34%) as a white foam. $^1$H NMR (500 MHz, CDCl$_3$): δ=8.20-7.26 (m, 20H, C$_6$H$_5$), 6.33 (d, J=8.5 Hz, 1H, NH), 5.75-5.69 (m, 1H, —CH═), 5.64 (dd, J=9.5, 2.0 Hz, 1H, H-3), 5.28 (t, J=9.2 Hz, 1H, H-3'), 5.14 (s, 1H, PhCH═), 5.01-4.87 (m, 3H), 4.80 (d, J=8.5 Hz, 1H, H-1), 4.63-4.60 (m, 2H), 4.20-4.15 (m, 1H), 4.05-4.03 (m, 2H), 3.95-3.94 (d, J=4.5 Hz, 1H), 3.86-3.81 (m, 2H), 3.69-3.65 (m, 1H), 3.55-3.51 (m, 1H), 3.44 (t, J=9.0 Hz, 1H, H-4'), 3.35 (dd, J=10.5, 4.8 Hz, 1H), 3.21-3.16 (m, 1H), 2.87 (t, J=10.5 Hz, 1H), 2.06-2.03 (m, 2H, —OCH$_2$CH$_2$CH$_2$—), 1.83 (s, 3H, CH$_3$CO), 1.68-1.59 (m, 2H, —OCH$_2$CH$_2$CH$_2$—); ESI-MS: m/z: calcd for C$_{47}$H$_{49}$NO$_{14}$: 851.32; found: 852.42 [M+H]$^+$.

4-Pentenyl O-(2,3-di-O-benzoyl-4,6-O-benzylidene-β-D-mannopyranosyl)-(1→4)-3,6-di-O-benzoyl-2-acetamido-2-deoxy-β-D-glucopyranoside (15): Tf$_2$O (690 μL, 2 equiv) at 0° C. for 1 h was added to a solution of 14 (1.7 g, 19 mmol) in CH$_2$Cl$_2$ (50 mL) containing pyridine (1 mL). The reaction was monitored by TLC. After the completion of the reaction, the mixture was diluted with CH$_2$Cl$_2$, washed successively with cold HCl (0.1 n), cold saturated NaHCO$_3$ and H$_2$O, dried over Na$_2$SO$_4$, and filtered. The filtrate was concentrated and co-evaporated with toluene. The residue was then dissolved in toluene (20 mL) and Bu$_4$NOBz (3 g, 76 mmol) was added. The mixture was stirred under reflux for 2 h when TLC indicated the completion of the reaction. After evaporation, the mixture was diluted with CH$_2$Cl$_2$, washed successively with saturated NaHCO$_3$ and H$_2$O, dried over Na$_2$SO$_4$, and filtered. The filtrate was concentrated in vacuo and the residue was subject to flash silica gel column chromatography (hexanes/EtOAc 1:3) to afford 15 (1.25 g, 65%) as a white foam. $^1$H NMR (500 MHz, CDCl$_3$): δ=8.11-7.26 (m, 25H, 5C$_6$H$_5$), 5.87 (d, J=3.5 Hz, 1H, H-2'), 5.77-5.69 (m, 2H), 5.61 (d, J=9.5 Hz, 1H, NH), 5.45-5.38 (m, 3H), 5.33 (t, J=9.2 Hz, 1H, H-3), 4.97-4.90 (m, 3H), 4.69 (dd, J=12.0, 3.5 Hz, 1H, H-6a), 4.60 (dd, J=12.0, 3.8 Hz, 1H, H-6b), 4.53-4.48 (m, 2H), 4.19-4.14 (m, 2H), 3.99 (t, J=10.0 Hz, 1H, H-4'), 3.79-3.68 (m, 3H), 3.48-3.26 (m, 3H), 2.08-2.02 (m, 2H, —OCH$_2$CH$_2$CH$_2$—), 1.83 (s, 3H, CH$_3$CO), 1.68-1.59 (m, 2H, —OCH$_2$CH$_2$CH$_2$—); $^{13}$C NMR (CDCl$_3$, 125 MHz): δ=170.1, 166.4, 166.3, 165.7, 165.5, 136.0, 133.4, 133.3, 133.1, 130.0, 129.9, 129.8, 128.6, 128.4, 128.2, 126.1, 114.9, 101.7, 101.2, 99.2, 77.4, 77.1, 76.8, 72.8, 70.4, 68.8, 68.0, 67.5, 62.0, 53.7, 30.0, 28.6, 23.3; ESI-MS: m/z: calcd for: C$_{54}$H$_{53}$NO$_{15}$: 955.34; found: 956.37 [M+H]$^+$.

4-Pentenyl O-(2,3,4,6-tetra-O-acetyl-β-D-mannopyranosyl)-(1→4)-3,6-di-O-acetyl-2-acetamido-2-deoxy-β-D-glucopyranoside (16): A solution of 15 (300 mg, 0.31 mmol) in 80% HOAc (10 mL) was stirred at 50° C. for 4 h. The mixture was concentrated in vacuo, and the residue was dissolved in MeOH (20 mL) containing NaOMe (0.03 mmol). The solution was stirred at RT for 5 h and then neutralized with Dowex W50-X8 (H$^+$ form). The solution was filtered, and the filtrate was concentrated to dryness. The residue was then treated with pyridine (5 mL) and Ac$_2$O (1 mL) at RT for 10 h. The reaction mixture was then poured into cold NaHCO$_3$ solution and stirred for 2 h. The reaction mixture was extracted with CH$_2$Cl$_2$ and the organic layer was washed with aq. NaHCO$_3$, HCl (1 n) and brine, dried by Na$_2$SO$_4$, and filtered. The filtrate was concentrated in vacuo and the residue was subject to flash silica gel column chromatography (hexanes/EtOAc 1:3) to give 16 (140 mg, 62%). $^1$H NMR (500 MHz, CDCl$_3$: δ=5.83-5.75 (m, 1H, —CH═), 5.41 (d, J=9.0 Hz, 1H, NH), 5.39 (d, J=3.5 Hz, 1H, H-2'), 5.19 (t, J=9.0 Hz, 1H, H-4'), 5.10 (t, J=9.0 Hz, 1H, H-3), 5.03-4.94 (m, 3H), 4.69 (s, 1H, H-1'), 4.46 (d, J=8.0 Hz, 1H, H-1), 4.40-4.30 (m, 2H), 4.20 (dd, J=12, 4.5 Hz, 1H), 4.13-3.96 (m, 2H), 3.93-3.81 (m, 3H), 3.64-3.44 (m, 4H), 2.14, 2.11, 2.09, 2.07, 2.04, 2.01, 1.98 (s each, 3H each, 7CH$_3$CO), 1.75-1.64 (m, 2H, —OCH$_2$CH$_2$CH$_2$—); ESI-MS: m/z: calcd for C$_{31}$H$_{45}$NO$_{17}$: 703.27; found: 704.47 [M+H]$^+$.

O-(2,3,4,6-Tetra-O-acetyl-β-D-mannopyranosyl)-(1→4)-2-acetamido-3,6-di-O-acetyl-1,2-dideoxy-α-D-glucopyrano)-[2,1-d]-2-oxazoline (17): NIS (15 mg, 1.2 equiv) and TESOTf (25 μL) were added to a solution of 16 (75 mg, 106 μmol) in anhydrous CH$_2$Cl$_2$ (20 mL). The mixture was stirred at RT for 0.5 h and then diluted with CH$_2$Cl$_2$, and washed with NaHCO$_3$ and brine. The organic layer was dried by Na$_2$SO$_4$ and filtered. The filtrate was concentrated and the residue was purified by flash silica gel column chromatography (hexanes/EtOAc 1:2) to give 17 (57.3 mg, 87%) as a white solid. $^1$H NMR (CDCl$_3$, 500 MHz): δ=5.90 (d, J=7.0 Hz, 1H, H-1), 5.54 (t, J=2.5 Hz, 1H, H-3), 5.41 (d, J=3.0 Hz, 1H, H-2'), 5.25 (t, J=10 Hz, 1H, H-4'), 5.05 (dd, J=9.5, 3.0 Hz, 1H, H-3'), 4.81 (s, 1H, H-1'), 4.27 (dd, J=12.5, 5.0 Hz, 1H, H-6'), 4.19-4.09 (m, 4H), 3.70-3.68 (m, 2H), 3.48-3.46 (m, 1H), 2.20, 2.11, 2.09, 2.09, 2.04, 2.04, (s each, 3H each, 6CH$_3$CO). 1.99 (s, 3H, CH$_3$); $^{13}$C NMR (CDCl$_3$, 125 MHz): δ=170.7, 170.6, 170.5, 170.0, 169.6, 169.3, 166.3, 99.3, 99.0, 76.1, 72.5, 70.8, 70.4, 68.4, 67.8, 66.0, 64.8, 63.6, 62.5, 60.4, 20.1, 20.9, 20.8, 20.7, 20.6, 20.5, 14.2; ESI-MS: m/z: calcd for C$_{26}$H$_{35}$NO$_{16}$: 617.2; found: 618.37 [M+H]$^+$.

O-(β-D-Mannopyranosyl)-(1→4)-1,2-dideoxy-α-D-glucopyrano)-[2,1-d]-2-oxazoline (1): A solution of 17 (57 mg, 100 μmol) in MeOH (2 mL) containing NaOMe (10 μmol) was stirred at RT for 2 h. Then the mixture was concentrated. The residue was dissolved in water and lyophilized to give the disaccharide oxazoline 1 (34 mg, quantitative) as a white solid. $^1$H NMR (D$_2$O, 500 MHz): δ=6.03 (d, J=7.5 Hz, 1H, H-1), 4.66 (s, 1H, H-1'), 4.32 (s, 1H, H-2'), 4.13 (s, 1H, H-2), 3.91-3.88 (m, 4H), 3.72-3.50 (m, 4H), 3.55-3.32 (m, 2H), 1.85 (s, 3H, CH$_3$—); $^{13}$C NMR (D$_2$O, 125 MHz): δ=168.6, 101.2, 99.9, 77.4, 76.4, 72.8, 70.9, 70.4, 69.3, 66.8, 65.2, 61.7, 61.1, 13.0 ESI-MS: m/z: calcd for C$_{14}$H$_{23}$NO$_{10}$: 365.13; found: 366.57 [M+H]$^+$.

4-Pentenyl O-(4-O-acetyl-2,3-di-O-benzoyl-6-O-benzyl-β-D-mannopyranosyl)-(1→4)-2-acetamido-3,6-di-O-benzoyl-2-deoxy-β-D-glucopyranoside (18): Trifluoroacetic anhydride (120 mL, 0.88 mmol) and Et$_3$SiH (240 μL, 0.44 mmol) were added at 0° C. to a solution of 15 (140 mg, 0.15 mmol) in dry CH$_2$Cl$_2$ (5 mL). After the reaction mixture was stirred at 0° C. for 5 min, TFA (112 μL, 0.44 mmol) was added dropwise over 2 min. The reaction was stirred from 0° C. to RT overnight. The mixture was diluted with EtOAc (50 mL), and the solution was washed with NaHCO$_3$ and brine, dried by Na$_2$SO$_4$, and filtered. The filtrate was dissolved in pyridine (5 mL) containing Ac$_2$O (0.5 mL). The mixture was stirred overnight at RT and then diluted with CH$_2$Cl$_2$, washed with NaHCO$_3$ and brine. The organic layer was dried by Na$_2$SO$_4$ and filtered. The filtrate was concentrated and the residue was purified by flash silica gel column chromatography (hexanes/EtOAc 2:1) to give 18 (107 mg, 76%) as a white foam. $^1$H NMR (500 MHz, CDCl$_3$): δ=8.08-7.26 (m, 25H, 5C$_6$H$_5$), 5.81 (d, J=2.5 Hz, 1H, H-2'), 5.77-5.71 (m, 1H, —CH═), 5.56 (d, J=8.0 Hz, 1H, NH), 5.47 (t, J=10.0 Hz, 1H, H-4'), 5.34 (t, J=9.0 Hz, 1H, H-3), 5.28 (dd, J=7.0, 3.0 Hz, 1H, H-3'), 4.97-4.90 (m, 3H), 4.72 (dd, J=11.5, 2.0 Hz, 1H, H-6a), 4.59 (dd, J=11.5, 4.0 Hz, 1H, H-6b), 4.48 (m, 2H), 4.37 (d, J=12.0 Hz, 1H, PhCH$_2$—), 4.29-4.17 (m, 2H), 3.86-3.81 (m, 2H), 3.49-3.28 (m, 4H), 2.10-2.06 (m, 2H, —OCH$_2$—CH$_2$—CH$_2$—), 1.80, 1.76 (s each, 3H each, 2CH$_3$CO), 1.72-1.64 (m, 2H, —OCH$_2$—CH$_2$—CH$_2$—); ESI-MS: m/z: calcd for C$_{56}$H$_{57}$NO$_{16}$: 999.37; found: 1000.16 [M+H]$^+$.

4-Pentenyl O-(2,3,4-O-triacetyl-6-O-benzyl-β-D-mannopyranosyl)-(1→4)-2-acetamido-3,6-di-O-acetyl-2-deoxy-β-D-glucopyranoside (19): A solution of the 18 (100 mg, 0.1 mmol) in MeOH (10 mL) containing NaOMe (0.1 equiv) was stirred at RT for 2 h. Then the mixture was neutralized by Dowex W50-X8 (H$^+$ form), filtered and concentrated. The foregoing compound was dissolved in pyridine (5 mL) containing Ac$_2$O (0.5 mL). The mixture was stirred at RT overnight and then diluted with CH$_2$Cl$_2$, and washed with NaHCO$_3$ and brine. The organic layer was dried by Na$_2$SO$_4$ and filtered. The filtrate was concentrated and the residue was purified by flash silica gel column chromatography (hexanes/EtOAc 1:2) to give 19 (71 mg, 95%). $^1$H NMR (500 MHz, CDCl$_3$): δ=7.32-7.26 (m, 5H, C$_6$H$_5$), 5.78-5.76 (m, 1H, —CH=), 5.41 (d, J=9.0 Hz, 1H, NH), 5.37 (d, J=2.3 Hz, 1H, H-2'), 5.22 (t, J=9.5 Hz, 1H, H-4), 5.14-4.94 (m, 5H), 4.66 (s, 1H, H-1'), 4.55-4.35 (m, 4H), 4.19 (dd, J=12.0, 4.0 Hz, 1H, H-6), 3.89-3.77 (m, 3H), 3.60-3.54 (m, 4H), 3.45-3.41 (m, 2H), 2.12, 2.09, 2.04, 2.01, 1.97, 1.94, 1.93 (s each, 3H each, 6CH$_3$CO), 1.68-1.58 (m, 2H, —OCH$_2$CH$_2$CH$_2$—); $^{13}$C NMR (CDCl$_3$, 125 MHz): δ=169.6, 169.5, 169.1, 168.8, 137.0, 136.6, 127.6, 127.1, 126.9, 114.0, 100.3, 96.5, 72.5, 71.5, 71.3, 68.2, 68.0, 61.5, 52.9, 29.0, 27.6, 22.4, 19.9, 19.8, 19.7; ESI-MS: m/z: calcd for C$_{36}$H$_{49}$NO$_{16}$: 751.77; found: 752.09 [M+H]$^+$.

O-(2,3,4-Tri-O-acetyl-6-benzyl-β-D-mannopyranosyl)-(1→4)-3,6-di-O-acetyl-1,2-dideoxy-α-D-glucopyrano)-[2,1-d]-2-oxazoline (20): NIS (12 mg, 1.3 equiv) and TESOTf (13 μL) were added to a solution of 19 (38 mg, 51 μmol) in anhydrous CH$_2$Cl$_2$ (5 mL), and the mixture was stirred at RT for 0.5 h until TLC indicated the completion of the reaction. The mixture was diluted with CH$_2$Cl$_2$ and washed with NaHCO$_3$ and brine. The mixture was dried by Na$_2$SO$_4$ and filtered. The filtrate was concentrated and the residue was purified by flash silica gel column chromatography (hexanes/EtOAc/Et$_3$N 1:2:0.01) to give 20 (26 mg, 78%) as a white solid. $^1$H NMR (CDCl$_3$, 500 MHz): δ=7.33-7.32 (m, 5H, C$_6$H$_5$), 5.88 (d, J=7.0 Hz, 1H, H-1), 5.54 (dd, J=4.5, 2.5 Hz, 1H, H-3), 5.39 (d, J=3.5 Hz, 1H, H-2'), 5.35 (t, J=10 Hz, 1H, H-4'), 5.03 (dd, J=10.0, 3.0 Hz, 1H, H-3'), 4.80 (s, 1H, H-1'), 4.52 (d, J=12.0 Hz, 1H, PhCH$_2$—), 4.19 (d, J=12.0 Hz, 1H, PhCH$_2$—), 4.19-4.09 (m, 4H), 3.70-3.68 (m, 2H), 3.73-3.54 (m, 4H), 2.28, 2.10, 2.01, 1.98, 1.90 (s each, 3H each, 5CH$_3$CO—), 1.89 (s, 3H, CH$_3$); $^{13}$C NMR (CDCl$_3$, 125 MHz): δ=170.7, 170.1, 169.8, 169.3, 166.2, 138.0, 128.4, 127.9, 127.7, 99.4, 98.8, 73.9, 73.5, 70.9, 70.7, 69.7, 68.5, 63.6, 21.1, 20.9, 20.8, 20.7, 13.9, 11.4; ESI-MS: m/z: calcd for C$_{31}$H$_{39}$NO$_{15}$: 665.23; found: 666.16 [M+H]$^+$.

O-(6-Benzyl-β-D-mannopyranosyl)-(1→4)-1,2-dideoxy-α-D-glucopyrano)-[2,1-d]-2-oxazoline (4): A solution of compound 20 (22 mg, 36 μmol) in MeOH containing NaOMe (5 μmol) was stirred at RT for 2 h. Then the mixture was concentrated. The residue was dissolved in water and lyophilized to give the oxazoline 4 (15 mg, quantitative) as a white solid. $^1$H NMR (CD$_3$OD, 500 MHz): δ=7.39-7.32 (m, 5H, C$_6$H$_5$), 5.99 (d, J=7.2 Hz, 1H, H-1), 4.64-4.59 (m, 3H, H-1', 2 PhCH$_2$—), 4.23 (t, J=2.8 Hz, 1H, H-2'), 4.06-4.04 (m, 1H), 3.85-3.29 (m, 12H), 2.13 (s, 3H, CH$_3$—); $^{13}$C NMR (CD$_3$OD, 125 MHz): δ=168.7, 137.2, 128.8, 128.6, 128.4, 101.3, 99.9, 77.6, 75.1, 73.3, 72.8, 70.9, 70.4, 69.4, 69.3, 13.0; ESI-MS: m/z: calcd for C$_{21}$H$_{29}$NO$_{10}$: 455.18; found: 456.16 [M+H]$^+$.

4-Pentenyl O-(2,3-di-O-benzoyl-β-D-mannopyranosyl)-(1→4)-2-acetamido-3,6-di-O-benzoyl-2-deoxy-β-D-glucopyranoside (21) and 4-pentenyl O-(4,6-di-O-acetyl-2,3-di-O-benzoyl-β-D-mannopyranosyl)-(1→4)-2-acetamido-3,6-di-O-benzoyl-2-deoxy-β-D-glucopyranoside (22): A solution of compound 15 (110 mg, 0.21 mmol) in 80% HOAc (10 mL) was stirred at 50° C. for 4 h. Concentration of the reaction mixture followed by purification on a silica gel column (CH$_2$Cl$_2$/MeOH 30:1) gave compound 21 (95 mg, 92%). ESI-MS: m/z: calcd for C$_{47}$H$_{49}$NO$_{15}$: 867.31; found: 868.28 [M+H]$^+$.

The identity of compound 21 was further characterized by conversion to the 4',6'-di-O-acetyl derivative 22. To a solution of 21 in pyridine (5 mL) was added Ac$_2$O (0.5 mL). The mixture was stirred at RT for 4 h, and then diluted with CH$_2$Cl$_2$. The solution was washed with NaHCO$_3$ and brine, and the organic layer was dried by Na$_2$SO$_4$ and filtered. The filtrate was concentrated and the residue was purified by flash silica gel column chromatography (hexanes/EtOAc 1:1) to give 22 (96 mg, 100%). $^1$H NMR (500 MHz, CDCl$_3$): δ=8.11-7.26 (m, 20H, 5C$_6$H$_5$), 5.82 (d, J=3.0 Hz, 1H, H-2'), 5.72-5.69 (m, 1H, —CH=), 5.38 (dd, J=9.0 Hz, 1H, H-3), 5.27 (dd, J=9.0, 3.5 Hz, 1H, H-3'), 5.01-4.94 (m, 3H, H-1', =CH$_2$—), 4.60 (m, 2H), 4.51 (d, J=8.0 Hz, 1H, H-1), 4.21-4.16 (m, 2H), 4.06-3.96 (m, 2H), 3.85-3.82 (m, 1H), 3.74-3.69 (m, 3H), 3.48-3.38 (m, 2H), 2.14-2.10 (m, 2H, —OCH$_2$CH$_2$CH$_2$—), 2.01, 1.85, 1.79 (3 s, 9H, 3CH$_3$CO), 1.68-1.58 (m, 2H, —OCH$_2$CH$_2$CH$_2$—); ESI-MS: m/z: calcd for C$_{51}$H$_{53}$NO$_{17}$: 951.33; found: 952.26 [M+H]$^+$.

4-Pentenyl O-[(2,3,4,6-tetra-O-benzoyl-α-D-mannopyranosyl)-(1→6)-(2,3-di-O-benzoyl-β-D-mannopyranosyl)]-(1→4)-2-acetamido-3,6-di-O-benzoyl-2-deoxy-β-D-glucopyranoside (23) and 4-pentenyl O-[(2,3,4,6-tetra-O-benzoyl-α-D-mannopyranosyl)-(1→6)-(4-O-acetyl-2,3-di-O-benzoyl-β-D-mannopyranosyl)]-(1→4)-2-acetamido-3,6-di-O-benzoyl-2-deoxy-β-D-glucopyranoside (24): A suspension of compound 22 (70 mg, 75 μmol) and 2,3,4,6-tetra-O-benzoyl-α-D-mannopyranosyl trichloroacetimidate (60 mg, 81 μmol) in dry CH$_2$Cl$_2$ (4 mL) containing activated 4 Å molecular sieves (100 mg) was stirred under an atmosphere of argon at RT for 30 min. After cooling to −20° C., a solution of TMSOTf in CH$_2$Cl$_2$ (0.1 M, 40 μL, 4 μmol) was added and the resulting mixture was stirred from −20° C. to RT for 3 h. The reaction was quenched with Et$_3$N and diluted with CH$_2$Cl$_2$ (10 mL). The solution was washed with brine and the organic layer was dried over Na$_2$SO$_4$ and filtered. The filtrate was concentrated in vacuo and the residue was purified by flash silica gel column chromatography (hexanes/EtOAc 2:1) to give compound 23 (82 mg, 76%) as a white foam. ESI-MS: m/z: calcd for C$_{81}$H$_{75}$NO$_{24}$: 1445.47; found: 1446.52 [M+H]$^+$.

Compound 23 was further characterized by its conversion to the 4'-O-acetyl derivative 24. Compound 23 (40 mg, 27 μmol) was dissolved in pyridine (2 mL) containing Ac$_2$O (0.5 mL). The mixture was stirred at RT overnight. The mixture was diluted with CH$_2$Cl$_2$ and washed with NaHCO$_3$, brine, dried by Na$_2$SO$_4$ and filtered. The filtrate was concentrated and the residue was purified by flash silica gel column chromatography (hexanes/EtOAc 2:1) to give 24 (42 mg, quantitative) as a white foam. $^1$H NMR (500 MHz, CDCl$_3$): δ=8.09-7.32 (m, 40H, 8C$_6$H$_5$), 6.11 (d, J=10.0 Hz, 1H, H-4"), 5.92-5.87 (m, 3H, NH, H-4', H-3"), 5.78-5.76 (m, 1H), 5.72-5.67 (m, 1H, =CH—), 5.65-5.60 (m, 2H), 5.37 (dd, J=10.0, 3.5 Hz, 1H, H-3'), 5.05 (s, 1H, H-1"), 4.96-4.89 (m, 3H), 4.82 (d, J=8.5 Hz, 1H), 4.70-4.60 (m, 4H), 4.49-4.42 (m, 2H), 4.28-4.26 (m, 2H), 4.19 (t, J=9.5 Hz, 1H, H-4), 3.71-3.62 (m, 3H), 3.46-3.30 (m, 3H), 2.10-2.06 (m, 2H, —$CH_2CH_2O$), 1.95, 1.77 (s each, 3H each, 2$CH_3CO$), 1.68-1.58 (m, 2H, —$OCH_2CH_2$—); $^{13}C$ NMR ($CDCl_3$, 125 MHz): δ=170.61, 169.7, 166.3, 166.2, 115.28, 99.0, 98.1, 96.9, 77.4, 77.1, 76.8, 72.7, 72.4, 71.5, 70.0, 68.8, 67.8, 66.9, 63.0, 62.9, 52.44, 30.27, 29.8, 28.3, 23.1, 20.8; ESI-MS: m/z: calcd for $C_{83}H_{77}NO_{25}$: 1487.48; found: 1488.61 $[M+H]^+$.

4-Pentenyl O-[(2,3,4,6-tetra-O-acetyl-α-D-mannopyranosyl)-(1→6)-(2,3,4-triacetyl-β-D-mannopyranosyl)]-(1→4)-2-acetamido-3,6-di-O-acetyl-2-deoxy-β-D-glucopyranoside (25): A solution of 24 (150 mg, 101 µmol) in MeOH (10 mL) containing NaOMe (10 µmol) was stirred at RT for 2 h. Then the mixture was neutralized by Dowex W50-X8 ($H^+$ form), filtered and concentrated. The foregoing compound was dissolved in pyridine (5 mL) and $Ac_2O$ (1 mL). The mixture was stirred at RT overnight. The mixture was diluted with $CH_2Cl_2$ and washed with $NaHCO_3$, brine, and water. The organic layer was dried by $Na_2SO_4$ and filtered. The filtrate was concentrated and the residue was purified by flash silica gel column chromatography (hexanes/EtOAc 1:2) to give 25 (95 mg, 95%). $^1H$ NMR ($CDCl_3$, 500 MHz): δ=5.87-5.62 (m, 2H, NH, —CH═), 5.43 (d, J=2.8 Hz, 1H, H-2"), 5.28-5.10 (m, 5H), 5.02-4.94 (m, 3H), 4.77 (s, 1H, H-1"), 4.68 (s, 1H, H-1'), 4.67 (d, J=8.8 Hz, 1H, H-1), 4.43-4.10 (m, 6H), 3.81-3.80 (m, 2H), 3.55-3.28 (m, 3H), 2.11, 2.10, 2.08, 2.06, 2.00, 1.99, 1.97, 1.93, 1.92 (9 s, 30H, 9$CH_3$); ESI-MS: m/z: calcd for $C_{43}H_{61}NO_{25}$: 991.35; found: 992.15 $[M+H]^+$.

O-[(2,3,4,6-Tetra-O-acetyl-α-D-mannopyranosyl)-(1→6)-(2,3,4-tri-O-acetyl-β-D-mannopyranosyl)]-(1→4)-3,6-di-O-acetyl-1,2-dideoxy-α-D-glucopyrano)-[2,1-d]-2-oxazoline (26): NIS (13 mg, 1.3 equiv) and TESOTf (14 µL) were added to a solution of 25 (50 mg, 50 µmol) in dry $CH_2Cl_2$ (5 mL). The mixture was stirred at RT for 0.5 h when TLC indicated the completion of the reaction. The mixture was diluted with $CH_2Cl_2$ and washed with $NaHCO_3$ and brine. The organic layer was dried by $Na_2SO_4$ and filtered. The filtrate was concentrated and the residue was purified by flash chromatography on silica gel using (EtOAc/hexanes 2:1 containing 1% $Et_3N$) to give 26 (37 mg, 80%) as a white solid. $^1H$ NMR ($CDCl_3$, 500 MHz): δ=5.91 (d, J=7.5 Hz, 1H, H-1), 5.61-5.60 (s, 1H, H-3), 5.40 (d, J=3.5 Hz, 1H, H-2'), 5.31-5.27 (m, 3H), 5.20 (t, J=10.0 Hz, 1H, H-4'), 5.03 (dd, J=3.0, 10.0 Hz, 1H, H-3"), 4.85 (s, 1H, H-1'), 4.84 (s, 1H, H-1"), 4.34 (dd, J=4.0, 12.0 Hz, 1H, H-6), 4.18-4.08 (m, 5H), 3.92 (dd, J=4.4, 11.0 Hz, 1H), 3.76-3.74 (m, 1H), 3.67-3.59 (m, 2H), 3.45-3.43 (m, 1H), 2.18, 2.15, 2.12, 2.11, 2.10, 2.07, 2.04, 2.01, 1.99, (s each, 3H each, 10$CH_3CO$), 1.96 (s, 3H, $CH_3$); ESI-MS: m/z: calcd for $C_{43}H_{61}NO_{25}$: 905.28; found: 906.53 $[M+H]^+$.

O-[(α-D-Mannopyranosyl)-(1→6)-(β-D-mannopyranosyl)]-(1→4)-1,2-dideoxy-α-D-glucopyrano)-[2,1-d]-2-oxazoline (3): A solution of 26 (22 mg, 24 µmol) in MeOH containing NaOMe (3 µmol) was stirred at RT for 2 h. Then the mixture was concentrated. The residue was dissolved in water and lyophilized to give 3 (13 mg, quantitative) as a white solid. $^1H$ NMR ($CD_3OD$, 500 MHz): δ=6.00 (d, J=7.2 Hz, 1H, H-1), 4.79 (s, 1H, H-1'), 4.62 (s, 1H, H-2'), 4.59 (s, 2H, H-1", H-2"), 4.20 (s, 1H, H-2), 4.04-4.02 (m, 1H), 3.9-3.26 (m, 14H), 2.01 (s, 3H, $CH_3$—); $^{13}C$ NMR ($CD_3OD$, 125 MHz): δ=168.6, 100.0, 99.7, 99.6, 77.8, 74.5, 73.0, 72.7, 70.4, 70.1, 69.9, 69.4, 66.8, 66.3, 65.1, 61.7, 60.8, 13.0; ESI-MS: m/z: calcd for $C_{20}H_{33}NO_{15}$: 527.19; found: 528.29 $[M+H]^+$.

Acceptor GlcNAc-peptide 27: GlcNAc-tripeptide 27 was synthesized on a Pioneer automatic peptide synthesizer (Applied Biosystems) using Fmoc chemistry on a PAL-PEG-PS resin (on 0.2 mmol scale), following the previously described procedure. [7] After the solid-phase synthesis, the peptide was retrieved from the resin with 95% TFA, followed by the treatment with 5% hydrazine to remove the O-acetyl groups. The resulting crude GlcNAc-peptide was purified by preparative RP-HPLC to provide the GlcNAc-tripeptide 27 (104 mg, 88%). $^1H$ NMR ($D_2O$, 500 MHz): δ=4.98 (d, J=9.8 Hz, 1H, NH—Ac), 4.65 (d, J=7.0 Hz, 1H, H-1), 4.25 (d, J=4.4 Hz, 1H, Thr-Hα), 4.17 (d, J=7.5 Hz, 1H, Leu-Hα), 4.16 (dd, J=4.5, 6.5 Hz, 1H, Asn-Hα), 3.81 (dd, J=12.4, 1.8 Hz, 1H, H-3), 3.74 (t, J=10.0 Hz, 1H, H-2), 3.68 (dd, J=12.3, 4.8 Hz, 1H, H-6), 3.53 (t, J=8.4 Hz, 1H, H-4), 3.45-3.38 (m, 3H, Leu-Hβ, H-5, H-6), 2.77 (dd, J=5.8, 16.0 Hz, 1H, Asn-Hβ), 2.65 (dd, J=16.0, 7.8 Hz, 1H, Asn-Hβ), 1.95 (s, 3H, $NHCOCH_3$), 1.94 (s, 3H, $NHCOCH_3$), 1.87-1.90 (m, 1H, Leu-Hβ), 1.45-1.48 (m, 2H, Leu-$CH_2$), 1.14 (d, J=6.6 Hz, 3H, Thr-$CH_3$), 0.85 (d, J=7 Hz, 3H, Leu-$CH_3$), 0.80 (t, J=7 Hz, 3H, Leu-$CH_3$); ESI-MS: m/z: calcd for $C_{24}H_{42}N_6O_{11}$: 590.29; found: 591.29 $[M+H]^+$.

General procedure for the ENGase-catalyzed transglycosylation: A mixture of the respective oligosaccharide oxazoline (10-30 µmol) and the GlcNAc-tripeptide 27 (3 molar equivalents of the donor) or the GlcNAc-C34 [7] (5 molar equivalents of the donor) in a phosphate buffer (50 mM, pH 6.5, 0.5-1 mL) was incubated at 25° C. with the enzyme Endo-A (100 mU). The oxazoline derivative was added in portions during the reaction. The reaction was monitored by analytical HPLC by taking aliquots at intervals. It was observed that the transglycosylation reaction with the disaccharide oxazoline derivatives 1 and 4 proceeded slowly and took more than 48 h for reaching the plateau, while the transglycosylation with the tetrasaccharide oxazoline 2 proceeded quickly and would be complete within 2 h. The reaction was stopped by heating in a boiling water bath for 3 min when the peak of the transglycosylation product reached the maximum. The product was purified by preparative HPLC on a Waters preparative column (Symmetry 300, 19×300 mm) to afford the respective glycopeptide, which was characterized by NMR and ESI-MS).

Glycopeptide 28: yield: 3.0 mg, 63% (based on the reaction with 5 µmol of 27); $^1H$ NMR ($D_2O$, 500 MHz): δ=4.97 (d, J=10.0 Hz, 1H, NH—Ac), 4.66 (d, J=7.0 Hz, 1H, H-1), 4.65 (s, 1H, H-1"), 4.53 (d, J=7.5 Hz, 1H, H-1'), 4.24 (d, J=4.4 Hz, 1H, Thr-Hα), 4.20 (d, J=7.5 Hz, 1H, Leu-Hα), 4.15 (dd, J=6.2, 4.4 Hz, 1H, Asn-Hα), 4.00 (d, J=3.2 Hz, 1H, H-2"), 3.86-3.32 (m, 18H), 2.77 (dd, J=5.8, 16.0 Hz, 1H, Asn-Hβ), 2.65 (dd, J=7.8, 16.0 Hz, 1H, Asn-Hβ), 1.99 (s, 3H, $NHCOCH_3$), 1.95 (s, 3H, $NHCOCH_3$), 1.93 (s, 3H, $NHCOCH_3$), 1.92-1.82 (m, 1H, Leu-HP), 1.42-1.34 (m, 2H, Leu-$CH_2$), 1.14 (d, J=6.6 Hz, 3H, Thr-$CH_3$), 0.85 (d, J=7.0 Hz, 3H, Leu-$CH_3$), 0.80 (t, J=7 Hz, 3 H, Leu-$CH_3$); ESI-MS: m/z: calcd for $C_{38}H_{65}N_7O_{21}$: 955.42; found: 956.39 $[M+H]^+$.

Glycopeptide 29: yield: 5.5 mg, 86% (based on the reaction with 5 µmol of 27); $^1H$ NMR ($D_2O$, 500 MHz): δ=5.02 (s, 1H, H-1""), 4.97 (d, J=10.0 Hz, 1H, NH—Ac), 4.84 (d, J=1.40 Hz, 1H, H-1'''), 4.65 (d, J=7.1 Hz, 1H, H-1), 4.55 (d, J=7.8 Hz, 1H, H-1"), 4.53 (d, J=7.5 Hz, 1H, H-1'), 4.24 (d, J=4.4 Hz, 1H, Thr-Hα), 4.18 (d, J=7.5 Hz, 1H, Leu-Hα), 4.15 (dd, J=4.4, 6.2 Hz, 1H, Asn-Hα), 3.99 (dd, J=2.0, 3.5 Hz, 1H, H-2"), 3.90 (dd, J=1.5, 3.5 Hz, 1H, H-2""), 3.86-3.46 (m, 29H), 2.77 (dd, J=5.8, 16.0 Hz, 1H, Asn-Hβ), 2.65 (dd, J=7.8, 16.0 Hz, 1H, Asn-Hβ), 1.99 (s, 3H, $NHCOCH_3$), 1.95 (s, 3H, $NHCOCH_3$), 1.93 (s, 3H, $NHCOCH_3$), 1.92-1.82 (m, 1H, Leu-Hβ), 1.42-1.34 (m, 2H, Leu-$CH_2$), 1.14 (d, J=6.6 Hz, 3H, Thr-$CH_3$), 0.85 (d, J=7 Hz, 3H, Leu-$CH_3$), 0.80 (t, J=7 Hz, 3H, Leu-$CH_3$); ESI-MS: m/z: calcd for $C_{50}H_{89}N_7O_{31}$: 1279.53; found: 1280.62 $[M+H]^+$.

Glycopeptide 30: yield: 4 mg, 72% (based on the reaction with 5 μmol of 27); $^1$H NMR (D$_2$O, 500 MHz): δ=4.97 (d, J=8.7 Hz, 1H, NH—Ac), 4.84 (s, 1H, H-1'''), 4.72 (d, J=7.5 Hz, 1H, H-1), 4.65 (s, 1H, H-1''), 4.53 (d, J=7.5 Hz, 1H, H-1'), 4.24 (d, J=4.5 Hz, 1H, Thr-Hα), 4.20 (d, J=7.5 Hz, 1H, Leu-Hα), 4.15 (dd, J=4.4, 6.2 Hz, 1H, Asn-Hβ), 4.00 (d, J=3.2 Hz, 1H, H-2''), 3.88-3.32 (m, 23H), 2.75 (dd, J=5.8, 16.0 Hz, 1H, Asn-Hβ), 2.61 (dd, J=7.8, 16.0 Hz, 1H, Asn-Hβ), 2.00 (s, 3H, NHCOCH$_3$), 1.94 (s, 3H, NHCOCH$_3$), 1.93 (s, 3H, NHCOCH$_3$), 1.92-1.82 (m, 1H, Leu-Hβ), 1.42-1.34 (m, 2H, Leu-CH$_2$), 1.14 (d, J=6.6 Hz, 3H, Thr-CH$_3$), 0.85 (d, J=7 Hz, 3H, Leu-CH$_3$), 0.80 (t, J=7 Hz, 3H, Leu-CH$_3$); ESI-MS: m/z: calcd for C$_{44}$H$_{75}$N$_7$O$_{26}$: 1117.48; found: 1118.60 [M+H]$^+$.

Glycopeptide 31: yield: 2.87 mg, 55% (based on the reaction with 5 μmol of 27); $^1$H NMR (D$_2$O, 500 MHz): δ=7.38-7.32 (m, 5H, C$_6$H$_5$), 4.97 (d, J=8.5 Hz, 1H, NH—Ac), 4.66 (d, J=7.2 Hz, 1H, H-1), 4.53 (d, J=7.5 Hz, 1H, H-1'), 4.24 (d, J=4.4 Hz, 1H, Thr-Hα), 4.19 (d, J=7.5 Hz, 1H, Leu-Hα), 4.15 (dd, J=4.4, 6.2 Hz, 1H, Asn-Hα), 3.98 (d, J=3.8 Hz, 1H, H-2''), 3.86-3.40 (m, 21H), 2.77 (dd, J=5.8, 16.0 Hz, 1H, Asn-Hβ), 2.65 (dd, J=7.8, 16.0 Hz, 1H, Asn-Hβ), 1.99 (s, 3H, NHCOCH$_3$), 1.95 (s, 3H, NHCOCH$_3$), 1.93 (s, 3H, NHCOCH$_3$), 1.90-1.82 (m, 1H, Leu-HP), 1.42-1.34 (m, 2H, Leu-CH$_2$), 1.14 (d, J=6.6 Hz, 3H, Thr-CH$_3$), 0.85 (d, J=7 Hz, 3H, Leu-CH$_3$), 0.80 (t, J=7 Hz, 3H, Leu-CH$_3$); ESI-MS: m/z: calcd for C$_{45}$H$_{71}$N$_7$O$_{21}$: 1045.47; found: 1046.40 [M+H]$^+$.

Glycopeptide 32: Yield: 5.6 mg, 75% (based on the reaction with 1.5 μmol of GlcNAc-C34); ESI-MS: m/z: calcd for: 5018.22; found: 1674.04 [M+3H]$^{3+}$, 1255.64 [M+4H]$^{4+}$, 1004.78 [M+5H]$^{5+}$.

Glycopeptide 33: Yield: 5.0 mg, 68% (based on the reaction with 1.5 μmol of GlcNAc-C34); ESI-MS: m/z: calcd for: 4946.44; found: 1649.68 [M+3H]$^{3+}$, 1237.50 [M+4H]$^{4+}$, 990.20 [M+5H]$^{5+}$.

Pronase digestion of glycopeptides 32 and 33: Glycopeptide 32 (0.5 mg) was digested with pronase (30 μg, Sigma) in a phosphate buffer (pH 8.2, 100 μL) at 37° C. for 4 h. The reaction mixture was subjected to Sephadex G-10 gel filtration and the carbohydrate positive fractions (detected by anthrone assay) were pooled and subjected to ESI-MS analysis. ESI-MS: m/z: calcd for Man$_2$GlcNAc$_2$Asn: 862.78; found: 863.62 [M+H]$^+$. Similarly the Bn-tagged glycopeptide 33 (0.3 mg) was digested with pronase as described above, and the digestion product was isolated and characterized. EST-MS: m/z: calcd for Bn-Manβ1→4GlcNAcβ1→4GlcNAcβ1→Asn: 790.31; found: 791.40 [M+H]$^+$.

Examples for Glycoprotein Synthesis and Remodeling

Figure 10:
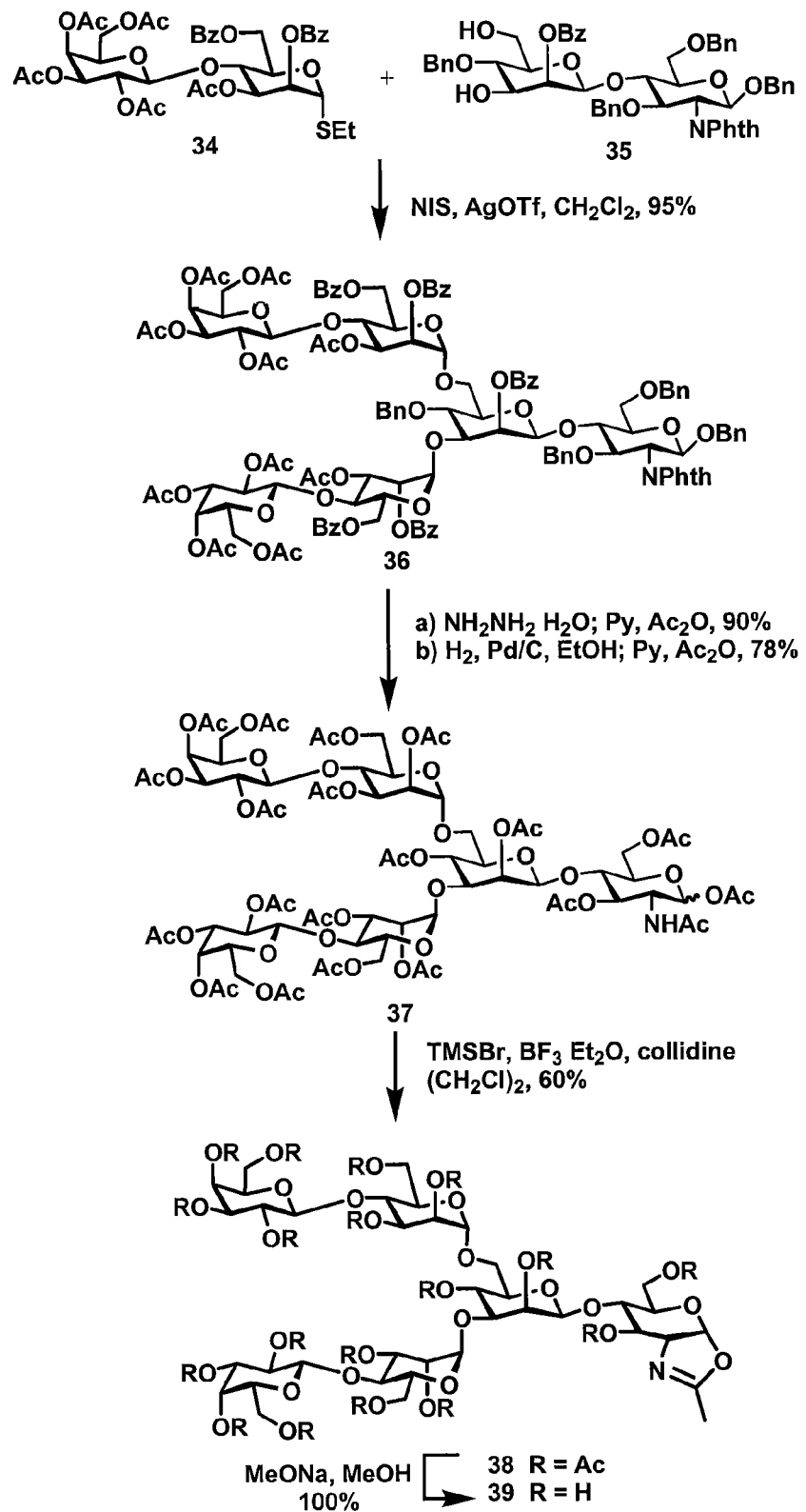
FIG. 10 shows the synthesis scheme of an unnatural hexasaccharide oxazoline.

The following example was conducted to examine whether the chemoenzymatic method can be extended to real glycoprotein synthesis and remodeling. For the purpose, a nonnatural hexasaccharide (Gal$_2$Man$_3$GlcNAc) oxazoline was designed and synthesized, which has two galactose residues □-1,4-linked to the terminal mannose residues in the Man$_3$GlcNAc core, as shown in FIG. 10. This unnatural hexasaccharide oxazoline was also designed to examine whether the endoglycosidase could also tolerate selective modifications on the outer mannose moieties of the Manα1,3(Manα1,6)Man□1,4GlcNAc core of N-glycans. This hexasaccharide derivative can be regarded as a mimic of a bi-antennary complex type N-glycan without the interlinked GlcNAc moieties. Glycosidation of the disaccharide acceptor 35 with two units of the disaccharide donor 34 under the catalysis of NIS and AgOTf gave the hexasaccharide intermediate 36 in excellent yield. NMR analysis confirmed that the newly formed glycosidic bonds were in the desired α-glycosidic linkage. Compound 36 was then converted to the per-O-acetylated hexasaccharide 37 through a series of protecting group manipulations. The formation of the oxazoline ring was achieved by the treatment of compound 37 with Lewis acid (TMSBr, BF$_3$, Et$_2$O) and collidine to provide compound 38 in 60% yield. Finally, de-O-acetylation of 38 with a catalytic amount of MeONa in dry MeOH afforded the free hexasaccharide oxazoline 39 in quantitative yield.

Figure 11:
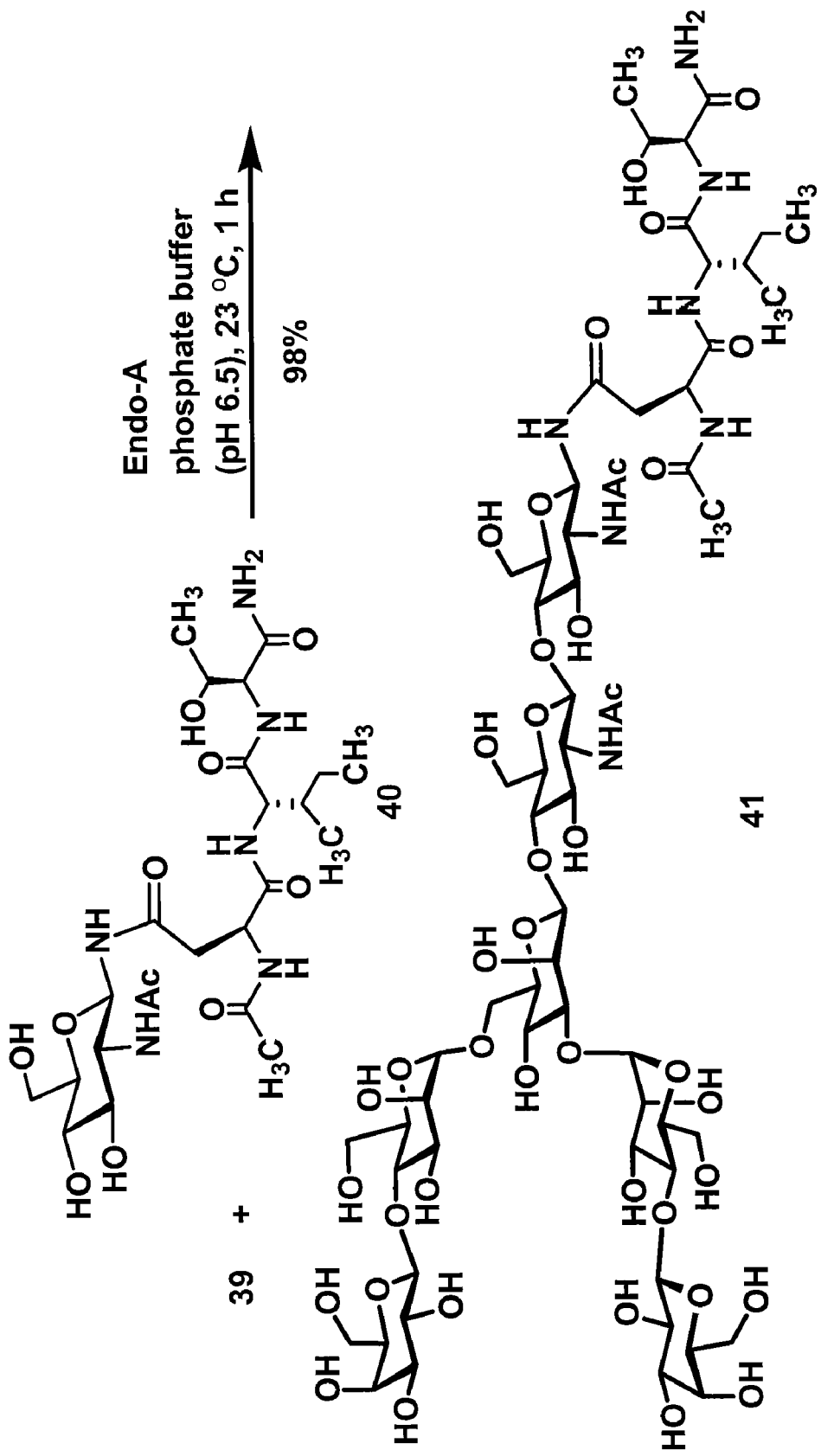
FIG. 11 shows the synthesis scheme of the EPO fragment glycopeptide 41.

To examine whether the endoglycosidase Endo-A is able to recognize the synthetic nonnatural sugar oxazoline for trans-glycosylation, a model reaction was carried out with a small GlcNAc-peptide, Ac-Asn(GlcNAc)-Ile-Thr (40), [9] as the acceptor, as shown in FIG. 11. The enzymatic reaction was monitored by reverse-phase HPLC. It was observed that the reaction between 39 and 40 (molar ratio 2:1) occurred quickly in the presence of Endo-A, while no ligation would occur in the absence of the enzyme. The glycosylation of the acceptor 40 with oxazoline 39 under the catalysis of Endo-A was essentially complete within 30 min to form the glycopeptide 41, which was isolated in 98% yield. The identity of the glycopeptide was characterized by ESI-MS and NMR. The observed MS (1604.1 Da) as revealed by ESI-MS matched well with the calculated MS (exact mass, 1603.63 Da) of glycopeptide 41, indicating that it is the adduct of the hexasaccharide oxazoline and the acceptor Ac-Asn(GlcNAc)-Ile-Thr. On the other hand, a doublet at δ4.56 with a relatively large coupling constant (J=7.5 Hz) assigned for the H-1 of the second GlcNAc suggested that the hexasaccharide was attached to the GlcNAc in the peptide moiety via the expected. β-1,4-glycosidic linkage. The results clearly indicate that the synthetic hexasaccharide oxazoline can serve as an excellent substrate for the Endo-A catalyzed trans-glycosylation, making it possible to incorporate nonnatural sugar chains into peptides.

To examine the feasibility of the chemoenzymatic method for glycoprotein synthesis and remodeling, bovine ribonuclease B was chosen as a model system, which has been used previously as a system for demonstrating glycoprotein remodeling. [6a] Ribonuclease B is a small glycoprotein that consists of 124 amino acids and contains a single glycosylation site at Asn-34. Natural ribonuclease B is a mixture of several glycoforms carrying a range of high-mannose type N-glycans (Man$_{5-9}$GlcNAc$_2$) at Asn-34. Treatment of ribonuclease B (42) with Endo-H (an endoglycosidase that cleaves high-mannose type N-glycans at the chitobiose core) removed the N-glycans, which leaves only the innermost N-acetylglucosamine (GlcNAc) at the Asn-34 site, giving the homogeneous GlcNAc-RB (43).

Figure 12:
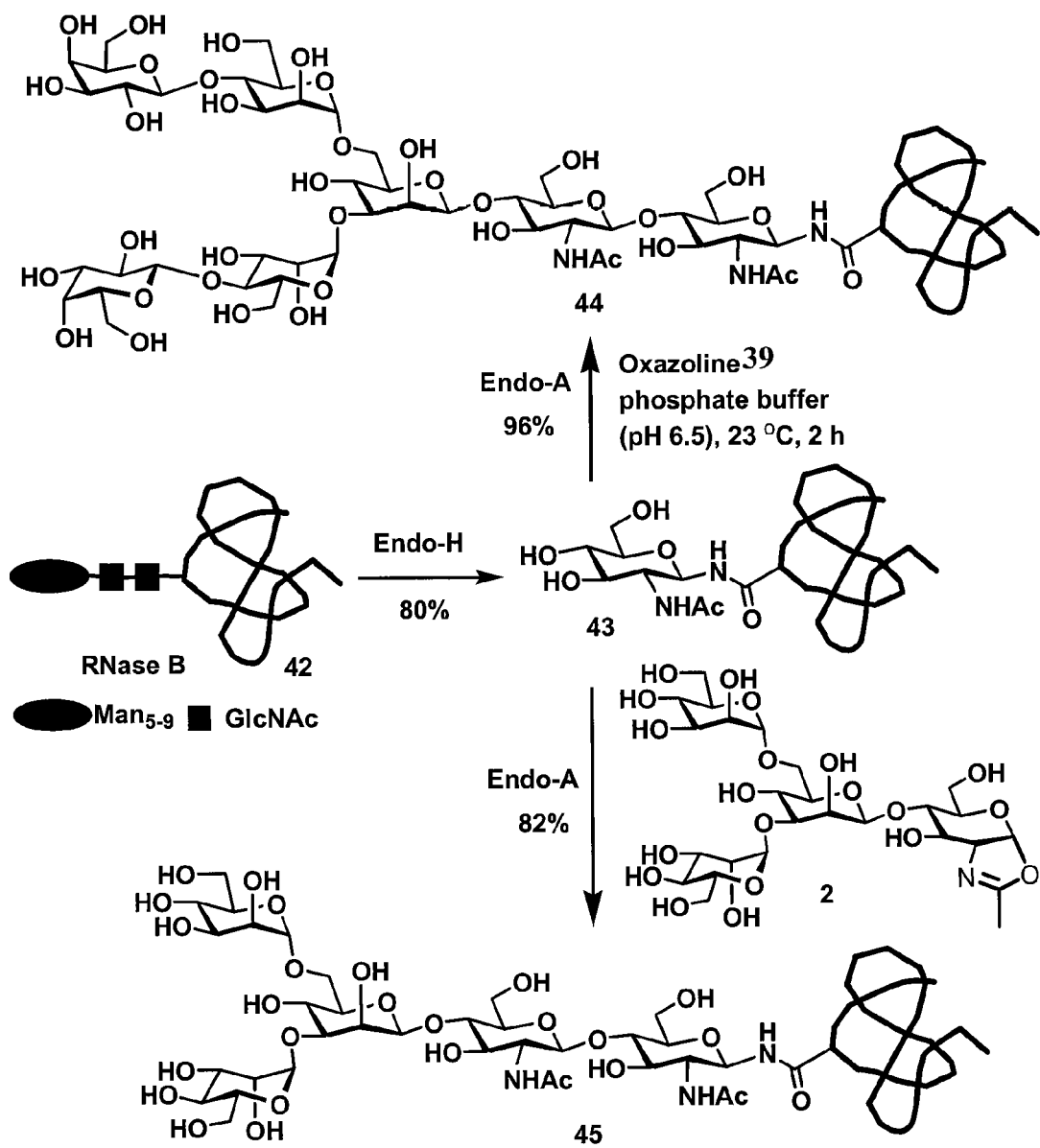
FIG. 12 shows the endoglycosidase-catalyzed synthesis of homogeneous glycoproteins by using ribonuclease B as a model system and the synthesis scheme of glycoproteins 44 and 45.

It was found, as shown in FIG. 12, that when the hexasaccharide oxazoline 39 and GlcNAc-RB (molar ratio, 2:1) were incubated in a phosphate buffer (pH 6.5) at 23° C. in the presence of Endo-A, the GlcNAc-RB was smoothly glycosylated to give the trans-glycosylation product 44, which was eluted earlier than GlcNAc-RB under reverse-phase HPLC. The transformation was essentially quantitative after 2 h reaction and the glycoprotein product was isolated in 96% yield. Deconvolution of the ESI-MS of 44 gave a molecular mass of 14901 Da, which is in good agreement with the calculated MS (14900 Da) of the glycoprotein 44. These results clearly indicated that the chemoenzymatic approach was equally efficient for the synthesis of homogeneous glycoproteins carrying structurally defined oligosaccharides.

Figure 13A:
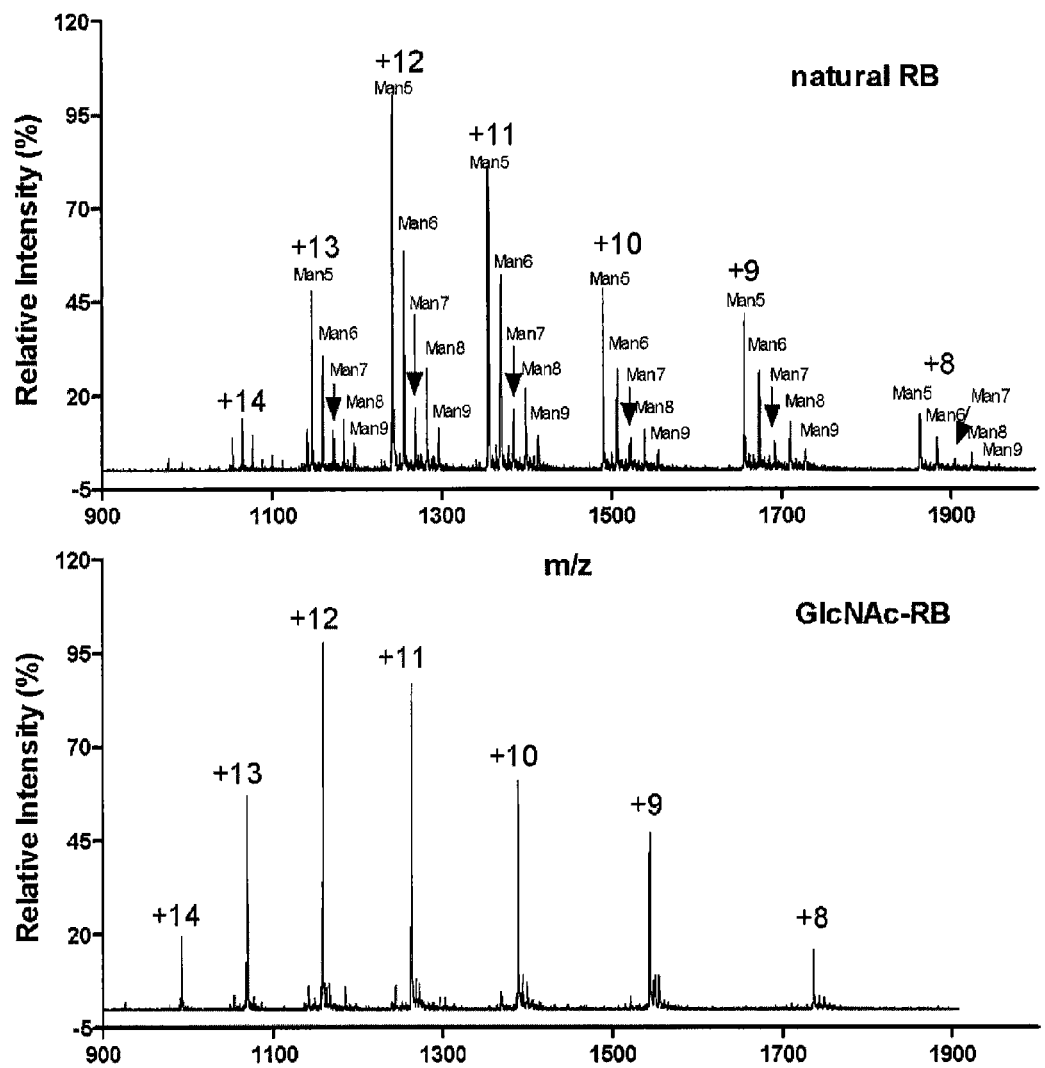
FIGS. 13A and B show the ESI-MS spectra f the natural ribonuclease compared to of the synthetic glycoproteins FIG. 14 describes an example of a glycosylation state for an antibody.
Figure 13B:
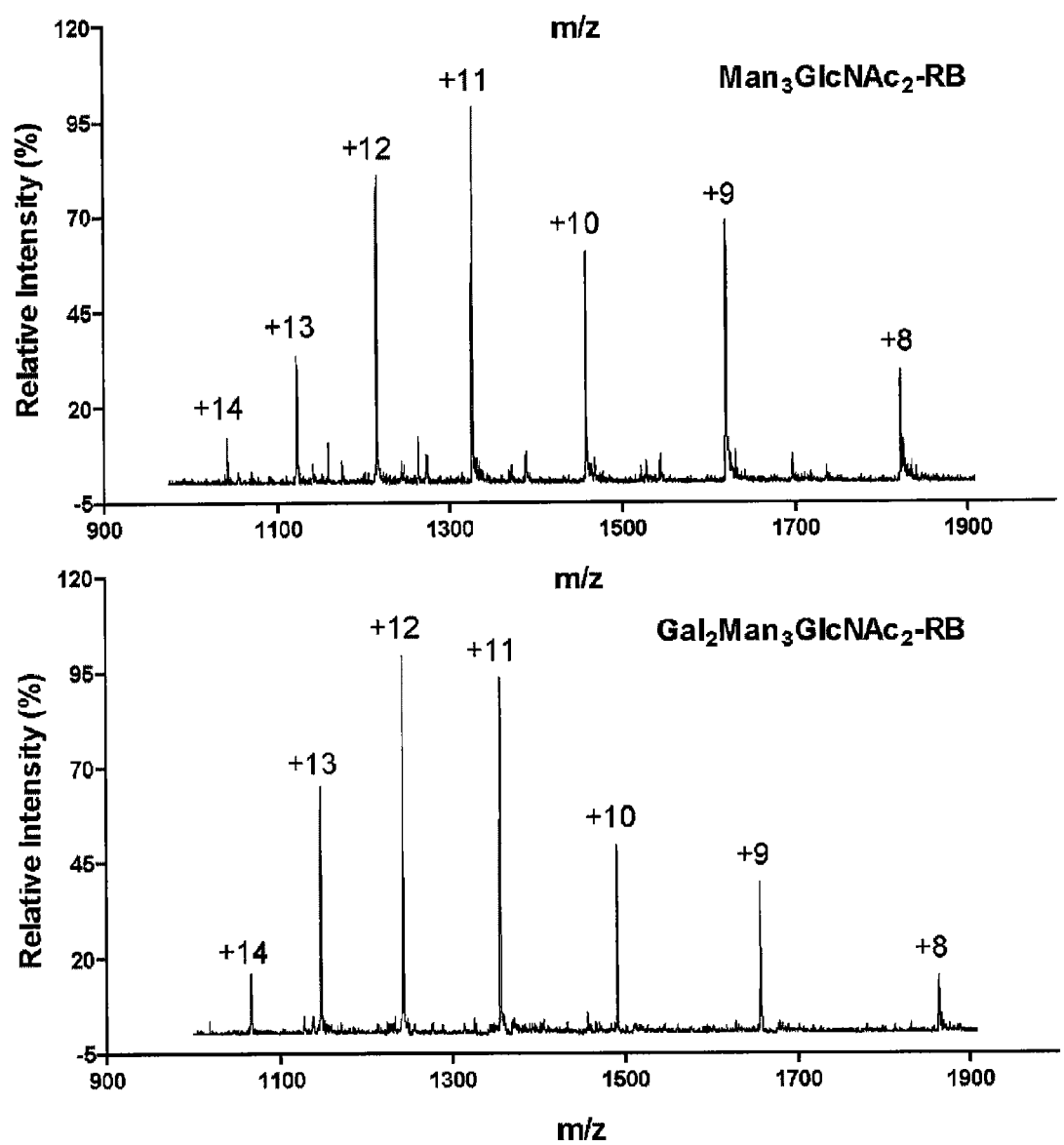

Interestingly, the glycoprotein 44, once formed, was found to be resistant to Endo-A catalyzed hydrolysis. This is understandable because glycoprotein 44 carries a nonnatural N-glycan and Endo-A is known to hydrolyze only high-mannose type natural N-glycans. Since the corresponding hexasaccharide oxazoline 39 could serve as an excellent donor substrate for the trans-glycosylation, these results suggest that the sugar oxazolines as transition state mimics are kinetically much more active for the enzymatic reaction than the "ground state" glycoprotein products thus formed. We also found that the Endo-A catalyzed trans-glycosylation of the sugar oxazoline 39 was much faster in the presence of the acceptor (GlcNAc-containing peptide or protein) than its enzymatic hydrolysis (data not shown). All these factors contribute to the formation of the trans-glycosylation product. Similarly, Endo-A catalyzed reaction of GlcNAc-RB with the tetrasaccharide oxazoline 2 [7] gave the glycoprotein 45 carrying the core N-linked pentasaccharide $Man_3GlcNAc_2$ in 82% yield (Scheme 3). Again, the observed MS (14574.5 Da, from the deconvolution of the ESI-MS data) of the isolated product matches well with the calculated MS (14575.6 Da) of glycoprotein 45. It should be noted that the efficient attachment of the core N-linked pentasaccharide ($Man_3GlcNAc_2$) to a protein would provide a key starting structure for a quick assembly of a variety of glycoforms via sequential glycosylations of the core with various glycosyltransferases. [11] The identity and homogeneity of the synthetic glycoproteins 44 ($Gal_2Man_3GlcNAc_2$-RB) and 45 ($Man_3GlcNAc_2$-RB) were clearly demonstrated by their ESI-MS as shown in FIG. 13.

The synthesis of the oligosaccharide oxazolines and glycoproteins as shown in FIGS. 10 to 12 are as follows:

Ethyl 2,3,4,6-tetra-O-acetyl-β-D-galactopyranosyl-(1→4)-3-O-acetyl-2,6-di-O-benzoyl-thio-α-D-mannopyranoside (34) A suspension of 2,3,4,6-tetra-O-acetyl-α-D-galactopyranosyl imidate (770 mg, 1.56 mmol) and ethyl 2,6-di-O-benzoyl-1-thio-α-D-mannopyranoside (560 mg, 1.29 mmol) containing activated 4 Å molecular sieves (500 mg) in dry $CH_2Cl_2$ (30 ml) was stirred under an atmosphere of argon at r.t. for 30 min. After cooling to –78° C., 0.1M TMSOTf in $CH_2Cl_2$ (0.2 ml, 0.02 mmol) was added and the mixture was stirred at –78° C. to r.t. overnight. The reaction was quenched with $Et_3N$ and the mixture was filtered. The filtrate was washed with $NaHCO_3$ solution and brine, dried over $Na_2SO_4$, and filtered. The filtrate was concentrated in vacuo and the residue was subjected to flash silica gel column chromatography (5:1 Hexanes:EtOAc) to afford two disaccharides (840 mg, 85%) as white foams. To this mixture, Py (10 ml) and $Ac_2O$ (5 ml) were added and the reaction was stirred at r.t. overnight. The mixture was diluted with $CH_2Cl_2$ (50 ml) and washed with saturated $NaHCO_3$, HCl (1N) and $H_2O$, dried over $Na_2SO_4$, and filtered. The filtrate was concentrated in vacuo and the residue was subject to flash silica gel column chromatography (3:1 Hexanes:EtOAc) to give the β-1,4-linked disaccharide 34 (302 mg, 36%) and the corresponding β-1,3-linked disaccharide (323 mg, 39%). $^1$H NMR ($CDCl_3$, 500 MHz) of compound 34: δ 8.13 (d, 2H, J=7.5 Hz, Ar—), 8.06 (d, 2H, J=8.0 Hz, Ar—), 7.68-7.66 (m, 1H, Ar—), 7.63-7.61 (m, 1H, Ar—), 7.53-7.50 (m, 1H, Ar—), 7.42-7.39 (m, 1H, Ar—), 5.68 (s, 1H, H-$2^{Man}$), 5.46 (dd, 1H, J=10 Hz, H-$3^{Man}$), 5.41 (s, 1H, H-$1^{Man}$), 5.37 (s, 1H, H-$4^{Gal}$), 5.23 (dd, 1H, J=8.0 Hz, 10.0 Hz, H-$2^{Gal}$), 4.99 (d, 1H, J=10.5 Hz, H-$3^{Gal}$), 4.79 (d, 1H, J=11.5 Hz, H-$6^{Man}$ a), 4.70 (d, 1H, J=7.5 Hz, H-$6^{Man}$ b), 4.57-4.55 (m, 2H, H-$5^{Man}$, H-$1^{Gal}$), 4.34 (t, 1H, J=9.5 Hz, H-$4^{Man}$), 4.19-4.13 (m, 1H, H-$6^{Gal}$ a), 4.09-4.05 (m, 1H, H-$6^{Gal}$ b), 3.90-3.87 (m, 1H, H-$5^{Gal}$), 2.74-2.69 (m, 2H, S$CH_2CH_3$—), 2.20 (s, 3H, $CH_3CO_2$—), 2.07 (s, 6H, 2$CH_3CO_2$—), 2.01 (s, 3H, $CH_3CO_2$—), 1.94 (s, 3H, $CH_3CO_2$—), 1.69 s, 1H, SC$H_2CH_3$—); $^{13}$C NMR ($CDCl_3$, 125 MHz) of compound 1: δ 170.41, 170.25, 170.15, 169.48, 169.31, 165.98, 165.26, 133.49, 133.38, 129.89, 129.80, 129.63, 129.55, 128.68, 128.60, 101.06, 82.23, 74.23, 71.77, 71.05, 70.55, 70.29, 69.74, 69.29, 66.76, 62.77, 61.90, 25.53, 20.84, 20.71, 20.69, 20.56, 20.41, 14.83.

$^1$H NMR ($CDCl_3$, 500 MHz) of the corresponding β-1,3-linked disaccharide: δ 8.12 (d, 2H, J=7.0 Hz, Ar—), 8.07 (d, 2H, J=7.0 Hz, Ar—), 7.63-7.60 (m, 2H, Ar—), 7.47-7.44 (m, 4H, Ar—), 5.61 (t, 1H, J=9.0 Hz, H-4), 5.50 (s, 1H, H-2), 5.45 (s, 1H, H-4'), 5.36 (s, 1H, H-1), 5.09-5.05 (m, 1H, H-2'), 4.97-4.95 (m, 1H, H-3'), 4.59-4.56 (m, 2H, H-6a, H-1), 4.51-4.49 (m, 1H), 4.44-4.42 (m, 1H), 4.31-4.29 (m, 1H), 4.20-4.16 (m, 1H), 4.13-4.09 (m, 1H), 3.94-3.92 (m, 1H), 2.75-2.70 (m, 2H, S$CH_2CH_3$—), 2.17 (s, 3H, $CH_3CO_2$—), 2.16 (s, 3H, $CH_3CO_2$—), 2.12 (s, 3H, $CH_3CO_2$—), 2.09 (s, 3H, $CH_3CO_2$—), 1.96 (s, 3H, $CH_3CO_2$—), 1.65 (s, 3H, $CH_3CO_2$—).

Benzyl 2,3,4,6-tetra-O-acetyl-β-D-galactopyranosyl-(1→4)-3-O-acetyl-2,6-di-O-benzoyl-α-D-mannopyranosyl-(1→3)-[2,3,4,6-tetra-O-acetyl-β-D-galactopyranosyl-(1→4)-3-O-acetyl-2,6-di-O-benzoyl-α-D-mannopyranosyl-(1→6)]-2-O-benzoyl-4-O-benzyl-β-D-mannopyranosyl-(1→4)-3,6-di-O-benzyl-2-deoxy-2-phthalamido-β-D-glucopyranoside (36) A suspension of donor 1 (180 mg, 0.22 mmol) and acceptor 35 [11] (70 mg, 0.07 mmol) containing activated 4 Å molecular sieves (200 mg) in dry $CH_2Cl_2$ (10 ml) was stirred under an atmosphere of argon at r.t. for 30 min. After cooling to –40° C., NIS (53 mg, 0.24 mmol) and AgOTf (6 mg, 0.02 mmol) were added and the mixture was stirred at –40° C. to r.t. overnight. The reaction was quenched with $Et_3N$ and the mixture was filtered. The filtrate was washed with $Na_2S_2O_3$ solution and brine, dried over $Na_2SO_4$, and filtered. The filtrate was concentrated in vacuo and the residue was subject to flash silica gel column chromatography (2:1 Hexanes:EtOAc) to afford 36 (172 mg, 95%) as a white foam. $^1$H NMR ($CDCl_3$, 500 MHz): δ 8.23-7.01 (m, 49H, Ar), 6.46 (s, 1H), 6.31-6.28 (m, 4H), 5.71 (s, 1H), 5.67 (s, 1H), 5.61 (s, 1H), 5.58 (d, 1H, J=9.5 Hz), 5.43 (d, 1H, J=9.0 Hz), 5.38 (s, 1H), 5.34 (s, 1H), 5.22-5.16 (m, 4H), 5.06-4.95 (m, 5H), 4.86-4.62 (m, 6H), 4.57-4.55 (m, 2H), 4.50-4.35 (m, 4H), 4.30-4.24 (m, 2H), 4.18-4.03 (m, 5H), 4.00-3.90 (m, 5H), 3.83-3.81 (m, 2H), 3.69 (d, 1H, J=8.5 Hz), 3.49 (d, 1H, J=9.5 Hz), 3.25 (d, 1H, J=9.0 Hz), 2.20 (s, 3H, $CH_3CO_2$—), 2.17 (s, 3H, $CH_3CO_2$—), 2.10 (s, 3H, $CH_3CO_2$—), 2.05 (s, 6H, 2$CH_3CO_2$—), 2.01 (s, 3H, $CH_3CO_2$—), 2.00 (s, 6H, 2$CH_3CO_2$—), 1.86 (s, 6H, 2$CH_3CO_2$—); $^{13}$C NMR ($CDCl_3$, 125 MHz): δ 170.4, 170.3, 170.2, 170.1, 170.0, 169.2, 166.3, 166.0, 164.9, 164.6, 138.3, 138.0, 137.9, 137.2, 133.4, 133.2, 132.9, 130.2, 130.0, 129.8, 129.7, 129.6, 129.3, 129.0, 128.8, 128.6, 128.5, 128.3, 128.2, 128.1, 128.0, 127.9, 127.6, 127.5, 127.3, 126.5, 123.0, 101.1, 100.9, 100.3, 99.3, 98.0, 97.2, 81.8, 79.4, 76.9, 75.7, 75.3, 75.1, 74.4, 74.3, 74.1, 74.0, 73.9, 73.5, 73.3, 71.5, 71.2, 71.1, 70.6, 70.5, 70.4, 70.3, 70.1, 70.0, 69.7, 69.6, 69.3, 69.0, 68.9, 68.6, 66.9, 66.8, 65.3, 62.7, 62.4, 61.2, 61.1, 55.6, 29.7, 20.8, 20.7, 20.6, 20.3.

2,3,4,6-Tetra-O-acetyl-β-D-galactopyranosyl-(1→4)-2,3,6-tri-O-acetyl-α-D-mannopyranosyl-(1→3)-[2,3,4,6-tetra-O-acetyl-β-D-galactopyranosyl-(1→4)-2,3,6-tri-O-acetyl-α-D-mannopyranosyl-(1→6)]-2,4-di-O-acetyl-β-D-mannopyranosyl-(1→4)-2-acetamido-1,3,6-tri-O-acetyl-2-deoxy-α,β-D-glucopyranose (37)

A mixture of 36 (172 mg, 0.30 mmol) and $NH_2NH_2.H_2O$ (6 ml) in EtOH (30 ml) was heated at 90° C. for 24 h and then concentrated in vacuo. To the oily residue were added pyridine (5 ml) and $Ac_2O$ (5 ml). The mixture was stirred at r.t. overnight. The mixture was diluted with $CH_2Cl_2$ (50 ml) and washed with saturated $NaHCO_3$, HCl (1N) and brine, dried over $Na_2SO_4$, and filtered. The filtrate was concentrated in vacuo and the residue was subject to flash silica gel column chromatography (1:3 Hexanes:EtOAc) to give the corresponding 2-acetamido 2-deoxy compound as a white foam (129 mg, 90%). $^1$H NMR (CDCl$_3$, 500 MHz): δ 7.37-7.32 (m, 20H, Ar), 6.01 (d, 1H, J=5.0 Hz), 5.42-5.27 (m, 7H), 5.22-5.15 (m, 2H), 5.04-5.00 (m, 3H), 4.90-4.83 (m, 3H), 4.78-4.69 (m, 3H), 4.67-4.61 (m, 2H), 4.57-4.52 (m, 6H), 4.35 (d, 1H, J=11.5 Hz, PhC$\underline{H}_2$—), 4.24 (d, 1H, J=12 Hz, PhC$\underline{H}_2$—), 4.19-4.03 (m, 7H), 3.96-3.89 (m, 6H), 3.81-3.78 (m, 3H), 3.71-3.60 (m, 5H), 3.23 (s, 1H), 2.20 (s, 3H, C$\underline{H}_3$CO$_2$—), 2.19 (s, 3H, C$\underline{H}_3$CO$_2$—), 2.18 (s, 3H, C$\underline{H}_3$CO$_2$—), 2.16 (s, 9H, 3C$\underline{H}_3$CO$_2$—), 2.12 (s, 3H, C$\underline{H}_3$CO$_2$—), 2.11 (s, 3H, C$\underline{H}_3$CO$_2$—), 2.08 (s, 9H, 3C$\underline{H}_3$CO$_2$—), 2.01 (s, 12H, 4C$\underline{H}_3$CO$_2$—), 1.85 (s, 3H, C$\underline{H}_3$CO$_2$—); $^{13}$C NMR (CDCl$_3$, 125 MHz): δ 171.7, 170.8, 170.7, 170.5, 170.4, 170.3, 170.2, 170.1, 169.6, 169.5, 169.4, 169.3, 138.7, 138.2, 137.8, 137.5, 101.4, 100.9, 99.8, 97.6, 97.3, 80.3, 78.2, 76.1, 75.3, 74.7, 74.4, 74.3, 73.8, 73.4, 73.0, 71.1, 70.5, 70.4, 70.3, 69.7, 69.6, 69.5, 69.3, 69.2, 69.1, 68.9, 68.7, 66.8, 66.6, 66.4, 62.4, 62.2, 60.8, 60.4, 54.6, 29.7, 24.9, 23.3, 21.0, 20.9, 20.8, 20.7, 20.6, 14.2.

A mixture of the 2-acetamido-2-deoxy compound (129 mg, 64 μmol) and 10% Pd/C (50 mg) in MeOH (10 ml) was stirred under H$_2$ atmosphere for 12 h, and then filtered through Celite. The filtrate was concentrated in vacuo. To the residue were added pyridine (5 ml) and Ac$_2$O (5 ml) and the mixture was stirred at r.t. overnight. The mixture was diluted with CH$_2$Cl$_2$ and washed with saturated NaHCO$_3$, HCl (1 N), and brine, dried over Na$_2$SO$_4$ and filtered. The filtrate was concentrated in vacuo and the residue was subjected to flash silica gel column chromatography (1:2 Hexanes:EtOAc) to give 37 (92 mg, 78%) as a white foam. $^1$H NMR (CDCl$_3$, 500 MHz): δ 6.50 (d, 1H, J=7.5 Hz), 6.25 (d, 0.5H, J=9.5 Hz), 6.17 (m, 0.5H), 6.09 (s, 1H), 6.01-5.99 (m, 1H), 5.78-5.75 (m, 1H), 5.70 (d, 0.5H, J=8.5 Hz), 5.55-5.54 (m, 1H), 5.40-5.24 (m, 4H), 5.24 (s, 1H), 5.20-5.03 (m, 3H), 5.02-4.93 (m, 6H), 4.85 (s, 0.5H), 4.79 (s, 1H), 4.72-4.69 (m, 1H), 4.59-4.46 (m, 3H), 4.36-4.28 (m, 2H), 4.21-4.11 (m, 4H), 4.07-3.93 (m, 9H), 3.86-3.82 (m, 1H), 3.81-3.67 (m, 1H), 2.19-1.93 (m, 60H, 20C$\underline{H}_3$CO$_2$—); $^{13}$C NMR (CDCl$_3$, 125 MHz): δ 171.62, 171.16, 171.11, 170.80, 170.64, 170.52, 170.48, 170.40, 170.31, 170.22, 170.15, 170.01, 169.76, 169.55, 169.49, 169.29, 169.13, 169.03, 107.30, 101.21, 100.98, 97.59, 97.14, 96.88, 92.35, 90.66, 75.19, 74.13, 73.46, 72.35, 71.05, 70.00, 70.39, 70.34, 70.17, 69.65, 69.25, 69.20, 69.10, 69.02, 68.61, 68.26, 67.19, 66.66, 66.54, 62.12, 62.02, 61.90, 60.80, 60.39, 51.82, 50.90, 47.09, 37.47, 29.68, 24.92, 24.62, 22.99, 22.83, 21.35, 21.05, 20.99, 20.94, 20.87, 20.79, 20.73, 20.64, 20.57.

O-2,3,4,6-Tetra-O-acetyl-β-D-galactopyranosyl-(1→4)-2,3,6-tri-O-acetyl-α-D-mannopyranosyl-(1→3)-[2,3,4,6-tetra-O-acetyl-β-D-galactopyranosyl-(1→4)-2,3,6-tri-O-acetyl-α-D-mannopyranosyl-(1→6)]-2,4-di-O-acetyl-β-D-mannopyranosyl-(1→4)-(1,2-dideoxy-α-D-glucopyrano)-[2,1-d]-2-oxazoline (38) Compound 37 (47 mg, 26 μmol) was dissolved in anhydrous ClCH$_2$CH$_2$Cl (3 ml) in an oven-dried flask, under an atmosphere of argon. To the solution were added TMSBr (17 μl, 128 μmol), BF$_3$.Et$_2$O (16 μl, 128 μmol) and 2,4,6-collidine (17 μl, 128 μmol). The mixture was stirred at r.t. for 5 h when TLC indicated the completion of the reaction. The mixture was diluted with CH$_2$Cl$_2$ and washed with saturated NaHCO$_3$ and brine. The organic layer was dried over Na$_2$SO$_4$ and filtered. The filtrate was concentrated in vacuo and the residue was purified by flash silica gel column chromatography (300:1 EtOAc:Et$_3$N) to give the per-acetated oxazoline derivative 38 (27 mg, 60%) as a white solid. $^1$H NMR (CDCl$_3$, 500 MHz): δ 5.97 (d, 1H, J=7.5 Hz, H-1), 5.66 (s, 1H, H-3), 5.43-5.40 (m, 3H), 5.31-5.24 (m, 3H), 5.18-5.09 (m, 3H), 5.01-4.96 (m, 3H), 4.84 (s, 1H), 4.75 (s, 1H), 4.61-4.49 (m, 4H), 4.28-4.15 (m, 7H), 4.10-4.05 (m, 3H), 3.99-3.87 (m, 7H), 3.74-3.67 (m, 3H), 3.58-3.56 (m, 1H), 3.46-3.45 (m, 1H), 2.24 (s, 3H, C$\underline{H}_3$CO$_2$—), 2.21 (s, 6H, 2C$\underline{H}_3$CO$_2$—), 2.19 (s, 6H, 2C$\underline{H}_3$CO$_2$—), 2.18 (s, 6H, 2C$\underline{H}_3$CO$_2$—), 2.15 (s, 3H, C$\underline{H}_3$CO$_2$—), 2.14 (s, 3H, C$\underline{H}_3$CO$_2$—), 2.13 (s, 3H, C$\underline{H}_3$CO$_2$—), 2.10 (s, 15H, 5C$\underline{H}_3$CO$_2$—), 2.06 (s, 3H, C$\underline{H}_3$CO$_2$—), 2.05 (s, 3H, C$\underline{H}_3$CO$_2$—), 2.02 (s, 6H, 2C$\underline{H}_3$CO$_2$—); $^{13}$C NMR (CDCl$_3$, 125 MHz): δ 170.7, 170.6, 170.4, 170.3, 170.2, 170.0, 169.8, 169.1, 166.3, 101.2, 100.9, 99.6, 99.4, 99.1, 97.5, 74.3, 73.6, 72.9, 71.1, 70.4, 70.3, 70.1, 70.0, 69.8, 69.4, 69.1, 68.9, 68.0, 66.7, 64.2, 63.6, 62.5, 62.0, 60.8, 60.7, 60.4, 20.9, 20.7, 20.6, 20.5, 14.2, 13.7.

O-β-D-Galactopyranosyl-(1→4)-α-D-mannopyranosyl-(1→3)-[β-D-galactopyranosyl-(1→4)-α-D-mannopyranosyl-(1→6)]-β-D-mannopyranosyl-(1→4)-(1,2-dideoxy-α-D-glucopyrano)-[2,1-d]-2-oxazoline (39) A solution of the peracetylated oxazoline 38 (27 mg, 15 μmol) in MeOH (2 ml) containing MeONa (3.0 μmol) was stirred at r.t. overnight. The MeOH was evaporated and the residue was dissolved in water and lyophilized to give the oxazoline 39 (15 mg, quantitative) as a white solid. $^1$H NMR (D$_2$O, 500 MHz): δ 6.02 (d, 1H, J=6.5 Hz, H-1), 5.02 (s, 1H, H-1$^{α\text{-}Man}$), 4.88 (s, 1H, H-1$^{α\text{-}Man}$), 4.67 (s, 1H, H-1$^{β\text{-}Man}$), 4.37-4.34 (m, 3H, H-2$^{β\text{-}Man}$, 2H-1$^{β\text{-}Gal}$), 4.07 (s, 1H), 4.05 (s, 1H), 4.00 (s, 1H), 3.92 (s, 1H), 3.90-3.67 (m, 22H), 3.58-3.45 (m, 6H), 3.33-3.32 (m, 1H), 3.27 (s, 1H), 1.99 (s, 3H, C$\underline{H}_3$—); $^{13}$C NMR (D$_2$O, 125 MHz): δ 168.3, 103.1, 103.0, 102.2, 101.4, 99.9, 99.4, 80.9, 78.1, 76.5, 75.4, 74.3, 72.6, 72.0, 71.3, 71.0, 70.9, 70.3, 69.6, 69.4, 69.1, 69.0, 68.6, 65.8, 65.1, 61.8, 61.1, 60.5, 60.3, 13.0.

Synthesis of glycopeptide (41) A mixture of the hexasaccharide oxazoline 39 (0.69 mg, 0.68 μmol) and the GlcNAc-tripeptide 40 (0.2 mg, 0.34 μmol) in a phosphate buffer (50 mM, pH 6.5, 100 μl) was incubated at 23° C. with the enzyme Endo-A (200 mU). The reaction was monitored by analytical HPLC on a Waters Nova-Pak C18 column (3.9×150 mm) at 40° C. with a linear gradient (0-90% MeCN containing 0.1% TFA in 25 min, flow rate 1 ml/min). Within 30 min, the GlcNAc-tripeptide was completely converted to a new species that was eluted slightly earlier than the starting material. The product was purified by preparative HPLC on a Waters preparative column (Symmetry 300, 19×300 mm) to afford the glycopeptide 41 (0.53 mg, 98%). $^1$H NMR (D$_2$O, 500 MHz): δ 5.05 (s, 1H, H-1$^{α\text{-}Man}$), 4.99 (d, 1H, J=8.5 Hz, H-1$^{GlcNAc\text{-}1}$), 4.87 (s, 1H, H-1$^{α\text{-}Man}$), 4.67 (s, 1H, H-1$^{β\text{-}Man}$), 4.56 (d, 1H, J=7.5 Hz, H-1$^{GlcNAc\text{-}2}$), 4.40 (s, 1H, H-1$^{β\text{-}Gal}$), 4.38 (s, 1H, H-1$^{β\text{-}Gal}$), 4.26 (d, 1H, J=4.4 Hz, Thr-H$_α$), 4.21-4.19 (m, 3H), 4.08 (s, 1H), 3.99 (s, 1H), 3.94-3.50 (m, 38H), 2.78 (dd, 1H, J=5.8, 16.0 Hz, Asn-H$_β$), 2.65 (dd, 1H, J=16.0, 7.8 Hz, Asn-H$_б$), 2.01 (s, 3H, NHCOC$\underline{H}_3$—), 1.95 (s, 3H, NHCOC$\underline{H}_3$—), 1.89-1.85 (m, 1H, Leu-H$_β$), 1.15 (d, 3H, J=5.5 Hz, Thr-CH$_3$—), 0.87 (d, 3H, J=6.5 Hz, Leu-C$\underline{H}_3$—), 0.82 (t, 3H, J=7.0 Hz, Leu-C$\underline{H}_3$—); ESI-MS: MS=1604.5; Found, 1605.0 (M+H)$^+$, 1118.5 (M-2Gal-Man+H)$^+$, 956.5 (M-2Gal-2Man+H)$^+$, 721.8 (M-Gal+2H)$^{2+}$, 641.3 (M-2Gal+2H)$^{2+}$, 559.9 (M-2Gal-Man+2H)$^{2+}$, 478.8 (M-2Gal-2Man+2H)$^{2+}$.

Preparation of GlcNAc-containing Ribonuclease B (43)—(GlcNAc-RB) The bovine Ribonuclease B (42) obtained from Sigma was purified by borate-phosphate cation exchange chromatography according to the reported procedure.[3] The purified Ribonuclease B (50 mg) was dissolved in a phosphate buffer (50 mM, PH 6.0, 2 ml). To the solution was added Endo-H (500 mU) and the mixture was incubated at 37° C. for 5 h. The partially de-glycosylated product was purified by preparative HPLC to give the GlcNAc-RB (43)

(36 mg, 80%). ESI-MS: calculated MS=13886; Found, 1737 $(M+8H)^{8+}$, 1544 $(M+9H)^{9+}$, 1390 $(M+10H)^{10+}$, 1263 $(M+11H)^{11+}$, 1158 $(M+12H)^{12+}$, 1069 $(M+13H)^{13+}$, 993 $(M+14H)^{14+}$.

Synthesis of glycoprotein (44)—(Gal$_2$Man$_3$GlcNAc$_2$-RB) A mixture of the hexasaccharide oxazoline 39 (0.57 mg, 0.56 µmol) and the GlcNAc-RNB protein (43) (3.9 mg, 0.28 µmol) in a phosphate buffer (50 mM, pH 6.5, 150 µl) was incubated at 23° C. with the enzyme Endo-A (200 mU). The reaction was monitored by analytical HPLC on a Waters Nova-Pak C18 column (3.9×150 mm) at 40° C. with a linear gradient (0-90% MeCN containing 0.1% TFA in 25 min, flow rate 1 ml/min). Within 2 h, the GlcNAc-RB protein was completely converted to a new species that was eluted slightly earlier than GlcNAc-RB. The product was purified by preparative HPLC on a Waters preparative column (Symmetry 300, 19×300 mm) to afford the glycoprotein 44 (4.02 mg, 96%). ESI-MS: calculated MS=14900; Found, 1863.4 $(M+8H)^{8+}$, 1656.4 $(M+9H)^{9+}$, 1490.9 $(M+10H)^{10+}$, 1355.5 $(M+11H)^{11+}$, 1242.6 $(M+12H)^{12+}$, 1147.1 $(M+13H)^{13+}$, 1065.2 $(M+14H)^{14+}$.

Synthesis of glycoprotein (45)—(Man$_3$GlcNAc$_2$-RB) The Endo-A catalyzed transglycosylation between the tetra-saccharide oxazoline 2 [11] and the GlcNAc-RB 43 protein was performed in the same way as the synthesis of glycoprotein 44 to afford the glycoprotein 45 in 82% isolated yield. ESI-MS: calculated MS=14575; Found, 1823 $(M+8H)^{8+}$, 1620 $(M+9H)^{9+}$, 1459 $(M+10H)^{10+}$, 1326 $(M+11H)^{11+}$, 1216 $(M+12H)^{12+}$, 1122 $(M+13H)^{13+}$, 1042 $(M+14H)^{14+}$.

The high-yield enzymatic trans-glycosylation with the use of synthetic sugar oxazoline as the donor substrate opens a new avenue toward glycoprotein synthesis and remodeling. The endoglycosidase-catalyzed ligation with GlcNAc-containing proteins proceeds in a regio- and stereospecific manner and in an excellent yield under mild conditions, without the need of any protection groups. The chemoenzymatic approach is highly convergent and allows totally independent preparation of the oligosaccharide and protein portions, thus avoiding the long-standing problem of "incompatibility" of protecting group manipulations in glycopeptide synthesis. In addition, this study has demonstrated that nonnatural oligosaccharide could also serve as efficient donor substrate, making it possible to construct both natural and tailor-made glycoproteins.

Modified Antibodies

The following example illustrates methods of improving the biological activity of an antibody by glycosylation engineering.

Homogenous Preparation of Antibodies

To obtain a homogeneous preparation of mAbs with a particular glycosylation state, a combined high-yield cellular expression with in vitro glycosylation engineering using a chemoenzymatic transglycosylation system was utilized [26]. Combined with the power of chemical synthesis of oligosaccharide oxazoline substrates for the endo-enzymes, this approach allows for the preparation of an array of defined glycosylation states (natural or unnatural) of mAbs or their IgG-Fc domain, which, in turn, allows for a systematic analysis of the structure-activity relationships of IgG glycosylation and the corresponding ADCC activity. Following the pioneering work of Jeffries et al., use of the hingeless human IgG-Fc, the delta-h-Fc (aa 231-447) as a model system, in which the hinge region of Fc was deleted, is used [27, 3 g]. Using this truncated Fc form rather than a whole human antibody IgG or IgG-Fc as a model system greatly simplifies the synthesis as well as the subsequent structure-function relationship studies.

Figure 15:
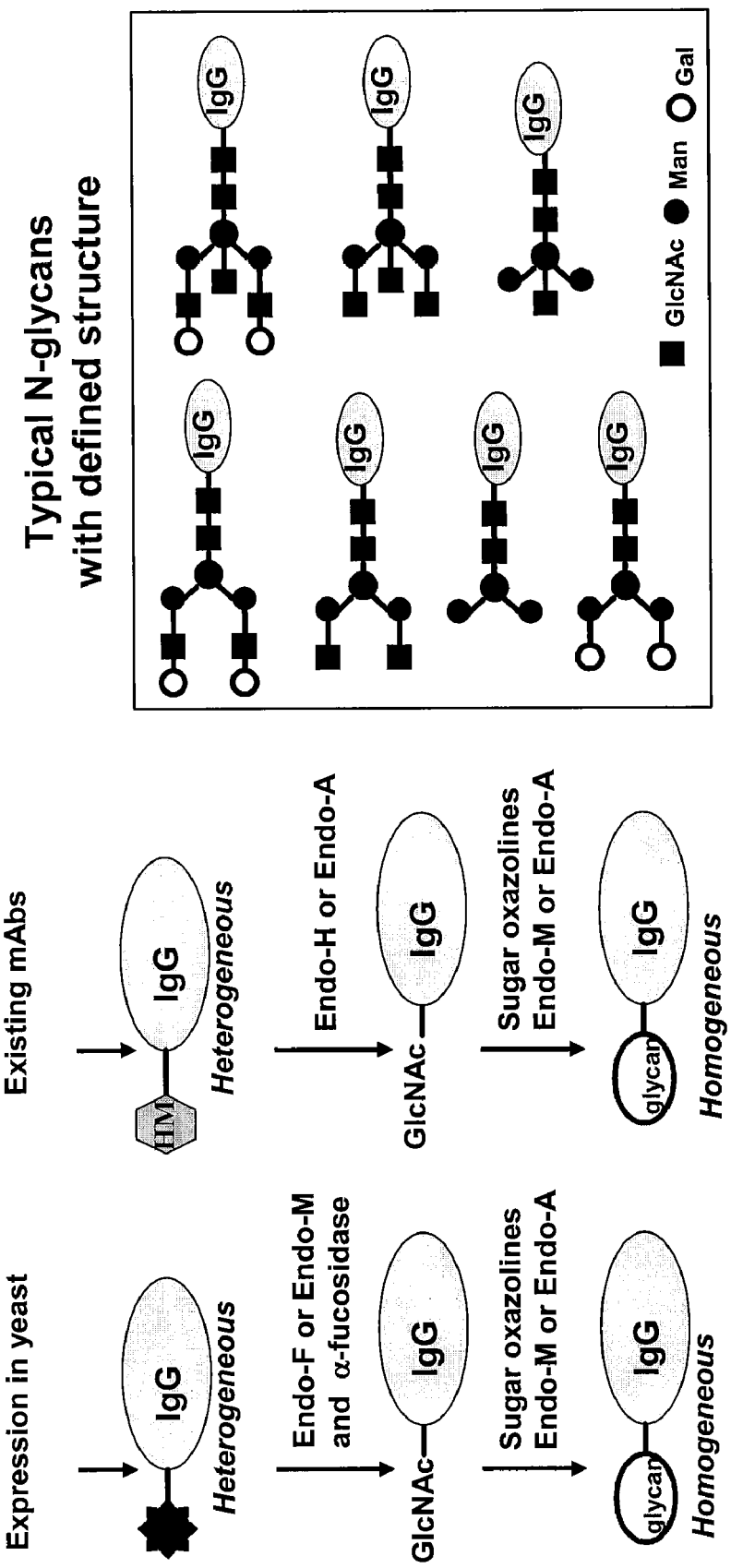
FIG. 15 shows the synthesis of glycoforms of IgG or IgG-Fc domain by a combined cellular and chemoenzymatic approach.

At least two expression systems can be used for expressing the hingeless IgG-Fc. The instant invention is not limited by the expression systems described herein. One expression system is the CHO-K1 cell system that was previously used to overproduce human delta-h-Fc glycoprotein [27, 3 g]. The plasmid encoding the delta-h-Fc gene (aa231-447) is constructed in exactly the same way as reported, using the commercially available plasmid pg1 L243H as a source of the $C_H$ g1 gene [27, 3 g]. The system produces a delta-h-Fc glycoprotein with a heterogeneous N-glycan. Another expression system is a yeast-based system. This expression system leads to the expression of the glycoprotein in a high-yield yeast mutant expression system, which produces the IgG-Fc glycoprotein with a high-mannose type oligosaccharide attached. After overproduction and subsequent purification, the resulting glycoprotein delta-h-Fc is treated with a mixture of Endo-F2 or Endo-M and a fucosidase (to remove the heterogeneous sugar chains expressed from the CHO— cell line), or treated with Endo-H or Endo-A (to remove the high-mannose type oligosaccharides produced from the yeast system). This removes all the heterogeneous N-glycans, while leaving only the inner most GlcNAc attached at the glycosylation site (Asn-297). Subsequently, the resulting GlcNAc-containing IgG-Fc will serve as the acceptor substrate for transglycosylation to add back various homogeneous oligosaccharides from sugar oxazolines under the catalysis of a suitable endo-enzyme or its mutants [28]. Using various synthetic sugar oxazolines as the donor substrates, the ENGase-catalyzed transglycosylation provides various glycosylation states of delta-h-Fc and mAbs with defined oligosaccharide structure. These include the N-glycan core structures, those with fucose and those with bisecting GlcNAc structure. In addition to the method described above, this approach also applies to whole IgG antibody preparations. The general approach is depicted in the FIG. 15. In addition to the method described above, this approach applies to whole IgG antibody preparations.

REFERENCES

The references cited herein are incorporated by reference herein for all purposes.

1

1a A. Varki, *Glycobiology* 1993, 3, 97-130;
1b R. A. Dwek, *Chem. Rev.* 1996, 96, 683-720;
1c P. M. Rudd, T. Elliott, P. Cresswell, I. A. Wilson, R. A. Dwek, *Science* 2001, 291, 2370-2376.
1d J. N. Arnold, R. M. Wormald, R. B. Sim, P. M. Rudd, R. A. Dwek, *Annu. Rev. Immunol.,* 2007, 25, 21050.
1e. R. Jerfferis, Biotechnol. Prog., 2005, 21, 11-6.

2

2a G. Arsequell, G. Valencia, *Tetrahedron. Asymmetry* 1999, 10, 3045-3094;
2b K. M. Koeller, C. H. Wong, *Nat. Biotechnol.* 2000, 18, 835-841;
2c O. Seitz, *Chem Bio Chem* 2000, 1, 214-246
2d H. Herzner, T. Reipen, M. Schultz, H. Kunz, *Chem. Rev.* 2000, 100, 4495-4538;
2e B. G. Davis, *Chem. Rev.* 2002, 102, 579-601;
2f M. J. Grogan, M. R. Pratt, L. A. Marcaurelle, C. R. Bertozzi, *Annu. Rev. Biochem.* 2002, 71, 593-634;
2g P. H. Seeberger, *Chem. Commun.* 2003, 1115-1121;
2h S. Hanson, M. Best, M. C. Bryan, C. H. Wong, *Trends Biochem. Sci.* 2004, 29, 656-663;
2i B. G. Davis, *Science* 2004, 303, 480-482;
2j C. H. Wong, *J. Org. Chem.* 2005, 70, 4219-4225.

3

3a D. Macmillan, C. R. Bertozzi, *Angew. Chem.* 2004, 116, 1379-1383; *Angew. Chem. Int. Ed.* 2004, 43, 1355-1359;

3b T. J. Tolbert, C. H. Wong, *Methods Mol. Biol.* 2004, 283, 255-266;

3c J. D. Warren, J. S. Miller, S. J. Keding, S. J. Danishefsky, *J. Am. Chem. Soc.* 2004, 126, 6576-6578;

3d X. Geng, V. Y. Dudkin, M. Mandal, S. J. Danishefsky, *Angew. Chem.* 2004, 116, 2616-2619; *Angew. Chem. Int. Ed.* 2004, 43, 2562-2565

3e B. G. Davis, R. C. Lloyd, J. B. Jones, *J. Org. Chem.* 1998, 63, 9614-9615;

3f D. Macmillan, R. M. Bill, K. A. Sage, D. Fern, S. L. Flitsch, *Chem. Biol.* 2001, 8, 133-145;

3g G. M. Watt, J. Lund, M. Levens, V. S. Kolli, R. Jefferis, G. J. Boons, *Chem. Biol.* 2003, 10, 807-814

3h J. Ni, S. Singh, L. X. Wang, *Bioconjugate Chem.* 2003, 14, 232-238

4

4a S. Mezzato, M. Schaffrath, C. Unverzagt, *Angew. Chem.* 2005, 117, 1677-1681; *Angew. Chem. Int. Ed.* 2005, 44, 1650-1654;

4b M. Fumoto, H. Hinou, T. Matsushita, M. Kurogochi, T. Ohta, T. Ito, K. Yamada, A. Takimoto, H. Kondo, T. Inazu, S, Nishimura, *Angew. Chem.* 2005, 117, 2590-2593; *Angew. Chem. Int. Ed.* 2005, 44, 2534-2537;

4c T. Matsushita, M. Hinou, M. Kurogochi, H. Shimizu, S. Nishimura, *Org. Lett.* 2005, 7, 877-880;

4d Y. Kajihara, N. Yamamoto, T. Miyazaki, H, Sato, *Curr. Med. Chem.* 2005, 12, 527-550.

5

5a K. Yamamoto, *J. Biosci. Bioeng.* 2001, 92, 493-501;

5b L. X. Wang, S. Singh, J. Ni, in *Synthesis of Carbohydrates through Biotechnology* (Eds.: P. G. Wang, Y. Ichikawa), American Chemical Society, Washington, D.C., 2004, pp. 73-92.

6

6a K. Takegawa, M. Tabuchi, S. Yamaguchi, A. Kondo, I. Kato, S. Iwahara, *J. Biol. Chem.* 1995, 270, 3094-3099;

6b K. Haneda, T. Inazu, K. Yamamoto, H. Kumagai, Y. Nakahara, A. Kobata, *Carbohydr. Res.* 1996, 292, 61-70;

6c L. X. Wang, J. Q. Fan, Y. C. Lee, *Tetrahedron Lett.* 1996, 37, 1975-1978;

6d L. X. Wang, M. Tang, T. Suzuki, K. Kitajima, Y. Inoue, S. Inoue, J. Q. Fan, Y. C. Lee, *J. Am. Chem. Soc.* 1997, 119, 11137-11146;

6e M. Mizuno, K. Haneda, R. Iguchi, I. Muramoto, T. Kawakami, S. Aimoto, K. Yamamoto, T. Inazu, *J. Am. Chem. Soc.* 1999, 121, 284-290;

6f K. Haneda, M. Tagashira, E. Yoshino, M. Takeuchi, T. Inazu, K. Toma, H. Iijima, Y. Isogai, M. Hori, S. Takamatsu, Y. Fujibayashi, K. Kobayashi, K. Yamamoto, *Glycoconjugate J.* 2004, 21, 377-386;

6g K. Fujita, K. Takegawa, *Biochem. Biophys. Res. Commun.* 2001, 282, 678-682;

6h S. Singh, J. Ni, L. X. Wang, *Bioorg. Med. Chem. Lett.* 2003, 13, 327-330;

6i H. Li, S. Singh, Y. Zeng, H. Song, L. X. Wang, *Bioorg. Med. Chem. Lett.* 2005, 15, 895-898.

7 L. X. Wang, H. Song, S. Liu, H. Lu, S. Jiang, J. Ni, H. Li, *Chem Bio Chem* 2005, 6, 1068-1074.

8 K. Takegawa, S. Yamaguchi, A. Kondo, H. Iwamoto, M. Nakoshi, I. Kato, S. Iwahara, *Biochem. Int.* 1991, 24, 849-855.

9 K. Yamamoto, S. Kadowaki, J. Watanabe, H. Kumagai, *Biochem. Biophys. Res. Commun.* 1994, 203, 244-252.

10 D. H. Crout, G. Vic, *Curr. Opin. Chem. Biol.* 1998, 2, 98-111.

11 B. Li, Y. Zeng, S. Hauser, H. Song, L. X. Wang, *J. Am. Chem. Soc.* 2005, 127, 9692-9693.

12

12a K. A. Brameld, W. D. Shrader, B. Imperiali, W. A. Goddard, 3rd, *J. Mol. Biol.* 1998, 280, 913-923;

12b A. C. Terwisscha van Schelting a, S. Armand, K. H. Kalk, A. Isogai, B. Henrissat, B. W. Dijkstra, *Biochemistry* 1995, 34, 15619-15623;

12c I. Tews, A. C. Terwisscha van Schelting a, A. Perrakis, K. S. Wilson, B. W. Dijkstra, *J. Am. Chem. Soc.* 1997, 119, 7954-7959.

13

13a B. L. Mark, D. J. Vocadlo, S. Knapp, B. L. Triggs-Raine, S. G. Withers, M. N. James, *J. Biol. Chem.* 2001, 276, 10330-10337;

13b S. J. Williams, B. L. Mark, D. J. Vocadlo, M. N. James, S. G. Withers, *J. Biol. Chem.* 2002, 277, 40055-40065.

14 M. Fujita, S. Shoda, K. Haneda, T. Inazu, K. Takegawa, K. Yamamoto, *Biochim. Biophys. Acta* 2001, 1528, 9-14.

15 S. Kobayashi, T. Kiyosada, S. Shoda, *J. Am. Chem. Soc.* 1996, 118, 13113-13114.

16 S. Shoda, T. Kiyosada, H. Mori, S. Kobayashi, *Heterocycles* 2000, 52, 599-602.

17

17a S. Kobayashi, H. Morii, R. Itoh, S. Kimura, M. Ohmae, *J. Am. Chem. Soc.* 2001, 123, 11825-11826;

17b S. Kobayashi, S. Fujikawa, M. Ohmae, *J. Am. Chem. Soc.* 2003, 125, 14357-14369;

17c H. Ochiai, M. Ohmae, S. Kobayashi, *Carbohydr. Res.* 2004, 339, 2769-2788.

18 V. Y. Dudkin, D. Crich, *Tetrahedron Lett.* 2003, 44, 1787-1789.

19 T. K. M. Shing, A. S. Perlin, *Carbohydr. Res.* 1984, 130, 65-72.

20 R. U. Lemieux, R. M. Ratcliffe, *Can. J. Chem.* 1979, 57, 1244-1251.

21 S. Nakabayashi, C. D. Warren, R. W. Jeanloz, *Carbohydr. Res.* 1986, 150, C7-C10.

22 G. W. J. Twaddle, D. Y. Yashunsky, A. V. Nikolaev, *Org. Biomol. Chem.* 2003, 1, 623-628.

23

23a S. David, A. Malleron, C. Dini, *Carbohydr. Res.* 1989, 188, 193-200;

23b W. Günther, H. Kunz, *Carbohydr. Res.* 1992, 228, 217-241;

23c W. Günther, H. Kunz, *Angew. Chem.* 1990, 102, 1068-1069; *Angew. Chem. Int. Ed. Engl.* 1990, 29, 1050-1051.

24 M. P. DeNinno, J. B. Etienne, K. C. Duplantier, *Tetrahedron Lett.* 1995, 36, 669-672.

25

25a R. S. Rush, P. L. Derby, D. M. Smith, C. Merry, G. Rogers, M. F. Rohde, V. Katta, *Anal. Chem.* 1995, 67, 1442-1452;

25b S. Elliott, T. Lorenzini, S. Asher, K. Aoki, D. Brankow, L. Buck, L. Busse, D. Chang, J. Fuller, J. Grant, N. Hemday, M. Hokum, S. Hu, A. Knudten, N. Levin, R. Komorowski, F. Martin, R. Navarro, T. Osslund, G. Rogers, N. Rogers, G. Trail, J. Egrie, *Nat. Biotechnol.* 2003, 21, 414-421.

26 H. Li, B. Li, H. Song, L. Breydo, I. V. Baskakov, L. X. Wang, *J. Org. Chem.* 2005, 70, 9990-9996.

27 Lund, J., Takahashi, N., Popplewell, A., Goodall, M., Pound, J. D., Tyler, R., King, D. J., and Jefferis, R. *Eur J. Biochem.,* 2000. 267:7246-7257

28 Li, B., Song, H., Hauser, S., and Wang, L. X. *Org. Lett.,* 2006 8:3081-3084.

What is claimed is:

1. A method of generating remodeled and homogeneous functionalized glycopeptide or glycoprotein, the method comprising:
   (a) preparing an acceptor GlcNAc-containing peptide or protein that accepts an oligosaccharide; and
   (b) enzymatically adding the oligosaccharide to the acceptor GlcNAc-containing peptide or protein catalyzed by an endoglycosidase enzyme selected from the group consisting of Endo A and Endo M, wherein the oligosaccharide is a synthetic oligosaccharide oxazoline comprising a sugar chain containing monosaccharide residues and glycosidic linkages to form an intermediate glycopeptide or glycoprotein; and
   (c) adding a biologically active agent or a tag to the intermediate glycopeptide or glycoprotein to form the functionalized glycopeptide or glycoprotein.

2. The method of claim 1, wherein the acceptor GlcNAc-containing peptide or protein is an antibody or fragment thereof.

3. The method of claim 1, wherein the synthetic oligosaccharide oxazoline is a di-, tri-, tetra-, penta-, hexyl-, hepta-, octyl-, nona-, deca-, or undeca-saccharide oxazoline.

4. The method of claim 1, wherein the intermediate glycopeptide or glycoprotein further comprises an azido group; wherein the biologically active agent or tag further comprises an alkynyl group; and wherein in step (c) the adding comprises reacting said azido group and said alkynyl group to form a triazole linker group in said functionalized glycopeptide or glycoprotein.

5. The method of claim 1, wherein the step of preparing an acceptor GlcNAc-containing peptide or protein comprises
   (a) providing a peptide or protein substrate comprising at least two GlcNAc residues and at least one GlcNAc-GlcNAc bond; and
   (b) treating the peptide or protein substrate with an endoglycosidase to hydrolyze a bond between two of the GlcNAc residues positioned closest to the peptide or protein substrate thereby forming a peptide or protein substrate with a single GlcNAc-moiety.

6. The method of claim 1, wherein the tag is a drug, toxin, fluorescent probe, biotin, a PEG, lipid, or polypeptide.

7. The method of claim 6, wherein the tag is polypeptide selected from the group consisting of adrenocorticotropic hormone (ACTH); ebiratide; angiotensin; angiotensin II; asparaginase; atrial natriuretic peptide; atrial sodium diuretic peptide; bacitracin; beta-endorphin; blood coagulation factors VII, VIII and IX; blood thymic factor (FTS); blood thymic factor derivatives; bombesin; bone morphogenic factor; bone morphogenic protein (BMP); bradykinin; caerulein; calcitonin gene related polypeptide (CGRP); calcitonins; a cell growth factor selected from the group consisting of EGF, TGF-alpha, TGF-beta, PDGF, acidic FGF, and basic FGF; cerulein; chemokine; cholecystokinin; cholecystokinin-8 (CCK-8); cholecystokinin-pancreozymin (CCK-PZ); colistin; colony-stimulating factor; corticotropin-releasing factor (CRF); cytokine; desmopressin; dinorphin; a dipeptide; dismutase; dynorphin; eledoisin; endorphin; endothelin; endotherin; enkephalin; epidermal growth factor (EGF); erythropoietin (EPO); follicle-stimulating hormone (FSH); gallanin; gastric inhibitory polypeptide; gastrin-releasing polypeptide (GRP); gastrin; G-CSF; glucagon; glutathione peroxidase; glutathio-peroxidase; a gonadotropin selected from the group consisting of human chorionic gonadotrophin (HCG) and .alpha. and .beta. subunits thereof; gramicidin; gramicidines; growth factor (EGF); growth hormone-releasing factor (GRF); growth hormone; human artrial natriuretic polypeptide (h-ANP); human placental lactogen; insulin; insulin-like growth factor; interferon; interleukin; kallikrein; kyotorphin; luliberin; luteinizing hormone (LH); luteinizing hormone-releasing hormone (LH-RH); lysozyme chloride; melanocyte-stimulating hormone (MSH); melanophore stimulating hormone; mellitin; motilin; muramyl; muramyldipeptide; nerve growth factor (NGF); neuropeptide Y; neurotensin; oxytocin; pancreastatin; pancreatic polypeptide; pancreozymin; parathyroid hormone (PTH); pentagastrin; pituitary adenyl cyclase-activating polypeptides (PACAPs); platelet-derived growth factor (PDGF); polymixin B; prolactin; protein synthesis stimulating polypeptide; PTH-related protein; relaxin; renin; secretin; serum thymic factor; somatomedins; thrombopoietin (TPO); thymic humoral factor (THF); thymopoietin; thymosin; thymostimulin; thyroid hormone releasing hormone; thyroid-stimulating hormone (TSH); thyrotropin releasing hormone (TRH); trypsin; tuftsin; tumor growth factor (TGF-alpha); tumor necrosis factor (TNF); tyrocidin; urogastrone; urokinase; vasoactive intestinal polypeptide (VIP); and vasopressin.

8. The method of claim 6, wherein the tag is a drug.

9. The method of claim 2, wherein the GlcNAc containing peptide or protein is an antibody selected from the group consisting of 17b, 48d, A32, C11, 2G12, F240, IgG1b12, 19e, X5, TNX-355 and F91.

* * * * *

UNITED STATES PATENT AND TRADEMARK OFFICE
CERTIFICATE OF CORRECTION

| | | |
|---|---|---|
| PATENT NO. | : 7,807,405 B2 | Page 1 of 1 |
| APPLICATION NO. | : 11/760434 | |
| DATED | : October 5, 2010 | |
| INVENTOR(S) | : Lai-Xi Wang | |

It is certified that error appears in the above-identified patent and that said Letters Patent is hereby corrected as shown below:

Column 1, lines 5-10: "Work related to the invention was conducted in the performance of NIAID/NIH contract no. NIAID/NIH R01 AI067111-01A1 and NIGMS/NIH R01 GM073717-A2. As a result of such contracts, the U.S. Government has certain rights in the invention described herein."

Should be: This invention was made with government support under Grant Numbers AI067111 and GM073717 awarded by the National Institutes of Health. The government has certain rights in the invention.

Signed and Sealed this
Fifteenth Day of January, 2013

David J. Kappos
*Director of the United States Patent and Trademark Office*